United States Patent
Clemons et al.

(10) Patent No.: US 12,129,272 B2
(45) Date of Patent: Oct. 29, 2024

(54) GLYCOSYLTRANSFERASE INHIBITORS

(71) Applicants: CALIFORNIA INSTITUTE OF TECHNOLOGY, Pasadena, CA (US); UNIVERSITY OF TENNESSEE RESEARCH FOUNDATION, Memphis, TN (US)

(72) Inventors: William M. Clemons, Colliervielle, CA (US); Michio Kurosu, Memphis, TN (US)

(73) Assignees: CALIFORNIA INSTITUTE OF TECHNOLOGY; UNIVERSITY OF TENNESSEE RESEARCH FOUNDATION

( * ) Notice: Subject to any disclaimer, the term of this patent is extended or adjusted under 35 U.S.C. 154(b) by 0 days.

(21) Appl. No.: 18/104,297

(22) Filed: Feb. 1, 2023

(65) Prior Publication Data
US 2024/0199677 A1 Jun. 20, 2024

Related U.S. Application Data

(63) Continuation of application No. 16/960,608, filed as application No. PCT/US2019/013152 on Jan. 11, 2019, now Pat. No. 11,597,743.

(60) Provisional application No. 62/616,657, filed on Jan. 12, 2018.

(51) Int. Cl.
| | | |
|---|---|---|
| C07H 19/06 | (2006.01) |
| A61K 31/337 | (2006.01) |
| A61K 31/7072 | (2006.01) |
| C07H 1/00 | (2006.01) |

(52) U.S. Cl.
CPC ............... C07H 19/06 (2013.01); C07H 1/00 (2013.01); *A61K 31/337* (2013.01); *A61K 31/7072* (2013.01)

(58) Field of Classification Search
None
See application file for complete search history.

(56) References Cited

FOREIGN PATENT DOCUMENTS

JP 2003532736 A 11/2003

OTHER PUBLICATIONS

Mitachi, ACS Omega 2018, 3, 1726-1739. (Year: 2018).*
Mitachi et al., Novel FR-900493 Analogues That Inhibit the Outgrowth of *Clostridium difficile* Spores, ACS Omega dated 2018, 14 pages, vol. 3.

\* cited by examiner

*Primary Examiner* — Layla D Berry
(74) *Attorney, Agent, or Firm* — Fish IP Law, LLP

(57) ABSTRACT

The present invention relates to methods of treating bacterial infections and cancer in a subject in need thereof, comprising administering to the subject a therapeutically effective amount of at least one compound provided herein.

9 Claims, 9 Drawing Sheets

DPAGT1 Inhibition

Western Blot Assays with β-Catenin

β-catenin: a substrate for N-glycosylation
β-Actin: a negative control

GLYCOSYLTRANSFERASE INHIBITORS

RELATED APPLICATIONS

This application is a Continuation of U.S. Ser. No. 16/960,608, filed Jul. 8, 2020, which is a 35 U.S.C. § 371 filing of International Application No. PCT/US2019/013152, filed Jan. 11, 2019, which claims the benefit of U.S. Provisional Patent Application No. 62/616,657, filed on Jan. 12, 2018. The entire contents of this application are herein incorporated by reference in its entirety.

GOVERNMENT SUPPORT

The invention was made with government support under Grant No. GM114611 awarded by the National Institute of Health. The government has certain rights in the invention.

BACKGROUND OF THE INVENTION

A biological target of current interest is dolichyl-phosphate N-acetylglucosamine-phosphotransferase (DPAGT1). DPAGT1 is the first committed enzyme for glycoprotein biosynthesis. Cell surface polysaccharides play important roles in numerous biological processes in living organisms, and abnormal glycosylation of cell surface proteins takes place during which normal cells progress to a malignant neoplastic state. Thus, the modification of cell surface glycosylation is a characteristic of many cancer cells. Many of the recently developed tumor markers are carbohydrate antigens. Although it is an extremely challenging subject to discover drug-like glycosyltransferases to block the biosynthesis of specific branching processes in cancer cells, N-glycan biosynthesis can be terminated by inhibition of the first committed enzyme, DPAGT1. Selective DPAGT1 inhibitors have the promising therapeutic potential for certain solid cancers that require increased branching of N-linked glycans in their growth progressions. Because strong inhibition of DPAGT1 may cause cytotoxicity, DPAGT1 inhibitors also have promising therapeutic potential as antibacterial agents.

There remains a need for preparing structurally diverse DPAGT1 inhibitors, particularly ones that are potent and/or selective for the treatment of bacterial infections and cancer.

SUMMARY OF THE INVENTION

Provided herein are compounds and methods of using these compounds to inhibit DPAGT1 in an individual in need thereof.

Accordingly, in an aspect, provided herein are compounds of Formula I:

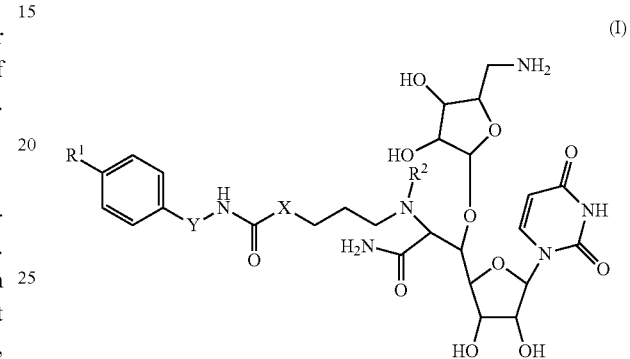

(I)

or a pharmaceutically acceptable salt thereof;
wherein
$R^1$ is $C_1$-$C_{10}$ alkyl or piperazine-O-Ph, wherein Ph is optionally substituted with $C_1$-$C_4$ alkyl or $OC_1$-$C_4$ alkyl, wherein $C_1$-$C_4$ alkyl or $OC_1$-$C_4$ alkyl is optionally further substituted with 1, 2, or 3 halo;
$R^2$ is H or $C_1$-$C_6$ alkyl;
X is selected from the group consisting of absent, —$(CH_2)_m$—, and —NH—;
Y is absent or —$(CH_2)_n$—; and
m and n are, independently at each occurrence, 1, 2, or 3.

In an embodiment, $R^1$ is piperazine-O-Ph-$CF_3$; X is absent; and Y is —$CH_2$—.

In another embodiment, the compound of Formula I is

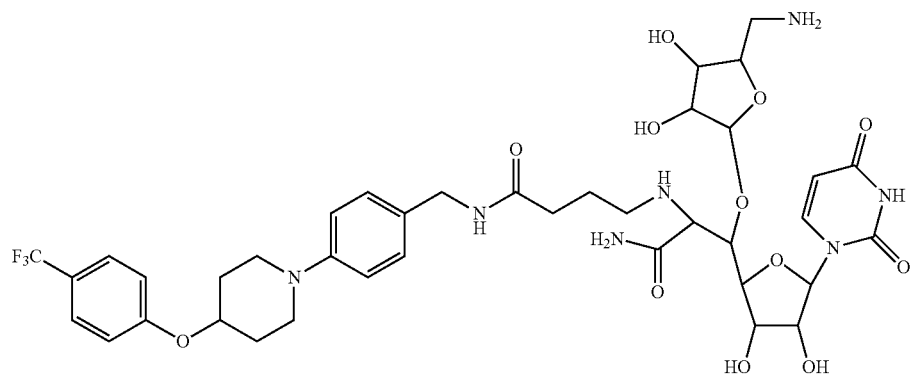 [SMILES: NCC1OC(OC(C(NCCCC(=O)NCc2ccc(N3CCC(Oc4ccc(C(F)(F)F)cc4)CC3)cc2)C(N)=O)C2OC(n3ccc(=O)[nH]c3=O)C(O)C2O)C(O)C1O]

or a pharmaceutically acceptable salt thereof.

In still another embodiment, the compound of Formula I is

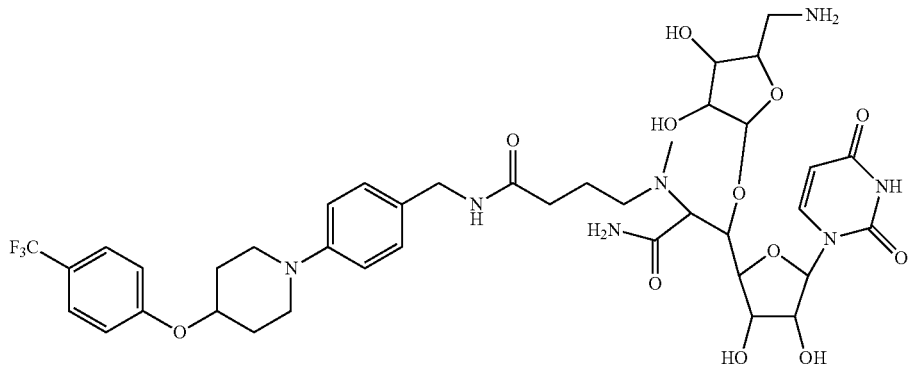 [SMILES: CN(CCCC(=O)NCc1ccc(N2CCC(Oc3ccc(C(F)(F)F)cc3)CC2)cc1)C(C(N)=O)C(OC1OC(CN)C(O)C1O)C1OC(n2ccc(=O)[nH]c2=O)C(O)C1O]

or a pharmaceutically acceptable salt thereof.

In yet another embodiment, $R^1$ is $C_7$ alkyl; X is absent; and Y is absent.

In an embodiment, the compound of Formula I is

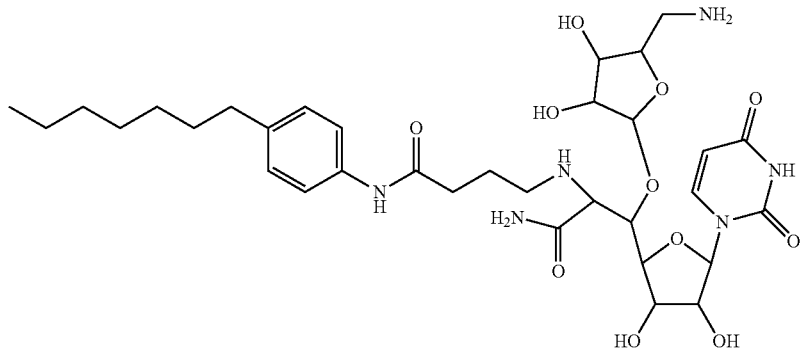 [SMILES: CCCCCCCc1ccc(NC(=O)CCCNC(C(N)=O)C(OC2OC(CN)C(O)C2O)C2OC(n3ccc(=O)[nH]c3=O)C(O)C2O)cc1]

or a pharmaceutically acceptable salt thereof.

In another embodiment, the compound of Formula I is

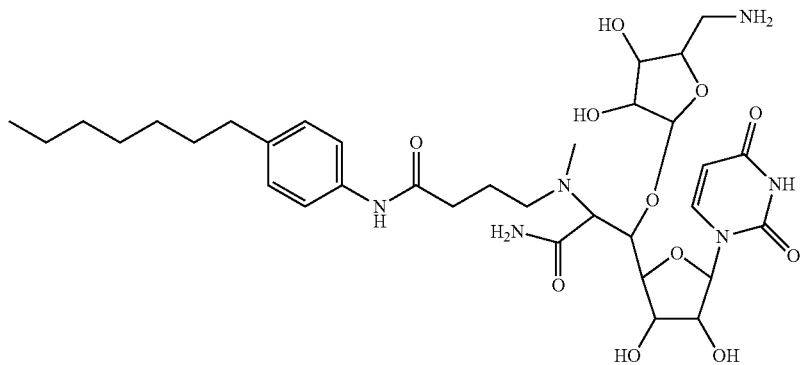 [SMILES: CCCCCCCc1ccc(NC(=O)CCCN(C)C(C(N)=O)C(OC2OC(CN)C(O)C2O)C2OC(n3ccc(=O)[nH]c3=O)C(O)C2O)cc1]

or a pharmaceutically acceptable salt thereof.

In still another embodiment, R¹ is piperazine-O-PhCF₃; X is —NH—; and Y is —CH₂—.

In yet another embodiment, the compound of Formula I is

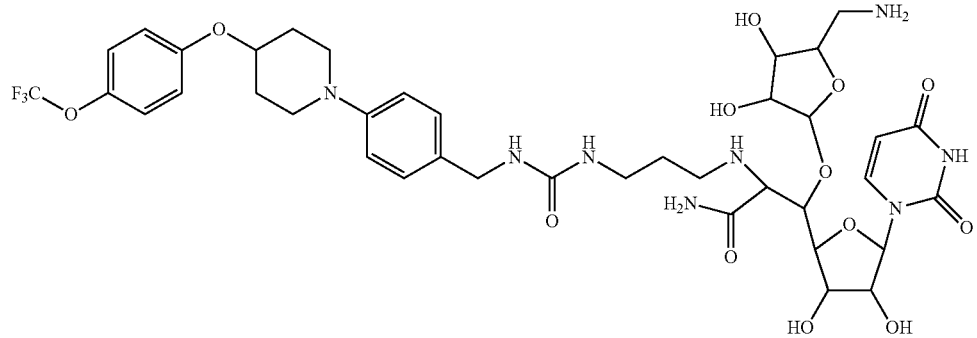 [SMILES: NCC1OC(OC(C(NCCCNC(=O)NCc2ccc(N3CCC(Oc4ccc(OC(F)(F)F)cc4)CC3)cc2)C(N)=O)C2OC(n3ccc(=O)[nH]c3=O)C(O)C2O)C(O)C1O]

or a pharmaceutically acceptable salt thereof.

In an embodiment, the compound of Formula I is

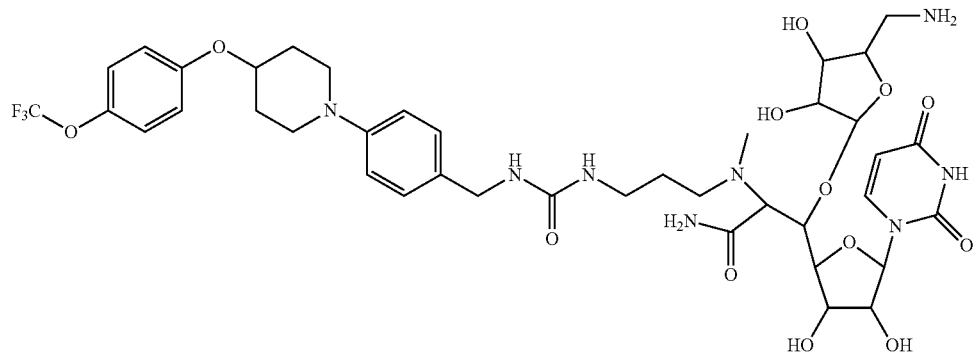 [SMILES: CN(CCCNC(=O)NCc1ccc(N2CCC(Oc3ccc(OC(F)(F)F)cc3)CC2)cc1)C(C(N)=O)C(OC1OC(CN)C(O)C1O)C1OC(n2ccc(=O)[nH]c2=O)C(O)C1O]

or a pharmaceutically acceptable salt thereof.

In another aspect, provided herein are pharmaceutical compositions comprising any of the compounds described herein, or a pharmaceutically acceptable salt thereof, together with a pharmaceutically acceptable carrier.

In yet another aspect, provided herein are methods of inhibiting dolichyl-phosphate N-acetylglucosaminephosphotransferase (DPAGT1) in an individual in need thereof, comprising administering to the individual a therapeutically effective amount of any of the compounds or compositions described herein.

In an embodiment of the methods, the method further comprises administering a second compound. In another embodiment, the second compound is selected from the group consisting of taxol, tunicamycin, and gemcitabine.

In an embodiment of these combination therapies, the compound and the additional therapeutic agent are co-formulated. In another embodiment, the compound and the additional therapeutic agent are co-administered.

In another embodiment of these combination therapies, administering a compound provided herein allows for administering of the one additional therapeutic agent at a lower dose or frequency as compared to the administering of the at least one additional therapeutic agent alone that is required to achieve similar results in inhibiting DPAGT1 in an individual in need thereof.

In still another aspect, provided herein is a method of treating an infection in an individual in need thereof, comprising administering to the individual a therapeutically effective amount of any of the compounds or compositions described herein.

In an embodiment of the methods, the infection is a bacterial infection. In another embodiment, the bacterial infection is caused by bacteria selected from the group consisting of *Clostridium difficile*, *Bacillus subtilis*, *Clostridium perfringens*, and *Mycobacterium smegmatis*. In yet another embodiment, the bacterial infection is caused by *Clostridium difficile*.

In an aspect, provided herein is a method of treating cancer in an individual in need thereof, comprising administering to the individual a therapeutically effective amount any of the compounds or compositions described herein.

In an embodiment of the methods, the cancer is cervical cancer, colon cancer, ovarian cancer, breast cancer, pancreatic cancer, carcinoma, or adenocarcinoma.

In another aspect, provided herein is a process for preparing a composition comprising a compound of Formula III:

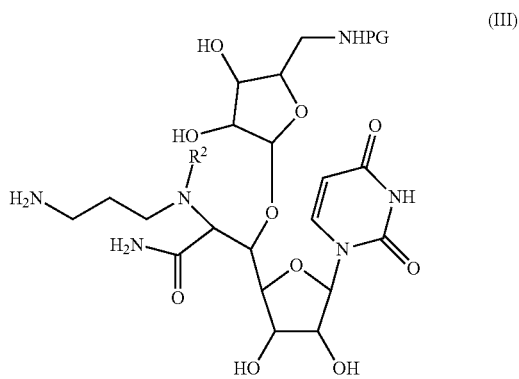

comprising reacting a compound of Formula II:

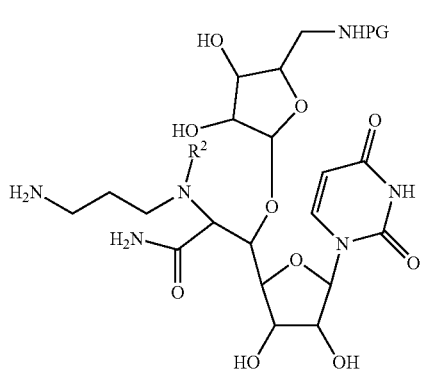

with a copper reagent in the presence of a solvent and a base, and further reacting the compound of Formula II with a protecting group reagent
wherein
$R^2$ is H or $C_1$-$C_6$ alkyl; and
PG is a protecting group selected from the group consisting of acetyl (Ac), benzyl (Bn), tert-butyloxycarbonyl (Boc), benzoyl (Bz), carboxybenzyl (Cbz), carbamate, 3,4-dimethoxy-benzyl (DMPM), 9-fluorenylmethyloxycarbonyl (Fmoc), p-methoxybenzyl carbonyl (Moz), 4-nitrobenzylsulfonyl (Nos), p-methoxybenzyl (PMB), p-methoxyphenyl (PMP), 4-toluenesulfonyl (Tos), and trichloroethyl chloroformate (Troc).

In an embodiment, the copper reagent is selected from the group consisting of $CuSO_4$, $Cu(OAc)_2$, and $CuCl_2$. In another embodiment, the copper reagent is $Cu(OAc)_2$.

In yet another embodiment, the base is sodium hydroxide. In still another embodiment, the solvent is a mixture of dimethylformamide, methanol, and water. In an embodiment, PG is tert-butyloxycarbonyl (Boc) and the protecting group reagent is di-tert-butyl dicarbonate ($Boc_2O$). In another embodiment, PG is carboxybenzyl (Cbz) and the protecting group reagent is benzyl chloroformate or is N-(benzyloxycarbonyloxy)succinimide.

In yet another aspect, provided herein is a process for preparing a composition comprising a compound of Formula V:

comprising reacting a compound of Formula III:

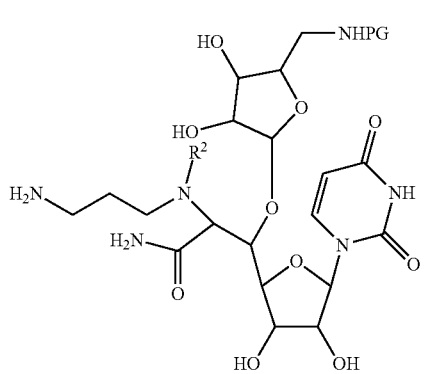

with a compound of Formula IV:

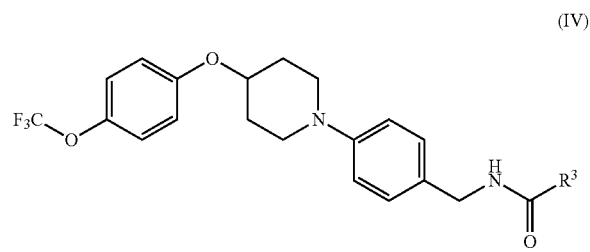

under basic conditions in a solvent
wherein
$R^2$ is H or $C_1$-$C_6$ alkyl;
PG is a protecting group selected from the group consisting of acetyl (Ac), benzyl (Bn), tert-butyloxycarbonyl (Boc), benzoyl (Bz), carboxybenzyl (Cbz), carbamate, 3,4-dimethoxy-benzyl (DMPM), 9-fluorenylmethyloxycarbonyl (Fmoc), p-methoxybenzyl carbonyl (Moz), 4-nitrobenzylsulfonyl (Nos), p-methoxybenzyl (PMB), p-methoxyphenyl (PMP), 4-toluenesulfonyl (Tos), and trichloroethyl chloroformate (Troc); and
$R^3$ is selected from the group consisting of $OC_1$-$C_4$ alkyl, tosylate, mesylate, iodide, bromide, chloride, imidazole, and triflate.

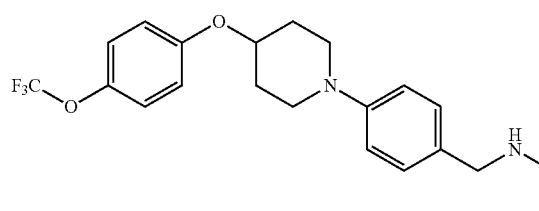
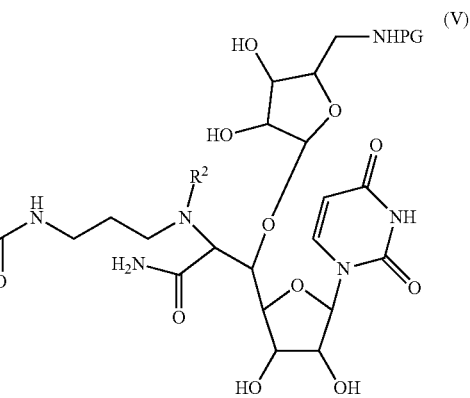

In an embodiment, $R^3$ is imidazole. In another embodiment, the base is triethylamine. In yet another embodiment, the solvent is a mixture of dimethylformamide and dichloromethane.

In still another aspect, provided herein is a process for preparing a composition comprising a compound of Formula I:

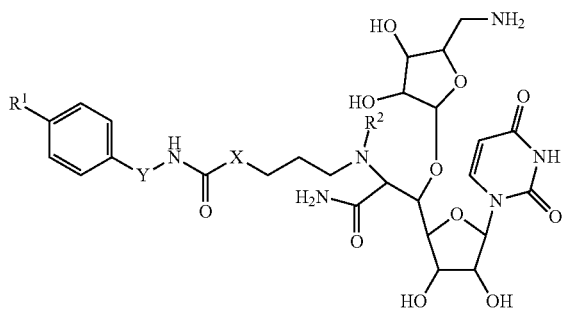
(I)

comprising treating a compound of Formula V:

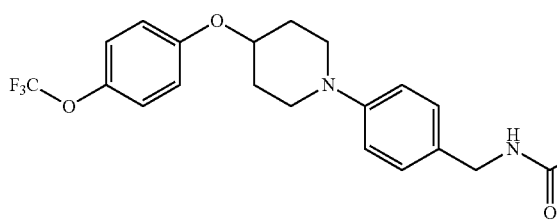
(V)

with an acid in a solvent
wherein:
$R^1$ is piperazine-O-Ph, wherein Ph is optionally substituted with $C_1$-$C_4$ alkyl or $OC_1$-$C_4$ alkyl, wherein $OC_1$-$C_4$ alkyl is optionally further substituted with 1, 2, or 3 halo;
$R^2$ is H or $C_1$-$C_6$ alkyl;
X is —NH—;
Y is —$(CH_2)_n$—;
PG is a protecting group selected from the group consisting of acetyl (Ac), benzyl (Bn), tert-butyloxycarbonyl (Boc), benzoyl (Bz), carboxybenzyl (Cbz), carbamate, 3,4-dimethoxy-benzyl (DMPM), 9-fluorenylmethyloxycarbonyl (Fmoc), p-methoxybenzyl carbonyl (Moz), 4-nitrobenzylsulfonyl (Nos), p-methoxybenzyl (PMB), p-methoxyphenyl (PMP), 4-toluenesulfonyl (Tos), and trichloroethyl chloroformate (Troc); and
n is 1.

In an embodiment, the acid is trifluoroacetic acid. In another embodiment, the solvent is dichloromethane.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Figure 1:
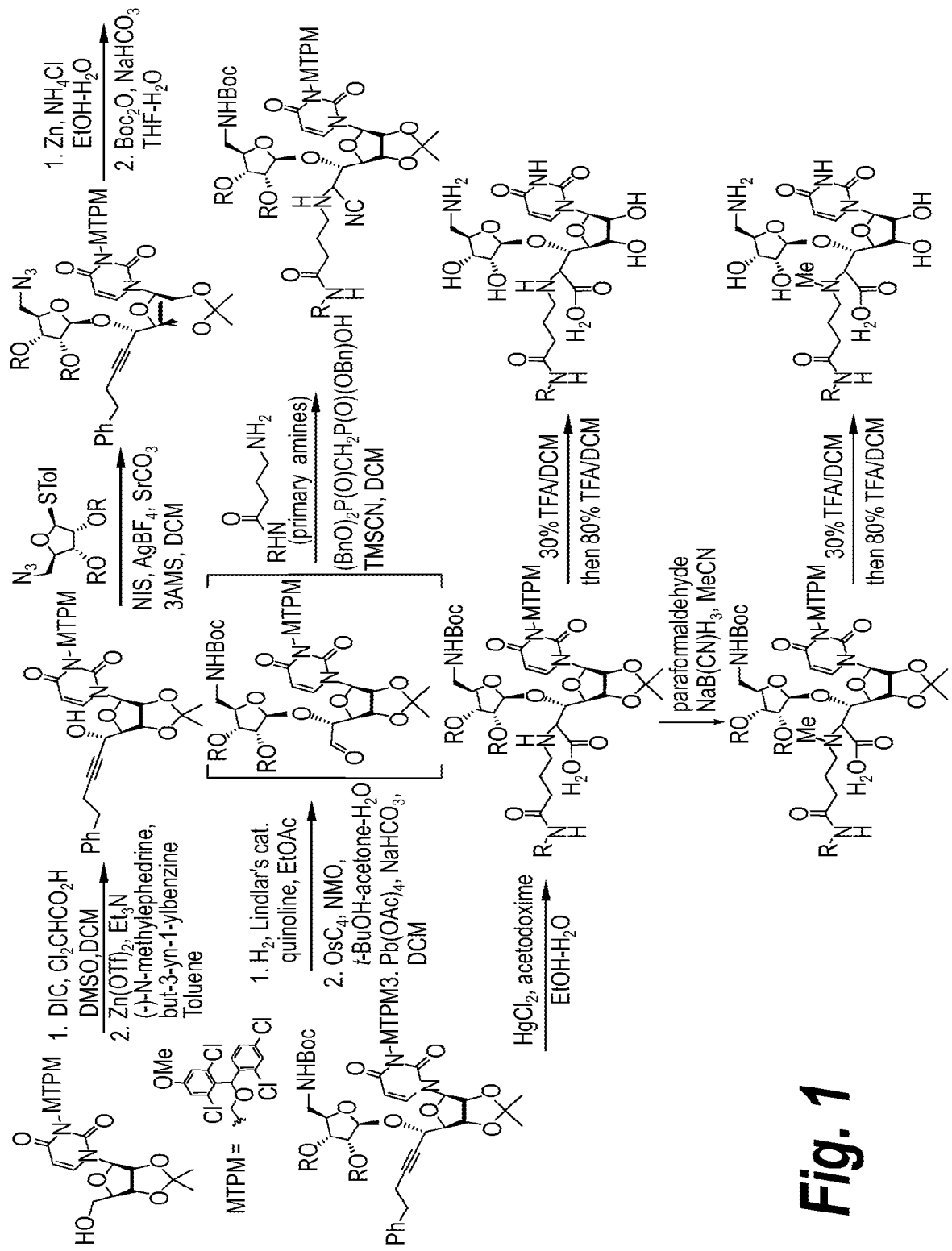
FIG. 1 shows a general synthetic method for preparing the amide-containing compounds provided herein.
Figure 2:
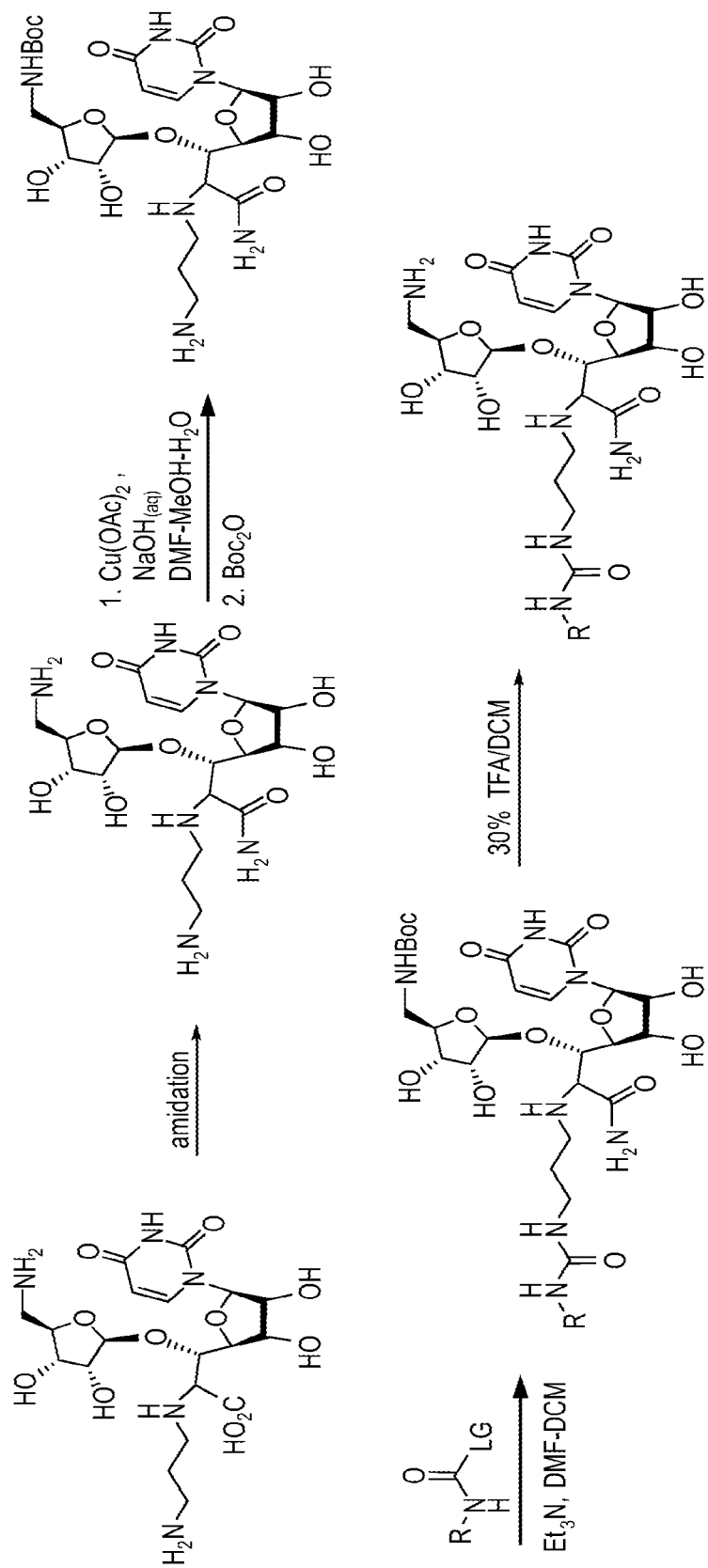
FIG. 2 shows a general synthetic method for preparing the urea-containing compounds provided herein.

Provided herein are compounds, and pharmaceutically acceptable salts thereof, that are useful in the treatment of cancer or a bacterial infection in an individual in need thereof.

In a non-limiting aspect, these compounds can inhibit DPAGT1. In a particular embodiment, the compounds provided herein are considered DPAGT1 inhibitors. As such, in one aspect, the compounds provided herein are useful in the treatment of cancer or bacterial infections in an individual by acting as a DPAGT1 inhibitor.

DPAGT1, which belongs to the glycosyltransferase family 4, is an integral membrane protein localized in the ER that catalyzes the transformation from UDP-GlcNAc to N-acetyl-D-glucosaminyl-diphosphodolichol with dolichyl phosphate. Anchored N-acetyl-D-glucosaminyl-diphosphodolichol in the ER membrane is modified by sequential glycosyltransferases to form dolichol-linked oligosaccharide precursors that are transferred to selected asparagine residues (N-X-S or N-X-T sequences) of polypeptide chains by oligosaccharyltransferase (OST).

Antibacterial Treatment

*Clostridium difficile* infection (CDI) has been declared a public health threat since 2013. CDI causes diarrhea, inflammation of the gut and, in some cases, death. Approximately 250,000 people are hospitalized in the U.S. every year from CDI. The infective form of *C. difficile* is the spore and its germination is the first committed step in CDI onset. *C. difficile* is found in abundance in the environment and colonizes the gut where it produces toxins that cause *C. difficile*-associated diarrhea (CDAD). Frequently, antibiotic therapy for CDI with broad-spectrum antibiotic(s) has the adverse effect on disrupting the normal balance of the gut flora, causing *C. difficile* colitis. Antibiotic treatment of CDI is difficult due both to antibiotic resistance and physiological factors of the bacteria (e.g. spore formation, protective effects of the pseudomembrane). There are a limited number of drugs available for the treatment of CDAD.

Interestingly, certain antibiotic agents have exhibited strong bacteriostatic activity against *Mycobacterium tuberculosis* by targeting the bacterial phosphotransferases (MurX and WecA). WecA enzyme inhibitors have the potential to interfere with a human homologue, DPAGT1. Thus, it was observed strong inhibition of DPAGT1 causes cytotoxicity in many bacterial strains.

Cancer Treatment

β-Catenin, encoded by the CTNNB1 gene (a proto-oncogene), is a multifunctional protein that regulates and coordinates cell-cell adhesion and gene transcription. β-Catenin is a crucial transcriptional factor in highly conserved Wnt (Wingless-Int)/β-catenin signaling pathway, and plays an important role in embryonic development and carcinogenesis (Vargas, D. A. et al. (2016) PLOS Computational Biol. 12: e1005007). In normal cells, β-catenin concentration is low because of proteasome degradation. The mutations of β-catenin are found in a variety of cancers including ovarian cancer, breast cancer, cancerous liver tumors, colorectal cancer, lung cancer and glioblastoma (Nita-Lazar M. et al. (2009) Cancer Res. 316: 1871-1884). In these cancer cells, the mutations are observed in the β-transducin repeat-containing protein (β-TrCP) binding motif that facilitate ubiquitinylation, making degradation of β-catenin difficult. It causes a high level of β-catenin in the cytoplasm, which is translocated to the nucleus and drives transcription of the target genes including Wnt genes. An alternative function of β-catenin and the other member of the catenin protein family (α-catenin, and γ-catenin (plakoglobin)) are linked to E-cadherin, a calcium-dependent cell-cell adhesion molecule that responsible for intercellular cell-adhesions. One of the N-glycosylation targets of DPAGT1 is E-cadherin. Overexpression of β-catenin causes a high level of DPAGT1 expression, leading to abnormal modification of E-cadherin. Numerous studies concluded that the Wnt/β-catenin signaling pathway regulates the metabolic pathway of protein N-glycosylation by targeting DPAGT1 expression. Dysregulation of DPAGT1 causes disturbances in intercellular adhesion in oral cancer (Nita-Lazar et al., 2009). Based on these observed biological processes, inhibition of DPAGT1 may induce the loss of cell-cell adhesion and metathesis, and trigger an apoptotic pathway (Lim, E. et al. (2015) Apoptosis, 8: 1087-1098). Only a few DPAGT1 inhibitors have been identified to date. Therefore, inhibition of DPAGT1 may very well be the "Achilles' heel" of the biosynthesis of essential N-glycan in certain cancers.

Definitions

Listed below are definitions of various terms used to describe this invention. These definitions apply to the terms as they are used throughout this specification and claims, unless otherwise limited in specific instances, either individually or as part of a larger group. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated or caused by the state, disorder or disease being treated. In certain embodiments, the treatment comprises bringing into contact with DPAGT1 an effective amount of a compound of the invention for conditions related to cancers and bacterial infections.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example, in Remington's Pharmaceutical Sciences (Genaro, Ed., Mack Publishing Co., 1985, Easton, PA), which is incorporated herein by reference.

As used herein, "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination of agents described herein display a synergistic effect. The term "synergistic effect" and phrase "synergy" as used herein, refer to the action of two agents such as, for example, a DPAGT1 inhibitor and a second compound (e.g. Tunicamycin), producing an effect, for example, inhibiting bacterial growth, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55.

The term "DPAGT1" as used herein, refers to dolichyl-phosphate N-acetylglucosamine-phosphotransferase, which is the first committed enzyme for N-glycan biosynthesis.

As used herein, the term "alkyl," by itself or as part of another substituent means, unless otherwise stated, a straight or branched chain hydrocarbon having the number of carbon atoms designated (i.e., $C_1$-$C_{10}$-alkyl means an alkyl having one to ten carbon atoms) and includes straight and branched chains. In an embodiment, $C_1$-$C_{10}$ alkyl groups are provided herein. Examples include methyl, ethyl, propyl, isopropyl, butyl, isobutyl, tert butyl, pentyl, neopentyl, hexyl, heptyl, octyl, nonyl, and decyl.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_4$ alkoxy groups are provided herein.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "Ph" means phenyl, which is a $C_6$ aryl system. The term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms.

It is to be understood that if an aryl moiety may be bonded or otherwise attached to a designated moiety through differing ring atoms (i.e., shown or described without denotation of a specific point of attachment), then all possible points are intended.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

In an aspect, provided herein are compounds of Formula I:

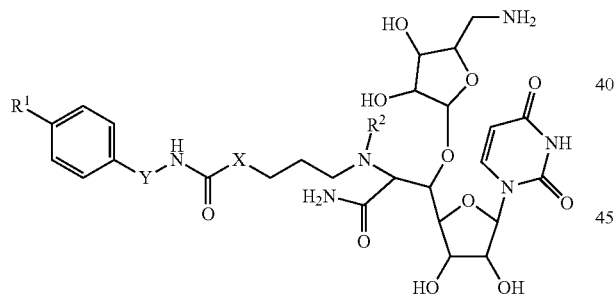

(I)

or a pharmaceutically acceptable salt thereof;

wherein $R^1$ is $C_1$-$C_{10}$ alkyl or piperazine-O-Ph, wherein Ph is optionally substituted with $C_1$-$C_4$ alkyl or $OC_1$-$C_4$ alkyl, wherein $C_1$-$C_4$ alkyl or $OC_1$-$C_4$ alkyl is optionally further substituted with 1, 2, or 3 halo;

$R^2$ is H or $C_1$-$C_6$ alkyl;

X is selected from the group consisting of absent, —(CH$_2$)$_m$—, and —NH—;

Y is absent or —(CH$_2$)$_n$—; and m and n are, independently at each occurrence, 1, 2, or 3.

In an embodiment of Formula I, X is absent. In another embodiment of Formula I, Y is —CH$_2$—. In yet another embodiment of Formula I, $R^1$ is piperazine-O-Ph, wherein Ph is optionally substituted with $C_1$-$C_4$ alkyl or $OC_1$-$C_4$ alkyl, wherein $C_1$-$C_4$ alkyl or $OC_1$-$C_4$ alkyl is optionally further substituted with 1, 2, or 3 halo. In still another embodiment of Formula I, $R^1$ is $C_6$-$C_8$ alkyl. In an embodiment of Formula I, $R^1$ is $C_7$ alkyl. In another embodiment of Formula I, X is —NH—. In yet another embodiment of Formula I, Y is absent. In still another embodiment of Formula I, $R^1$ is piperazine-O-Ph-CF$_3$. In an embodiment of Formula I, $R^2$ is $C_1$ alkyl. In an embodiment of Formula I, $R^2$ is H.

In an embodiment, $R^1$ is

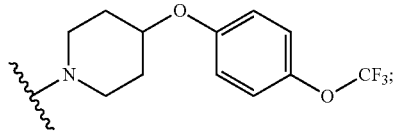 [SMILES: *N1CCC(Oc2ccc(OC(F)(F)F)cc2)CC1]

X is absent; and Y is —CH$_2$—.

In another embodiment, the compound of Formula I is

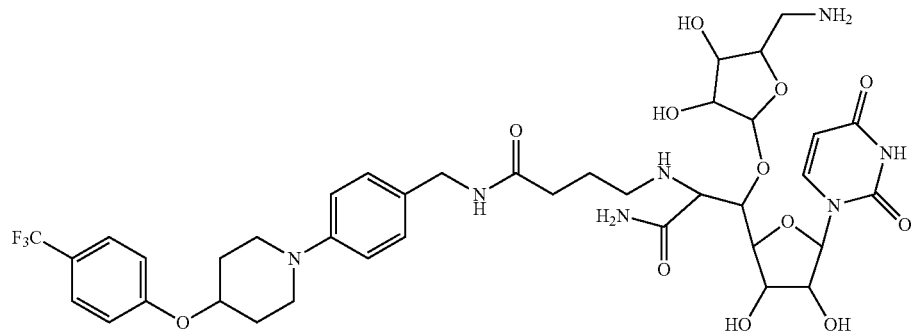 [SMILES: NCC1OC(OC(C(NCCCC(=O)NCc2ccc(N3CCC(Oc4ccc(C(F)(F)F)cc4)CC3)cc2)C(N)=O)C2OC(n3ccc(=O)[nH]c3=O)C(O)C2O)C(O)C1O]

or a pharmaceutically acceptable salt thereof.

In yet another embodiment, the compound of Formula I, or a pharmaceutically acceptable salt thereof, has the following stereochemistry:

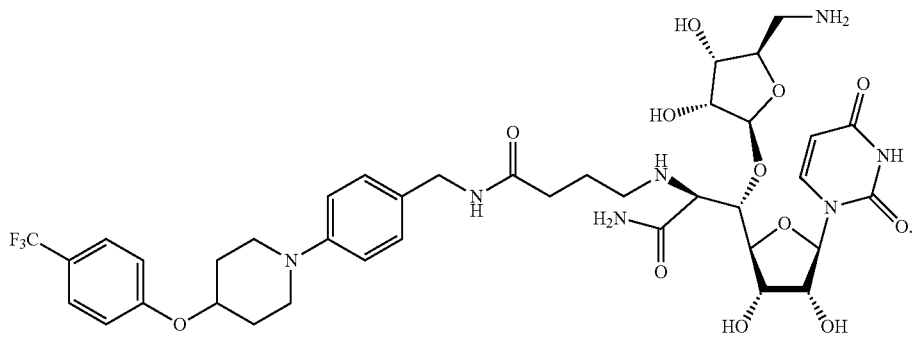

In still another embodiment, the compound of Formula I is

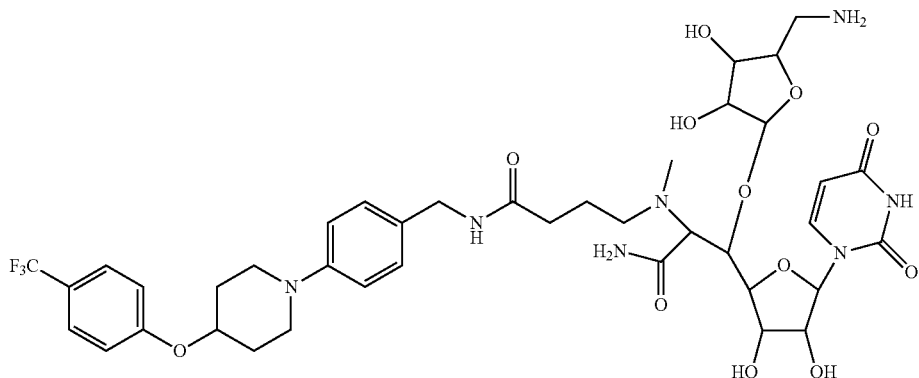 [SMILES: CN(CCCC(=O)NCc1ccc(N2CCC(Oc3ccc(C(F)(F)F)cc3)CC2)cc1)C(C(N)=O)C(OC1OC(CN)C(O)C1O)C1OC(n2ccc(=O)[nH]c2=O)C(O)C1O]

or a pharmaceutically acceptable salt thereof.

In an embodiment, the compound of Formula I, or a pharmaceutically acceptable salt thereof, has the following stereochemistry:

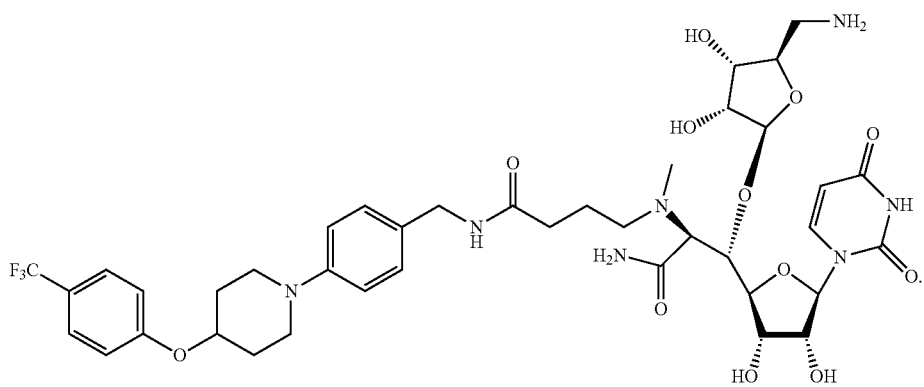

In another embodiment, $R^1$ is $C_7$ alkyl; X is absent; and Y is absent.

In yet another embodiment, the compound of Formula I is

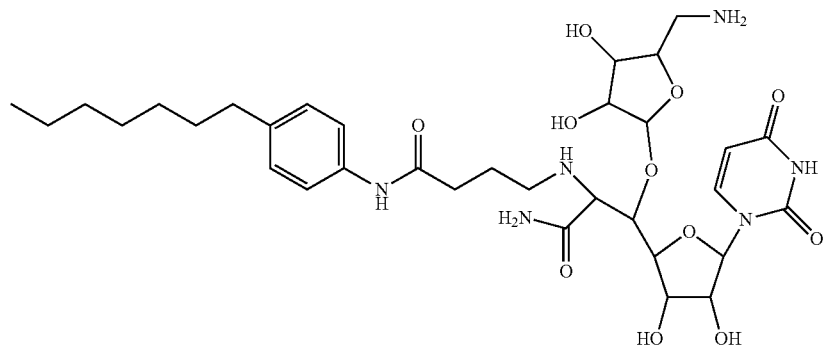 [SMILES: CCCCCCCc1ccc(NC(=O)CCCNC(C(N)=O)C(OC2OC(CN)C(O)C2O)C2OC(n3ccc(=O)[nH]c3=O)C(O)C2O)cc1]

or a pharmaceutically acceptable salt thereof.

In still another embodiment, the compound of Formula I, or a pharmaceutically acceptable salt thereof, has the following stereochemistry:

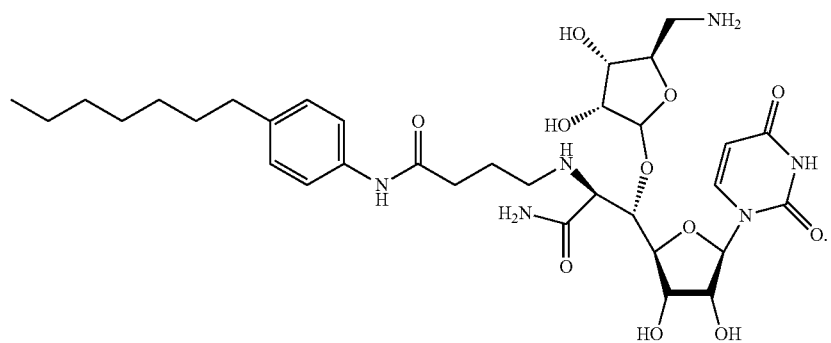

In an embodiment, the compound of Formula I is

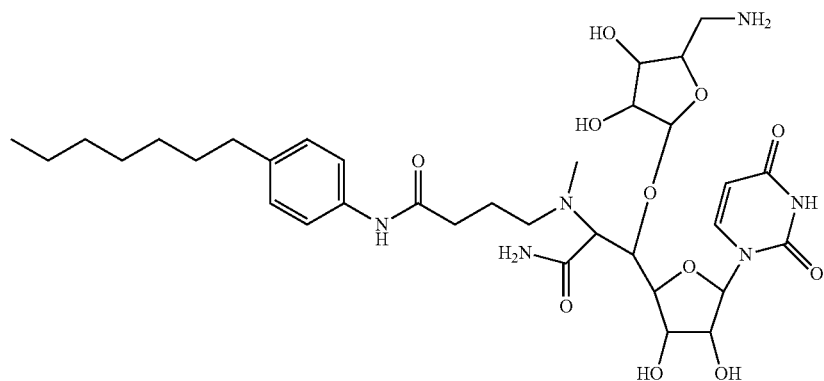 [SMILES: CCCCCCCc1ccc(NC(=O)CCCN(C)C(C(N)=O)C(OC2OC(CN)C(O)C2O)C2OC(n3ccc(=O)[nH]c3=O)C(O)C2O)cc1]

or a pharmaceutically acceptable salt thereof.

In another embodiment, the compound of Formula I, or a pharmaceutically acceptable salt thereof, has the following stereochemistry:

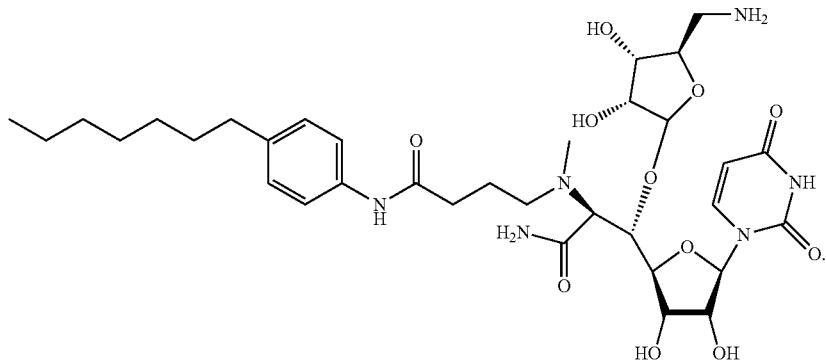

In yet another embodiment, R¹ is

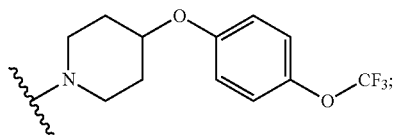 [SMILES: *N1CCC(Oc2ccc(OC(F)(F)F)cc2)CC1]

X is —NH—; and Y is —CH₂—.

In still another embodiment, the compound of Formula I is

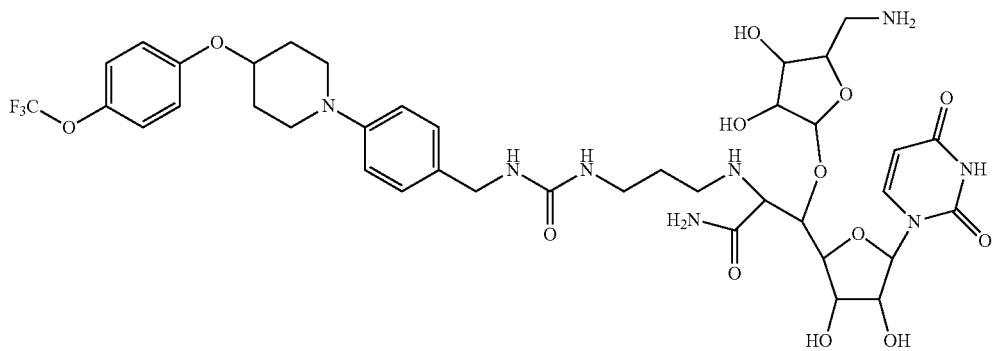 [SMILES: NCC1OC(OC(C(NCCCNC(=O)NCc2ccc(N3CCC(Oc4ccc(OC(F)(F)F)cc4)CC3)cc2)C(N)=O)C2OC(n3ccc(=O)[nH]c3=O)C(O)C2O)C(O)C1O]

or a pharmaceutically acceptable salt thereof.

In an embodiment, the compound of Formula I, or a pharmaceutically acceptable salt thereof, has the following stereochemistry:

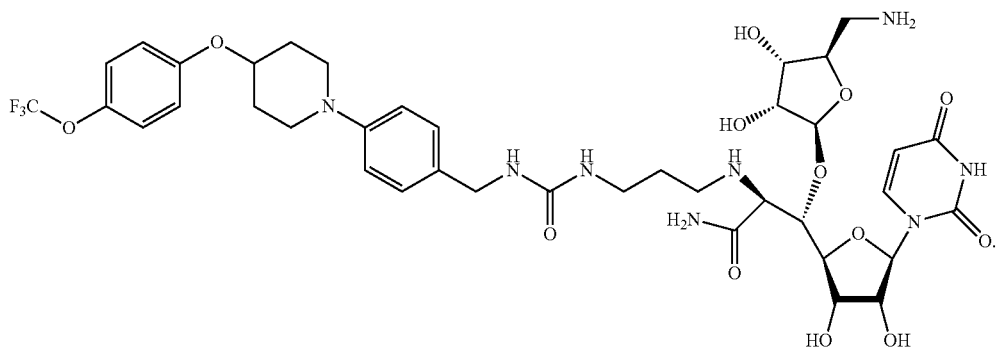

In another embodiment, the compound of Formula I is

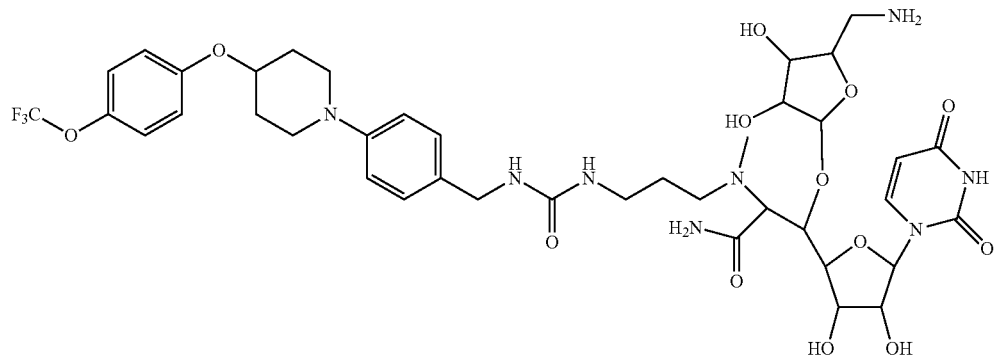 [SMILES: CN(CCCNC(=O)NCc1ccc(N2CCC(Oc3ccc(OC(F)(F)F)cc3)CC2)cc1)C(C(N)=O)C(OC1OC(CN)C(O)C1O)C1OC(n2ccc(=O)[nH]c2=O)C(O)C1O]

or a pharmaceutically acceptable salt thereof.

In yet another embodiment, the compound of Formula I, or a pharmaceutically acceptable salt thereof, has the following stereochemistry:

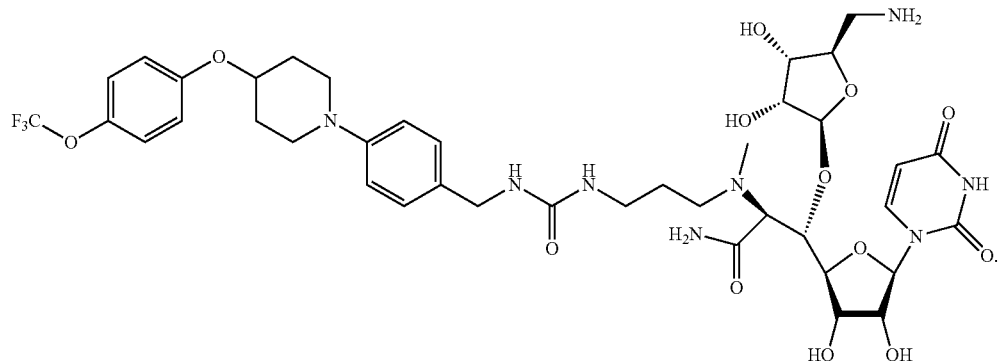

In an embodiment, the compound of Formula I is selected from the compounds of Table A, or pharmaceutically acceptable salts thereof:

TABLE A

| Compound Number | Structure |
|---|---|
| 8 | 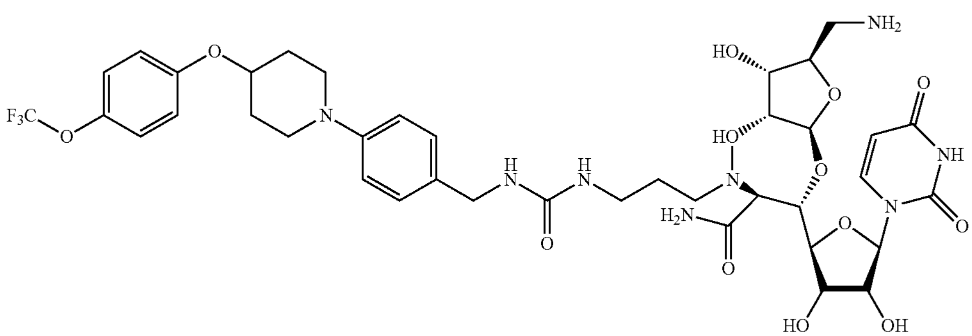 |

TABLE A-continued

| Compound Number | Structure |
|---|---|
| 9 | 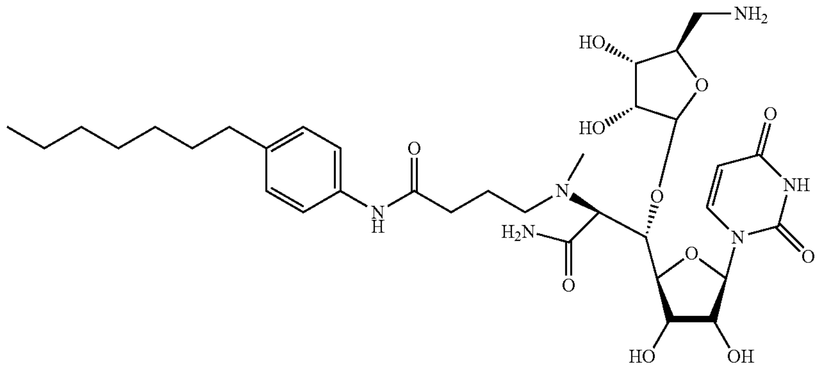 |
| 10 | 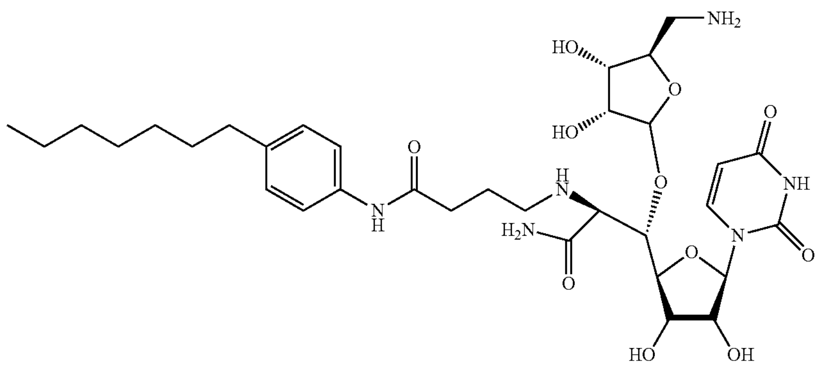 |
| 11 | 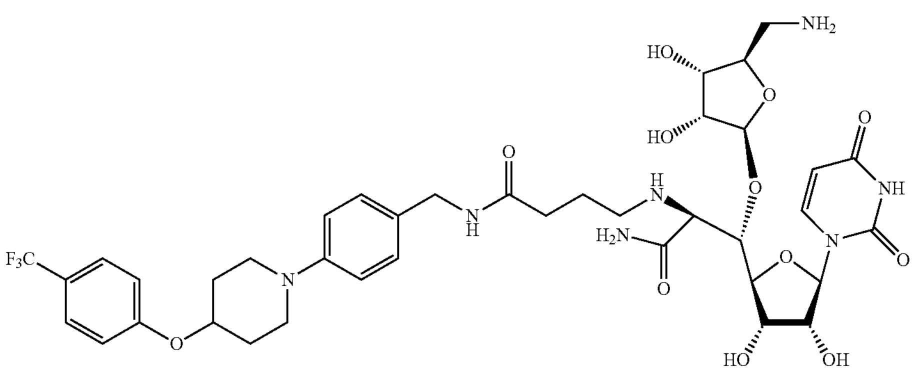 |
| 12 | 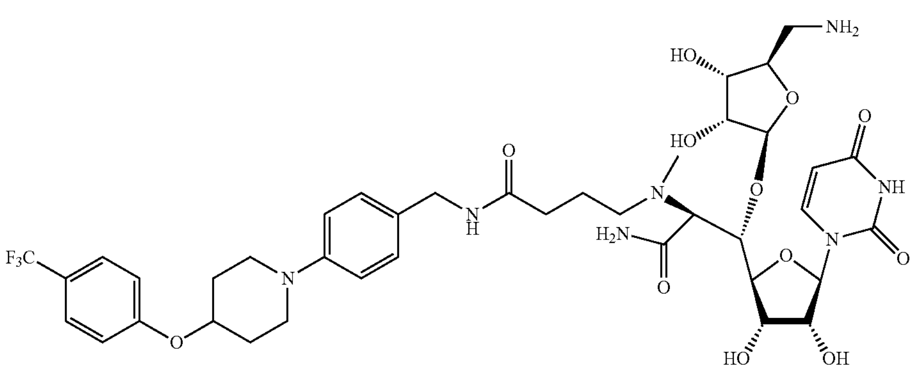 |

In an aspect, provided herein are pharmaceutical compositions comprising any of the compounds described herein, or a pharmaceutically acceptable salt thereof, together with a pharmaceutically acceptable carrier.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a $^{2}H$ (i.e., deuterium) isotope.

In still another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by the Formula described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds of the invention can be used in a method of treating a disease or condition in an individual, said method comprising administering to the subject a compound of the invention, or a pharmaceutical composition comprising a compound of the invention.

In one aspect, the invention provides a method of selectively inhibiting DPAGT1 in an individual in need thereof, comprising administering to the subject any of the compounds of compositions described herein.

In another aspect, the invention provides a method of inhibiting DPAGT1 in an individual comprising administering to the individual any of the compounds of compositions described herein.

In an embodiment, the method comprises administering a second compound. In certain embodiments, the second compound is selected from the group consisting of taxol, tunicamycin, and gemcitabine.

In another embodiment, the method of inhibiting DPAGT1 comprises administering a compound of Formula I:

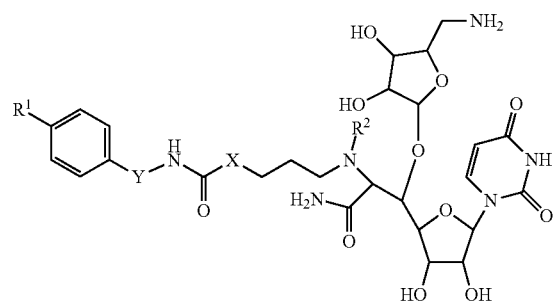

(I)

or a pharmaceutically acceptable salt thereof;
wherein
$R^{1}$ is $C_{1}$-$C_{10}$ alkyl or piperazine-O-Ph, wherein Ph is optionally substituted with $C_{1}$-$C_{4}$ alkyl or $OC_{1}$-$C_{4}$ alkyl, wherein $C_{1}$-$C_{4}$ alkyl or $OC_{1}$-$C_{4}$ alkyl is optionally further substituted with 1, 2, or 3 halo;
$R^{2}$ is H or $C_{1}$-$C_{6}$ alkyl;
X is selected from the group consisting of absent, —$(CH_{2})_{m}$—, and —NH—;
Y is absent or —$(CH_{2})_{n}$—; and
m and n are, independently at each occurrence, 1, 2, or 3.

In yet another embodiment, the method of inhibiting DPAGT1 comprises administering Compound 11:

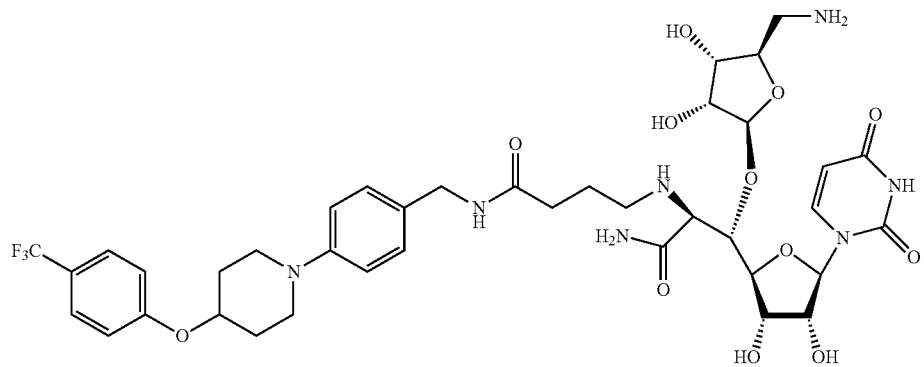

or a pharmaceutically acceptable salt thereof.

In yet another aspect, the invention provides a method of treating an infection in an individual in need thereof, comprising administering to the individual a therapeutically effective amount of any of the compounds or compositions described herein.

In an embodiment, the bacterial infection is caused by bacteria selected from the group consisting of *Clostridium difficile, Bacillus subtilis, Clostridium perfringens,* and *Mycobacterium smegmatis*. In another embodiment, the bacterial infection is caused by *Clostridium difficile*.

In another embodiment, the method of treating an infection comprises administering a compound of Formula I:

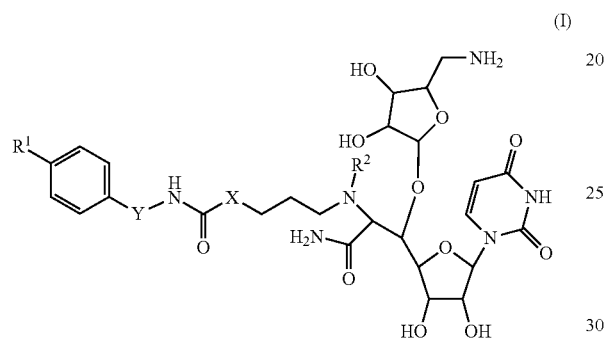

(I)

or a pharmaceutically acceptable salt thereof;
wherein
$R^1$ is $C_1$-$C_{10}$ alkyl or piperazine-O-Ph, wherein Ph is optionally substituted with $C_1$-$C_4$ alkyl or $OC_1$-$C_4$ alkyl, wherein $C_1$-$C_4$ alkyl or $OC_1$-$C_4$ alkyl is optionally further substituted with 1, 2, or 3 halo;
$R^2$ is H or $C_1$-$C_6$ alkyl;
X is selected from the group consisting of absent, —(CH$_2$)$_m$—, and —NH—;
Y is absent or —(CH$_2$)$_n$—; and
m and n are, independently at each occurrence, 1, 2, or 3.

In yet another embodiment, the method of treating an infection comprises administering Compound 11:

In still another aspect, the invention provides a method of treating cancer in an individual in need thereof, comprising administering to the individual a therapeutically effective amount of any of the compounds or compositions described herein.

In an embodiment, the cancer is cervical cancer, colon cancer, ovarian cancer, breast cancer, pancreatic cancer, carcinoma, or adenocarcinoma.

In another embodiment, the method of treating cancer comprises administering a compound of Formula I:

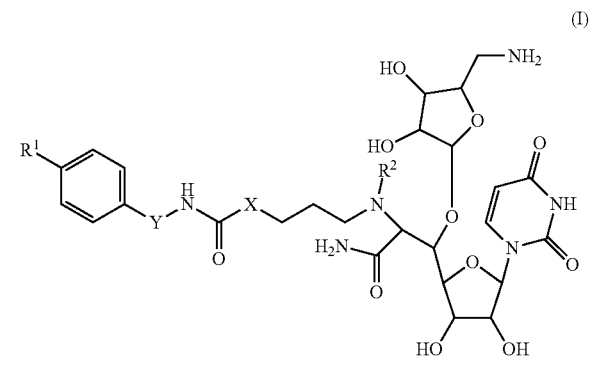

(I)

or a pharmaceutically acceptable salt thereof;
wherein
$R^1$ is $C_1$-$C_{10}$ alkyl or piperazine-O-Ph, wherein Ph is optionally substituted with $C_1$-$C_4$ alkyl or $OC_1$-$C_4$ alkyl, wherein $C_1$-$C_4$ alkyl or $OC_1$-$C_4$ alkyl is optionally further substituted with 1, 2, or 3 halo;
$R^2$ is H or $C_1$-$C_6$ alkyl;
X is selected from the group consisting of absent, —(CH$_2$)$_m$—, and —NH—;
Y is absent or —(CH$_2$)$_n$—; and
m and n are, independently at each occurrence, 1, 2, or 3.

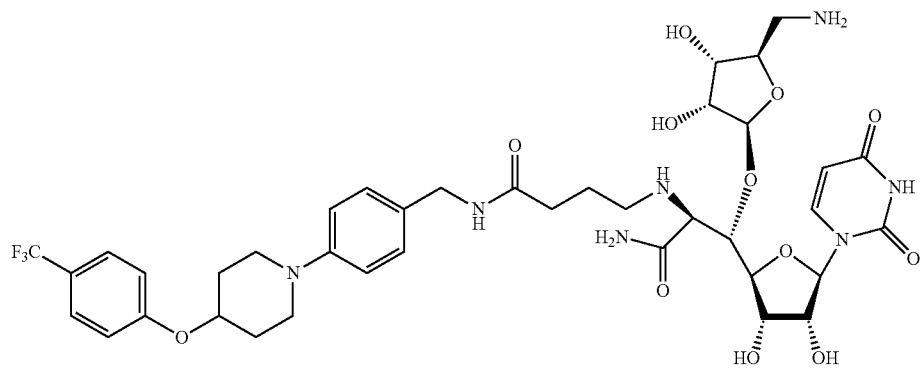

or a pharmaceutically acceptable salt thereof.

In yet another embodiment, the method of treating cancer comprises administering Compound 11:

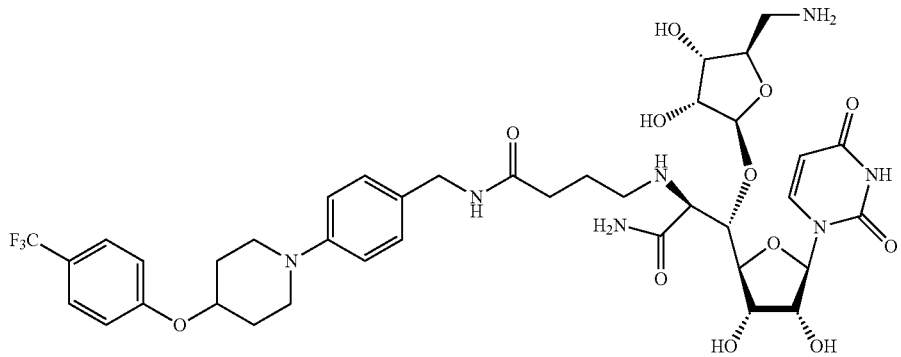

or a pharmaceutically acceptable salt thereof.

Processes for Preparing

The present invention provides, inter alia, processes of preparing compounds of Formula I, which are useful as DPAGT1 inhibitors.

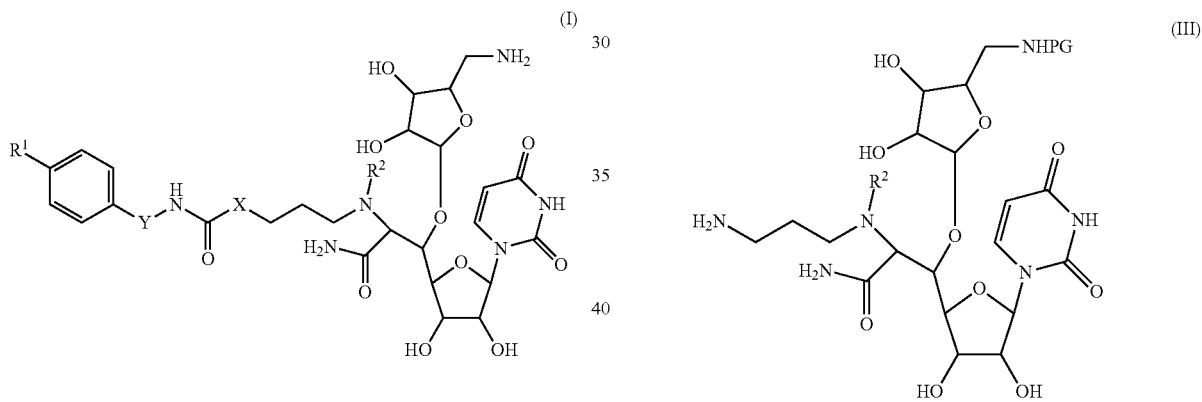

In an aspect, the invention provides processes for preparing intermediate compounds useful for producing compounds of Formula I. In still another aspect, the present invention provides enantiomerically enriched compositions of any of the intermediates described herein, provided the intermediates have at least one chiral center.

The processes described herein include processes for preparing compounds and intermediates and compositions thereof, wherein $R^1$ is selected from $C_1$-$C_{10}$ alkyl and piperazine-O-Ph, wherein Ph is optionally substituted with $C_1$-$C_4$ alkyl or $OC_1$-$C_4$ alkyl, wherein $C_1$-$C_4$ alkyl or $OC_1$-$C_4$ alkyl is optionally further substituted with 1, 2, or 3 halo. In some embodiments, $R^1$ is piperazine-O-PhCF$_3$. In some embodiments, $R^1$ is $C_5$-$C_8$ alkyl. In another embodiment, $R^1$ is $C_7$ alkyl. In some embodiments, $R^1$ is piperazine-O-PhCF$_3$. In some embodiments, $R^2$ is selected from H or $C_1$-$C_6$ alkyl. In some embodiments, $R^2$ is H. In some embodiments, $R^2$ is $C_1$-$C_6$ alkyl. In some embodiments, $R^2$ is $C_1$ alkyl. In some embodiments, X is selected from the group consisting of absent, —(CH$_2$)$_m$—, and —NH—. In some embodiments, X is absent. In some embodiments, X is —NH—. In some embodiments, Y is absent or —(CH$_2$)$_n$—. In some embodiments, Y is —CH$_2$—. In some embodiments, Y is absent. In some embodiments, m and n are, independently at each occurrence, 1, 2, or 3. In some embodiments, m is 1. In some embodiments, n is 1. These embodiments can apply to any of the intermediates or compounds described herein in any of the processes, as appropriate.

In an aspect, provided herein is a process for preparing a composition comprising a compound of Formula III:

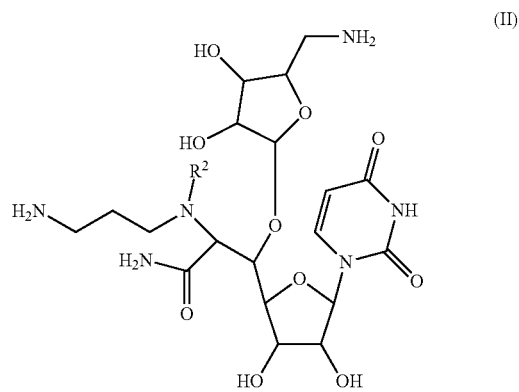

comprising reacting a compound of Formula II:

(II)

with a copper reagent in the presence of a solvent and a base, and further reacting the compound of Formula II with a protecting group reagent wherein R² is H or C₁-C₆ alkyl; and PG is a protecting group selected from the group consisting of acetyl (Ac), benzyl (Bn), tert-butyloxycarbonyl (Boc), benzoyl (Bz), carboxybenzyl (Cbz), carbamate, 3,4-dimethoxy-benzyl (DMPM), 9-fluorenylmethyloxycarbonyl (Fmoc), p-methoxybenzyl carbonyl (Moz), 4-nitrobenzylsulfonyl (Nos), p-methoxybenzyl (PMB), p-methoxyphenyl (PMP), 4-toluenesulfonyl (Tos), and trichloroethyl chloroformate (Troc).

In an embodiment, the copper reagent is selected from the group consisting of CuSO₄, Cu(OAc)₂, and CuCl₂. In another embodiment, the copper reagent is Cu(OAc)₂.

In yet another embodiment, the base is sodium hydroxide. In still another embodiment, the solvent is a mixture of dimethylformamide, methanol, and water. In an embodiment, PG is tert-butyloxycarbonyl (Boc) and the protecting group reagent is di-tert-butyl dicarbonate (Boc₂O). In another embodiment, PG is carboxybenzyl (Cbz) and the protecting group reagent is benzyl chloroformate or is N-(benzyloxycarbonyloxy)succinimide.

In another aspect, provided herein is a process for preparing a composition comprising a compound of Formula V:

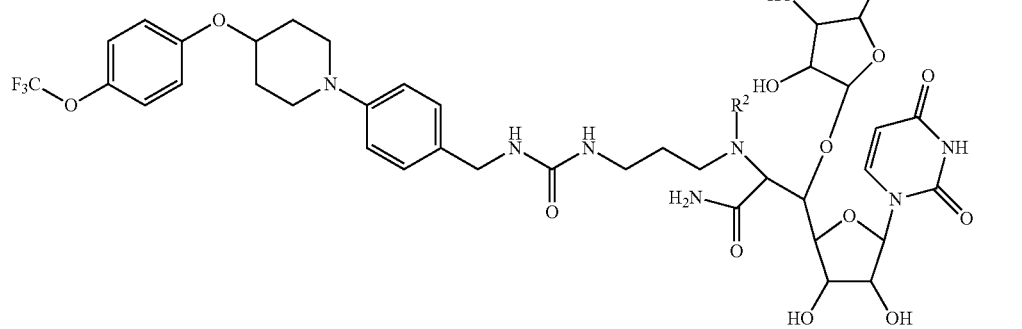

comprising reacting a compound of Formula III:

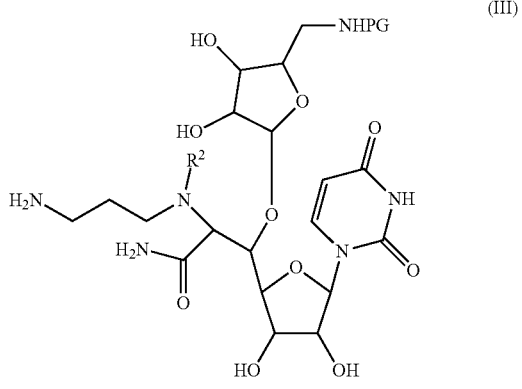

with a compound of Formula IV:

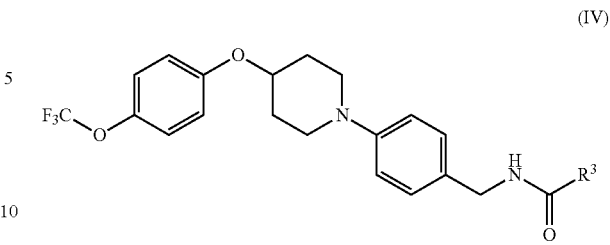

under basic conditions in a solvent wherein

R² is H or C₁-C₆ alkyl;

PG is a protecting group selected from the group consisting of acetyl (Ac), benzyl (Bn), tert-butyloxycarbonyl (Boc), benzoyl (Bz), carboxybenzyl (Cbz), carbamate, 3,4-dimethoxy-benzyl (DMPM), 9-fluorenylmethyloxycarbonyl (Fmoc), p-methoxybenzyl carbonyl (Moz), 4-nitrobenzylsulfonyl (Nos), p-methoxybenzyl (PMB), p-methoxyphenyl (PMP), 4-toluenesulfonyl (Tos), and trichloroethyl chloroformate (Troc); and R³ is selected from the group consisting of OC₁-C₄ alkyl, tosylate, mesylate, iodide, bromide, chloride, imidazole, and triflate.

In an embodiment, R³ is imidazole. In another embodiment, the base is triethylamine. In yet another embodiment, the solvent is a mixture of dimethylformamide and dichloromethane. In still another embodiment, R³ is imidazole, the base is triethylamine, and the solvent is a mixture of dimethylformamide and dichloromethane.

In yet another aspect, provided herein is a process for preparing a composition comprising a compound of Formula I:

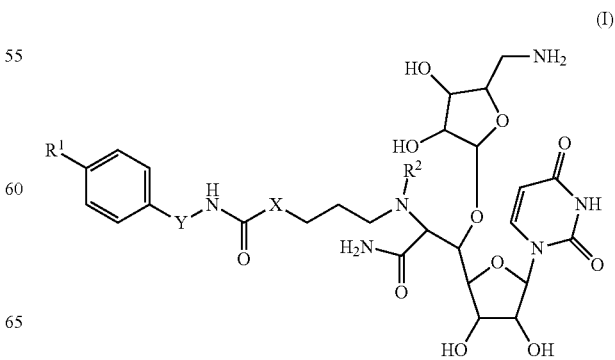

comprising treating a compound of Formula V:

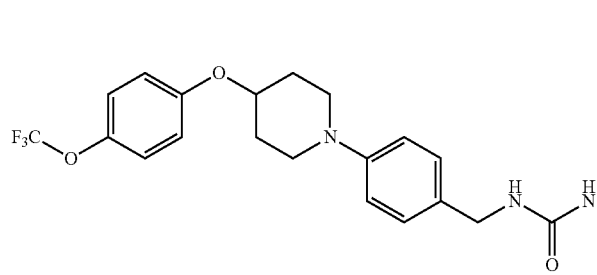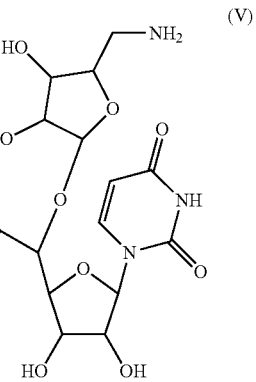

with an acid in a solvent
wherein:
R[1] is piperazine-O-Ph, wherein Ph is optionally substituted with $C_1$-$C_4$ alkyl or $OC_1$-$C_4$ alkyl, wherein $OC_1$-$C_4$ alkyl is optionally further substituted with 1, 2, or 3 halo;
R[2] is H or $C_1$-$C_6$ alkyl;
X is —NH—;
Y is —$(CH_2)_n$—;
PG is a protecting group selected from the group consisting of acetyl (Ac), benzyl (Bn), tert-butyloxycarbonyl (Boc), benzoyl (Bz), carboxybenzyl (Cbz), carbamate, 3,4-dimethoxy-benzyl (DMPM), 9-fluorenylmethyloxycarbonyl (Fmoc), p-methoxybenzyl carbonyl (Moz), 4-nitrobenzylsulfonyl (Nos), p-methoxybenzyl (PMB), p-methoxyphenyl (PMP), 4-toluenesulfonyl (Tos), and trichloroethyl chloroformate (Troc); and
n is 1.

In an embodiment, the acid is trifluoroacetic acid. In another embodiment, the solvent is dichloromethane. In yet another embodiment, PG is tert-butyloxycarbonyl (Boc). In still another embodiment, PG is carboxybenzyl (Cbz). In an embodiment, the acid is trifluoroacetic acid, the solvent is dichloromethane, and PG is tert-butyloxycarbonyl (Boc).

In an aspect, provided herein are compounds prepared by the processes described supra.

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth.

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

ABBREVIATIONS

Å Angstrom
aq. aqueous
Boc tert-butyloxycarbonyl
$Boc_2O$ di-tert-butyl dicarbonate
$CDCl_3$ deuterated chloroform
$CH_3CN$ acetonitrile (MeCN)
$D_2O$ deuterium oxide
DCC N, N'-dicyclohexylcarbodiimide
DCM dichloromethane
DMSO dimethyl sulfoxide
ESI electrospray ionization
$Et_3N$ triethylamine
EtOAc ethyl acetate
EtOH ethanol
Lindlar's cat. 5% Pd—$CaCO_3$, $Pb(OCOCH_3)_2$, and quinoline
MeOD deuterated methanol
MS molecular sieves
MTPM monomethoxytetrachlorodiphenylmethoxymethyl
$Na_2SO_4$ sodium sulfate
$NaB(CN)H_3$ sodium cyanoborohydride
$NaHCO_3$ sodium bicarbonate
NIS N-iodosuccinimide
NMO N-methylmorpholine N-oxide
OAc acetate
OTf triflate, trifluoromethanesulfonate
tBuOH tert-butanol
TFA trifluoroacetic acid
THF tetrahydrofuran
TIPS triisopropylsilane
TMS trimethylsilane
TMSCN trimethylsilyl cyanide
Tol toluene Example 1: Synthesis of Compound 9

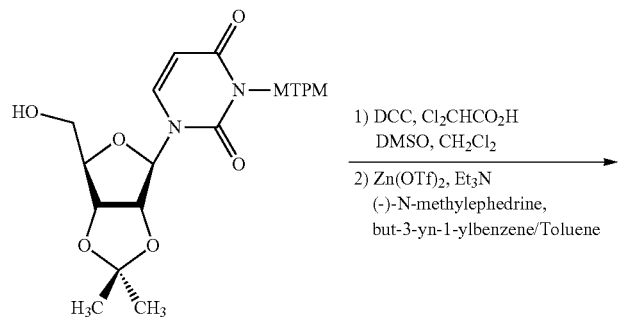

13

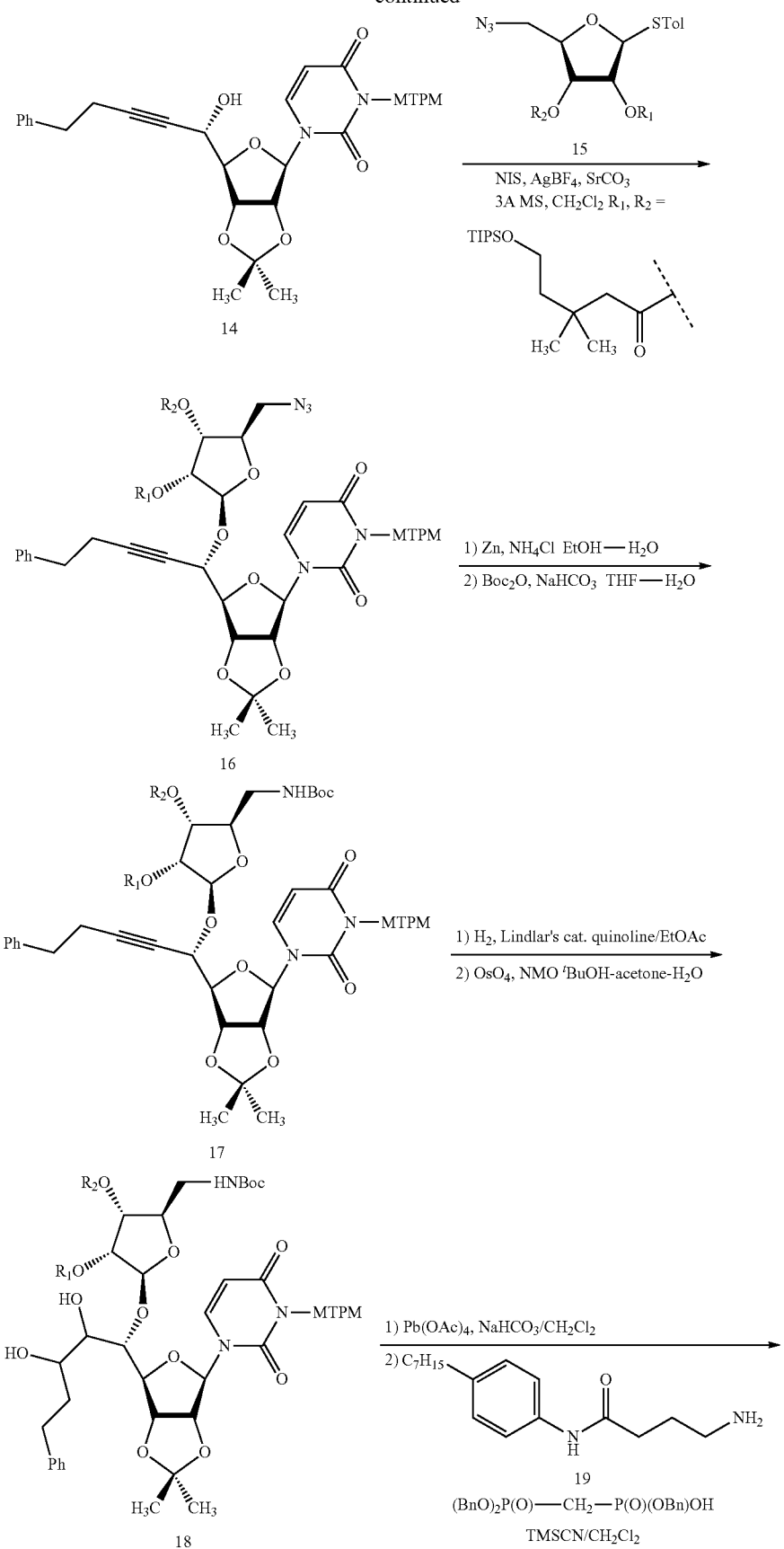

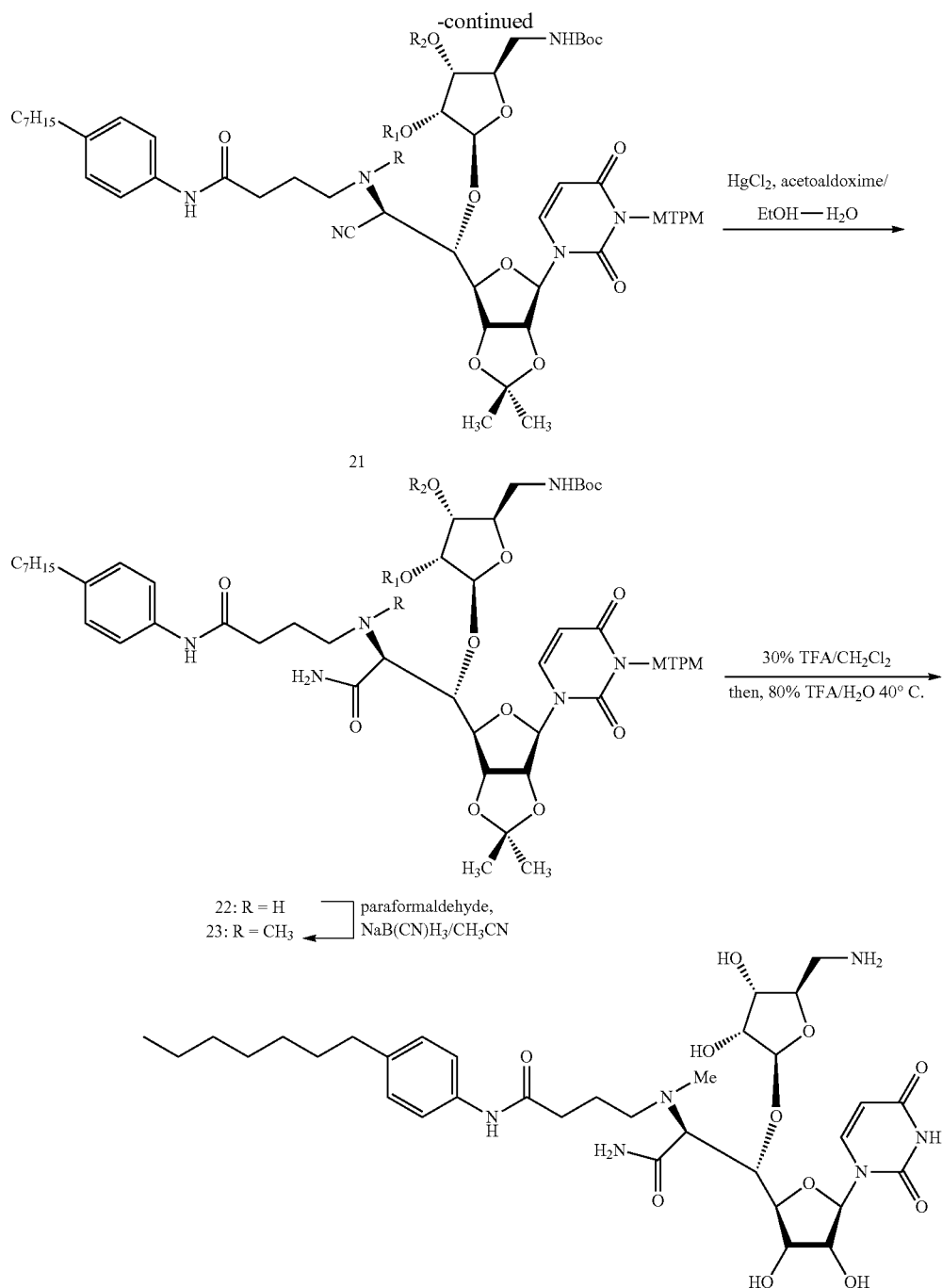

Step 1

To a stirred solution of 13 (0.65 g, 1.0 mmol) and dichloroacetic acid (0.12 mL, 1.5 mmol) in $CH_2Cl_2$ (5.0 mL) and DMSO (1.0 mL) was added DCC (0.23 mL, 1.5 mmol) at 0° C., and the reaction mixture was warmed to rt. After 8 h, the reaction was quenched with aq. saturated $NaHCO_3$ and extracted with EtOAc. The combined organic extracts were dried over $Na_2SO_4$ and concentrated in vacuo. The precipitates were filtered, and the crude aldehyde was used for next reaction without purification. To a suspension of $Zn(OTf)_2$ (1.45 g, 4.0 mmol) and (+)-N-methylephedrine (0.79 g, 4.8 mmol) in toluene (6 mL) was added $Et_3N$ (0.61 mL, 4.8 mmol) at rt. After 2 h, 4-phenyl-1-butyne (0.62 mL, 4.8 mmol) was added. After 4 h, a solution of crude aldehyde in toluene (5 mL) was added. The reaction mixture was stirred for 16 h and quenched with aq. saturated $NaHCO_3$, extracted with EtOAc. The combined organic extracts were dried over $Na_2SO_4$ and concentrated in vacuo. The crude mixture was purified by silica gel column chromatography (hexanes/EtOAc 60:40) to afford 14 (0.62 g, 0.80 mmol, 80% for 2 steps): TLC (hexanes/EtOAc 50:50) $R_f$=0.30; $[\alpha]^{22}_D$ –0.116 (c=2.17, $CHCl_3$); IR (thin film) $v_{max}$=3387 (br), 3087, 2981, 2937, 1716, 1664, 1597, 1556, 1454, 1374, 1276, 1211, 1156, 1065, 1039, 916, 856, 807, 786, 733, 698 cm$^{-1}$; $^1$H NMR (400 MHz, CDCl$_3$) δ 7.53 (ddd, J=20.4, 8.5, 0.7 Hz, 1H), 7.35-7.27 (m, 4H), 7.24-7.15 (m, 4H), 6.85 (d, J=5.1 Hz, 2H), 6.51 (d, J=5.4 Hz, 1H), 5.68 (dd, J=8.1, 4.1 Hz, 1H), 5.60-5.50 (m, 3H), 4.89-4.78 (m, 2H), 4.57 (dd, J=12.0, 4.3, 2.0 Hz, 1H), 4.24 (dd, J=4.4, 3.1 Hz, 1H), 3.78 (d, J=3.3 Hz, 3H), 2.83 (t, J=7.5 Hz, 2H), 2.53 (td, J=7.4, 2.0 Hz, 2H), 1.57 (s, 3H), 1.36 (s, 3H); $^{13}$C NMR (101 MHz, CDCl$_3$) δ 162.11, 162.08, 159.50, 150.87, 150.85, 141.07, 140.84, 140.30, 140.27, 136.90, 135.36, 135.29, 133.99, 133.95, 133.79, 133.64, 131.21, 129.37, 129.34, 128.41, 128.39, 126.40, 126.21, 126.18, 125.49, 125.44, 115.34, 115.32, 114.28, 114.24, 101.79, 101.74, 96.69, 96.37, 89.23, 89.19, 86.83, 86.73, 84.09, 83.93, 80.91, 69.46, 63.02, 62.99, 55.68, 34.72, 34.70, 27.16, 25.29, 20.87, 20.85; HRMS (ESI$_+$) m/z calcd for C$_{37}$H$_{34}$N$_2$O$_8$NaCl$_4$ [M+Na] 797.0967, found: 797.0994.

Step 2

To a stirred suspension of 14 (227 mg, 0.292 mmol), 15 (497 mg, 0.584 mmol), 3 Å molecular sieves (900 mg) and SrCO$_3$ (431 mg, 2.920 mmol) in CH$_2$Cl$_2$ (12.0 mL) were added AgBF$_4$ (28.5 mg, 0.146 mmol) and NIS (131 mg, 0.584 mmol) at 0° C. After 24 h, Et$_3$N (2 mL) was added to the reaction mixture, and the mixture was passed through a silica gel pad (hexanes/EtOAc 1:1). The combined organic phase was concentrated in vacuo. The crude mixture was purified by silica gel column chromatography (hexanes/EtOAc 90:10 to 80:20 to 70:30) to afford 16 (416 mg, 0.277 mmol, 95%): TLC (hexanes/EtOAc 67:33) R$_f$=0.70; [α]$^{21}_D$+ 0.100 (c=2.09, CHCl$_3$); IR (thin film) ν$_{max}$=2942, 2866, 2102, 1743, 1724, 1675, 1456, 1278, 1218, 1099, 1070, 882, 772 cm$^{-1}$; $^1$H NMR (400 MHz, CDCl$_3$) δ 7.54 (dd, J=23.1, 8.5 Hz, 1H), 7.32-7.27 (m, 4H), 7.24-7.16 (m, 4H), 6.84 (d, J=7.3 Hz, 2H), 6.51 (d, J=3.7 Hz, 1H), 5.71-5.64 (m, 2H), 5.60-5.49 (m, 2H), 5.20-5.16 (m, 3H), 4.79 (ddd, J=7.5, 6.5, 3.1 Hz, 1H), 4.64 (td, J=5.9, 2.6 Hz, 1H), 4.57 (ddt, J=11.4, 6.3, 1.9 Hz, 1H), 4.28 (dt, J=6.2, 2.8 Hz, 1H), 4.19 (tt, J=6.1, 3.0 Hz, 1H), 3.79-3.72 (m, 7H), 3.50 (ddd, J=13.0, 7.6, 3.3 Hz, 1H), 3.35 (dd, J=13.0, 3.4 Hz, 1H), 2.83 (t, J=7.4 Hz, 2H), 2.55 (td, J=7.4, 1.8 Hz, 2H), 2.29 (t, J=1.6 Hz, 2H), 2.24 (dd, J=5.1, 2.1 Hz, 2H), 1.62-1.55 (m, 7H), 1.36 (d, J=2.0 Hz, 3H), 1.08-1.00 (m, 54H); $^{13}$C NMR (101 MHz, CDCl3) δ 175.6, 171.0, 170.9, 170.71, 170.70, 170.6, 162.2, 162.1, 159.5, 150.8, 150.7, 140.4, 140.19, 140.15, 140.13, 136.92, 136.91, 135.4, 135.3, 133.9, 133.8, 133.7, 131.2, 129.4, 129.3, 128.5 (2C), 128.4 (2C), 126.5, 126.4, 126.2, 126.1, 125.6, 125.5, 115.29, 115.25, 114.23, 114.22, 104.61, 104.55, 101.83, 101.82, 88.8, 88.2, 84.44, 84.35, 83.9, 81.4, 81.3, 80.6, 79.9, 76.5, 75.9, 75.8, 74.1, 71.8, 71.7, 71.4, 70.7, 69.6, 69.5, 68.9, 68.8, 59.97, 59.96, 55.7, 46.2, 46.0, 44.7, 44.6, 34.7, 34.51, 34.49, 32.7, 32.61, 32.57, 28.0, 27.38, 27.35, 27.3, 27.1, 25.34, 25.27, 20.9, 18.1 (12C), 11.9 (6C); HRMS (ESI$_+$) m/z calcd for C$_{74}$H$_{106}$Cl$_4$N$_5$O$_{15}$Si$_2$ [M+H] 1500.5978, found: 1500.5992.

Step 3

A suspended solution of 16 (286 mg, 0.19 mmol), NH$_4$Cl (305 mg, 5.70 mmol) and Zn (373 mg, 5.70 mmol) in EtOH/H$_2$O (9:1, 9.5 mL) was stirred at 80° C. for 12 h and cooled to rt. The precipitates were filtered and the combined organic solution was concentrated in vacuo. The crude mixture was used for the next reaction without purification. To a stirred solution of crude mixture in THF (9.5 mL) were added saturated NaHCO$_3$ (aq., 9.5 mL) and Boc$_2$O (124 mg, 0.57 mmol). The reaction mixture was stirred for 6 h at rt, and the aqueous layer was extracted with EtOAc. The combined organic extracts were dried over Na$_2$SO$_4$ and concentrated in vacuo. The crude mixture was purified by silica gel column chromatography (hexanes/EtOAc 85:15 to 80:20 to 67:33) to afford 17 (258 mg, 0.16 mmol, 86% for 2 steps): TLC (hexanes/EtOAc 70:30) R$_f$=0.30; [α]$^{21}_D$+ 0.012 (c=0.90, CHCl$_3$); IR (thin film) ν$_{max}$=2941, 2866, 1720, 1676, 1456, 1366, 1278, 1219, 1100, 1070, 882, 772 cm$^{-1}$; $^1$H NMR (400 MHz, CDCl$_3$) δ 7.54 (dd, J=19.9, 8.5 Hz, 1H), 7.33-7.27 (m, 4H), 7.24-7.16 (m, 4H), 6.85 (d, J=7.3 Hz, 2H), 6.51 (d, J=4.8 Hz, 1H), 5.72-5.64 (m, 2H), 5.60-5.48 (m, 2H), 5.26 (d, J=6.0 Hz, 1H), 5.17 (d, J=8.6 Hz, 2H), 5.13-5.08 (m, 1H), 4.82-4.76 (m, 1H), 4.65 (t, J=7.0 Hz, 1H), 4.51 (dd, J=13.8, 6.0 Hz, 1H), 4.31-4.26 (m, 1H), 4.23-4.17 (m, 1H), 3.78 (d, J=2.7 Hz, 3H), 3.74 (d, J=6.9 Hz, 4H), 3.48-3.40 (m, 1H), 3.36-3.26 (m, 1H), 2.83 (t, J=7.4 Hz, 2H), 2.56 (t, J=7.5 Hz, 2H), 2.27 (t, J=2.6 Hz, 2H), 2.23 (t, J=3.0 Hz, 2H), 1.62-1.55 (m, 7H), 1.42 (s, 9H), 1.37 (d, J=2.6 Hz, 3H), 1.11-0.99 (m, 54H); $^{13}$C NMR (101 MHz, CDCl$_3$) δ 159.5, 150.8, 136.9, 131.3, 129.3, 128.5 (2C), 128.4 (2C), 126.5, 126.1, 125.4, 115.30, 115.26, 80.0, 60.0, 55.7, 46.4, 46.2, 46.0, 44.83, 44.78, 42.5, 34.51, 34.49, 32.60, 32.55, 31.9, 29.7, 28.7, 28.4, 28.3, 27.4, 27.33, 27.29, 27.26, 27.09, 27.05, 25.4, 22.7, 22.6, 20.9, 18.1 (6C), 17.9 (6C), 14.1, 11.9 (3C), 11.8 (3C); HRMS (ESI$_+$) m/z calcd for C$_{79}$H$_{116}$Cl$_4$N$_3$O$_{17}$Si$_2$ [M+H] 1574.6597, found: 1574.6609.

Step 4

To a stirred solution of 17 (258 mg, 0.16 mmol) and quinoline (38.7 μL, 0.33 mmol) in EtOAc (50 mL) and MeOH (50 mL) was added Lindlar catalyst (300 mg). H$_2$ gas was introduced and the reaction mixture was stirred under H$_2$ atmosphere (600 psi) at rt. After being stirred for 7 h, Lindlar catalyst (150 mg) was added to the reaction mixture. The reaction mixture was stirred for 11 h under H$_2$ atmosphere (600 psi) at rt. The solution was filtered through Celite and washed with 1N HCl (aq.). The combined organic solution was dried over Na$_2$SO$_4$, concentrated in vacuo. The crude mixture was used for the next reaction without purification. To a stirred solution of the crude mixture and NMO (192 mg, 1.64 mmol) in t-BuOH/acetone (1:1, 2.1 mL) was added OsO$_4$ (4% in water, 1.04 mL, 0.16 mmol) at rt. After the reaction was stirred for 2 h at 40° C., NMO (192 mg, 1.64 mmol) and OsO$_4$ (4% in water, 1.04 mL, 0.16 mmol) were added. After being stirred for 2 h at 40° C., the reaction solution was diluted with EtOAc and quenched with saturated NaHCO$_3$ aq./saturated Na$_2$SO$_3$ aq. (2:1). The heterogeneous mixture was stirred for 30 min then extracted with EtOAc. The combined organic extracts were dried over Na$_2$SO$_4$ and concentrated in vacuo. The crude mixture was passed through a silica gel pad (hexanes/EtOAc 33:67) to afford 18 as diastereomeric mixture. This mixture was used for next reaction without further purification.

Step 5

To a stirred solution of 18 (22.1 mg, 0.014 mmol) and NaHCO$_3$ (11.5 mg, 0.14 mmol) in CH$_2$Cl$_2$ (0.7 mL) was added Pb(OAc)$_4$ (12.1 mg, 0.027 mmfol) at 0° C. The reaction mixture was stirred for 2 h at 0° C. and quenched with saturated NaHCO$_{3(aq)}$, extracted with EtOAc. The combined organic extracts were dried over Na$_2$SO$_4$ and concentrated in vacuo. The crude mixture of aldehyde 18 was used for the next reaction without purification. To a stirred solution of (BnO)$_2$P(O)—CH$_2$—P(O)(OBn)OH (30.6 mg, 0.069 mmol) in CH$_2$Cl$_2$ (0.4 mL) was added a CH$_2$Cl$_2$ (0.3 mL) solution of the mixture of 18, 19 was added to the solution. After 9 h, the reaction was added TMSCN (17.1 μL, 0.14 mmol) and stirred for 9 h at rt. After completion, the reaction was quenched with saturated NaHCO$_3$ aq., extracted with EtOAc. The combined organic extracts were dried over Na$_2$SO$_4$ and concentrated in vacuo. The crude product was purified by silica gel column chromatography (hexanes/EtOAc 80:20 to 60:40) to afford 21 (16.7 mg, 9.49 μmol, 69% for 2 steps): TLC (hexanes/EtOAc 60:40) $R_f$=0.40; $[\alpha]^{21}_D$+0.075 (c=0.73, CHCl$_3$); IR (thin film) $v_{max}$=3317 (br), 2930, 2865, 1719, 1675, 1600, 1462, 1102, 1071, 882, 772, 683 cm$^{-1}$; $^1$H NMR (400 MHz, CDCl$_3$) δ 7.68 (s, 1H), 7.49 (dd, J=11.4, 8.8 Hz, 1H), 7.39 (d, J=7.9 Hz, 2H), 7.32 (s, 1H), 7.19 (d, J=8.5 Hz, 2H), 7.11 (d, J=8.0 Hz, 2H), 6.86 (d, J=9.3 Hz, 2H), 6.50 (d, J=15.4 Hz, 1H), 5.73 (dd, J=23.0, 8.0 Hz, 1H), 5.59 (d, J=5.9 Hz, 1H), 5.54 (d, J=9.4 Hz, 2H), 5.42 (t, J=10.1 Hz, 1H), 5.25 (s, 1H), 5.08-5.00 (m, 2H), 4.96-4.82 (m, 2H), 4.50-4.45 (m, 1H), 4.25-4.19 (m, 1H), 4.15-4.06 (m, 1H), 3.94-3.83 (m, 1H), 3.80-3.63 (m, 10H), 3.49-3.41 (m, 1H), 3.39-3.31 (m, 1H), 3.03 (dt, J=12.0, 6.1 Hz, 1H), 2.71-2.61 (m, 1H), 2.54 (t, J=7.3 Hz, 2H), 2.51-2.45 (m, 1H), 2.29-2.17 (m, 4H), 1.67-1.51 (m, 10H), 1.41 (s, 9H), 1.28 (dd, J=15.7, 8.1 Hz, 10H), 1.05 (s, 42H), 1.01 (s, 6H), 0.95 (s, 6H), 0.87 (t, J=6.4 Hz, 3H); $^{13}$C NMR (101 MHz, CDCl$_3$) δ 170.9, 159.5, 136.9, 136.8, 131.3, 131.2, 129.42, 129.36, 128.84 (2C), 128.82 (2C), 128.80 (2C), 126.4, 126.2, 125.1, 120.09, 120.05, 115.4, 115.31, 115.30, 114.84, 114.81, 84.90, 84.87, 80.84, 80.78, 80.2, 79.8, 79.4, 78.2, 76.1, 74.3, 60.0, 59.9, 55.8, 55.7, 52.0, 46.2, 46.0, 44.83, 44.77, 35.4, 32.56, 32.55, 31.8, 31.5, 29.7, 29.19, 29.16, 28.4, 28.3, 27.3, 27.2, 22.7, 18.1 (12C), 14.1, 11.9 (6C); HRMS (ESI$_+$) m/z calcd for C$_{88}$H$_{135}$Cl$_4$N$_6$O$_{18}$Si$_2$ [M+H] 1759.8126, found: 1759.8135.

Step 6

To a stirred solution of 21 (8.8 mg, 5.0 umol) in EtOH/H$_2$O (9:1, 0.5 mL) were added HgCl$_2$ (2.7 mg, 0.010 mmol) and acetaldoxime (3.0 μL, 0.050 mmol) at rt. After being stirred for 6 h at rt, the reaction mixture was concentrated under reduced pressure. The residue was quenched with saturated NaHCO$_3$ aq. and extracted with CHCl$_3$. The combined organic extracts were dried over Na$_2$SO$_4$ and concentrated in vacuo. The crude product was purified by silica gel column chromatography (CHCl$_3$/MeOH 99.5:0.5 to 99.2:0.8 to 98.8:1.2) to afford 22 (7.9 mg, 4.5 μmol, 89%): TLC (CHCl$_3$/MeOH 95:5) $R_f$=0.40; IR (thin film) $v_{max}$=3335 (br), 2927, 2865, 1668, 1601, 1460, 1099, 1071, 882, 681 cm$^{-1}$; $^1$H NMR (400 MHz, CDCl$_3$) δ 7.59 (dd, J=19.5, 8.5 Hz, 1H), 7.40 (d, J=8.0 Hz, 2H), 7.30 (t, J=2.6 Hz, 1H), 7.24-7.18 (m, 1H), 7.11 (d, J=8.0 Hz, 2H), 6.84 (d, J=7.2 Hz, 2H), 6.50 (s, 1H), 5.84 (brs, 1H), 5.59-5.47 (m, 3H), 5.26-5.14 (m, 2H), 5.06-4.97 (m, 1H), 4.96-4.87 (m, 1H), 4.84-4.73 (m, 1H), 4.55 (t, J=5.0 Hz, 1H), 4.28-4.14 (m, 2H), 3.80-3.70 (m, 7H), 3.59-3.46 (m, 1H), 3.41 (brs, 2H), 2.83 (brs, 2H), 2.54 (t, J=7.7 Hz, 3H), 2.50-2.43 (m, 1H), 2.29-2.21 (m, 4H), 1.99 (brs, 2H), 1.65-1.53 (m, 10H), 1.43 (s, 9H), 1.35 (d, J=5.2 Hz, 3H), 1.32-1.24 (m, 10H), 1.05 (d, J=3.2 Hz, 48H), 1.00-0.97 (m, 6H), 0.87 (t, J=6.8 Hz, 3H); $^{13}$C NMR (101 MHz, CDCl$_3$) δ 159.6, 159.5, 136.87, 136.85, 136.4, 135.2, 134.0, 133.64, 133.59, 131.3, 129.42, 129.40, 128.9 (2C), 126.2, 125.3, 120.2, 120.1, 115.4 (2C), 74.5, 60.0, 59.9, 55.73, 55.72, 46.2, 46.1, 46.0, 44.8, 35.4, 32.7, 32.6, 31.8, 31.5, 29.69, 29.67, 29.6, 29.5, 29.4, 29.3, 29.24, 29.16, 29.09, 28.51, 28.49, 28.48, 28.45, 28.43, 28.42, 28.36, 28.33, 28.31, 28.28, 27.33, 27.30, 27.25, 27.2, 25.3, 22.7, 18.1 (12C), 14.1, 11.9 (6C); HRMS (ESI$_+$) m/z calcd for C$_{88}$H$_{137}$C$_4$N$_6$O$_{19}$Si$_2$ [M+H] 1777.8231, found: 1777.8219.

Step 7

To a stirred solution of 22 (5.8 mg, 3.3 μmol) and paraformaldehyde (2.9 mg, 0.098 mmol) in CH$_3$CN (0.5 mL) were added NaB(CN)H$_3$ (6.2 mg, 0.098 mmol). After being stirred for 4 h at rt, the reaction mixture was quenched with saturated NaHCO$_3$ aq. and extracted with CHCl$_3$. The combined organic extracts were dried over Na$_2$SO$_4$ and concentrated in vacuo. The crude product was purified by silica gel column chromatography (hexanes/EtOAc 40:60) to afford 23 (5.5 mg, 3.1 μmol, 95%): TLC (hexanes/EtOAc 33:67) $R_f$=0.60; $[\alpha]^{21}_D$+0.022 (c=0.28, CHCl$_3$); IR (thin film) $v_{max}$=2932, 2866, 1718, 1672, 1601, 1463, 1101, 1071, 884 cm$^{-1}$; $^1$H NMR (400 MHz, CDCl$_3$) δ 7.75 (d, J=17.0 Hz, 1H), 7.56 (d, J=8.6 Hz, 1H), 7.43 (d, J=8.1 Hz, 2H), 7.34 (d, J=8.1 Hz, 1H), 7.30 (s, 2H), 7.20 (dt, J=8.5, 2.0 Hz, 1H), 7.10 (d, J=8.1 Hz, 2H), 6.85 (s, 2H), 6.51 (d, J=7.9 Hz, 1H), 6.28 (brs, 1H), 5.95 (d, J=21.6 Hz, 1H), 5.84-5.78 (m, 1H), 5.74 (d, J=23.3 Hz, 1H), 5.54 (s, 2H), 5.49 (d, J=9.6 Hz, 1H), 5.18 (brs, 1H), 5.11 (s, 2H), 5.02 (brs, 1H), 4.88-4.83 (m, 1H), 4.80-4.74 (m, 1H), 4.39-4.31 (m, 2H), 4.24-4.18 (m, 1H), 3.92 (t, J=5.8 Hz, 1H), 3.78 (s, 3H), 3.74 (q, J=6.6 Hz, 4H), 3.68-3.63 (m, 1H), 3.50-3.40 (m, 2H), 3.37-3.30 (m, 1H), 2.83-2.74 (m, 1H), 2.68-2.59 (m, 1H), 2.54 (t, J=7.8 Hz, 2H), 2.49 (s, 3H), 2.37 (q, J=8.0, 7.6 Hz, 2H), 2.29-2.20 (m, 4H), 1.98-1.88 (m, 2H), 1.62-1.52 (m, 6H), 1.40 (s, 9H), 1.36 (brs, 3H), 1.33-1.23 (m, 6H), 1.09-1.01 (m, 48H), 0.98 (s, 6H), 0.87 (t, J=6.4 Hz, 3H); $^{13}$C NMR (101 MHz, CDCl$_3$) δ 171.0, 162.0, 159.5, 157.1, 136.9, 131.3, 129.4, 128.7 (2C), 119.9 (2C), 115.3, 115.1, 114.2, 70.6, 70.1, 69.9, 67.1, 60.4, 60.1, 59.96, 59.95, 58.9, 55.8, 55.7, 54.4, 54.1, 46.22, 46.16, 46.1, 45.3, 44.9, 44.8, 44.7, 42.3, 41.2, 39.93, 39.86, 39.6, 39.04, 38.97, 35.4, 32.7, 32.64, 32.63, 32.62, 32.58, 31.9, 31.8, 31.7, 31.6, 31.53, 31.48, 29.69, 29.67, 29.6, 29.4, 29.22, 29.17, 28.50, 28.49, 28.4, 27.29, 27.28, 27.21, 27.17, 25.23, 25.20, 22.68, 22.66, 18.1 (12C), 14.1, 11.9 (6C); HRMS (ESI$_+$) m/z calcd for C$_{89}$H$_{139}$C$_{14}$N$_6$O$_{19}$Si$_2$ [M+H] 1791.8388, found: 1791.8404.

Step 8

To a stirred solution of 23 (2.9 mg, 1.6 μmol) in CH$_2$Cl$_2$ (0.70 mL) was added TFA (0.30 mL). The reaction mixture was stirred for 2 h at rt, and all volatile solvents were evaporated in vacuo. To a stirred solution of the crude mixture in H$_2$O (0.2 mL) was added TFA (0.8 mL). The reaction mixture was stirred for 4 h at 40° C., and all volatile solvents were evaporated in vacuo. The crude mixture was purified by silica gel column chromatography (CHCl$_3$/MeOH 80:20 to CHCl$_3$/MeOH/H$_2$O/50% aqueous ammonia 56:42:7:3) to afford 9 (1.2 mg, 1.6 μmol, 100%): TLC (n-butanol/ethanol/CHCl$_3$/28% aqueous ammonia 4:7:2:7) $R_f$=0.55; $[\alpha]^{20}_D$+0.038 (c=0.12, methanol); IR (thin film) $v_{max}$=3333 (br), 2926, 2855, 1676, 1204, 1135, 840, 801, 722 cm$^{-1}$; $^1$H NMR (400 MHz, CD$_3$OD) δ 7.82 (d, J=8.1 Hz, 1H), 7.44 (d, J=8.0 Hz, 2H), 7.12 (d, J=8.1 Hz, 2H), 5.76 (d, J=8.0 Hz, 1H), 5.70 (s, 1H), 5.18 (s, 1H), 4.58 (s, 1H), 4.28 (d, J=9.3 Hz, 1H), 4.21-4.16 (m, 3H), 4.14-4.07 (m, 3H), 3.61 (d, J=9.4 Hz, 1H), 3.21 (dd, J=13.6, 3.4 Hz, 1H), 2.83 (td, J=12.1, 11.7, 5.0 Hz, 1H), 2.57 (t, J=7.6 Hz, 2H), 2.46 (s, 3H), 2.46-2.40 (m, 2H), 2.00-1.89 (m, 1H), 1.79 (d, J=12.4 Hz, 1H), 1.63-1.55 (m, 2H), 1.37-1.23 (m, 10H), 0.91-0.87 (m, 3H); $^{13}$C NMR (101 MHz, CD$_3$OD) δ 173.9, 172.3, 142.4, 140.2, 137.3, 129.7 (2C), 121.5 (2C), 112.1, 102.4, 92.5, 84.2, 80.5, 78.4, 76.4, 75.4, 72.0, 70.8, 68.5, 54.5, 39.5, 36.3, 35.0, 33.0, 32.8, 30.29, 30.26, 24.3, 23.7, 14.4; HRMS (ESI$_+$) m/z calcd for C$_{34}$H$_{53}$N$_6$O$_{11}$ [M+H] 721.3772, found: 721.3761.

Example 2: Synthesis of Compound 10

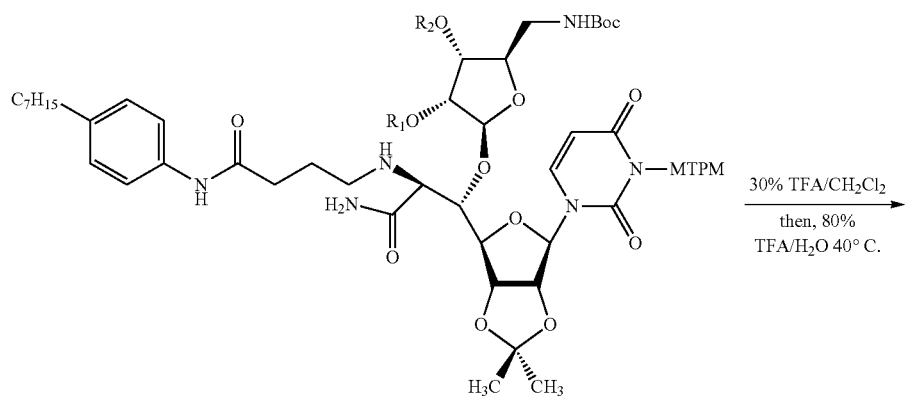

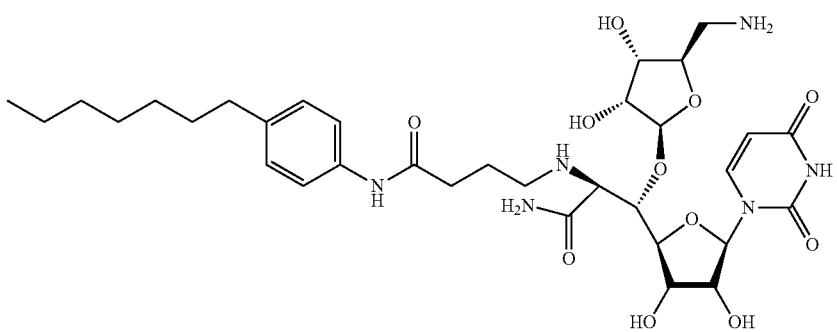

To a stirred solution of 22 (7.9 mg, 4.5 μmol) in CH$_2$Cl$_2$ (0.70 mL) was added TFA (0.30 mL). The reaction mixture was stirred for 1 h at rt, and all volatile solvents were evaporated in vacuo. To a stirred solution of the crude mixture in H$_2$O (0.2 mL) was added TFA (0.8 mL). The reaction mixture was stirred for 2 h at 40° C., and all volatile solvents were evaporated in vacuo. The crude mixture was purified by silica gel column chromatography (CHCl$_3$/MeOH 80:20 to CHCl$_3$/MeOH/H$_2$O/50% aqueous ammonia 56:42:7:3) to afford 10 (2.4 mg, 3.4 μmol, 76%, 95.8% purity): TLC (n-butanol/ethanol/CHCl$_3$/28% aqueous ammonia 4:7:2:7) $R_f$=0.50; $[\alpha]^{21}_D$+0.538 (c=0.24, methanol); IR (thin film) $v_{max}$=3302 (br), 2926, 1672, 1542, 1412, 1271, 1131, 1111, 1062, 819, 721 cm$^{-1}$; $^1$H NMR (400 MHz, CD$_3$OD) δ 7.77 (d, J=8.1 Hz, 1H), 7.43 (d, J=8.1 Hz, 2H), 7.12 (d, J=8.0 Hz, 2H), 5.74 (s, 1H), 5.73 (d, J=12.6 Hz, 1H), 5.14 (s, 1H), 4.21 (dd, J=4.7, 4.2 Hz, 1H), 4.19-4.13 (m, 2H), 4.11 (t, J=4.7 Hz, 1H), 4.08 (s, 2H), 4.02-3.99 (m, 1H), 3.50 (d, J=8.9 Hz, 1H), 3.24 (d, J=13.0 Hz, 1H), 3.16-3.09 (m, 1H), 2.73-2.60 (m, 2H), 2.57 (t, J=7.7 Hz, 2H), 2.43 (dd, J=7.4, 4.0 Hz, 2H), 1.86 (quin, J=7.2 Hz, 2H), 1.59 (quin, J=6.4, 5.7 Hz, 2H), 1.35-1.26 (m, 8H), 0.92-0.87 (m, 3H); $^{13}$C NMR (101 MHz, CD$_3$OD) δ 177.2, 174.2, 166.1, 152.1, 142.6, 140.1, 137.4, 129.7 (2C), 121.5 (2C), 110.6, 102.7, 92.5, 85.2, 80.5, 76.4, 75.0, 73.0, 71.2, 64.3, 43.2, 36.3, 35.5, 33.0, 32.8, 30.3, 26.6, 23.7, 14.4; HRMS (ESI$_+$) m/z calcd for C$_{33}$H$_{51}$N$_6$O$_{11}$ [M+H] 707.3616, found: 707.3624.

Example 3: Synthesis of Compound 11
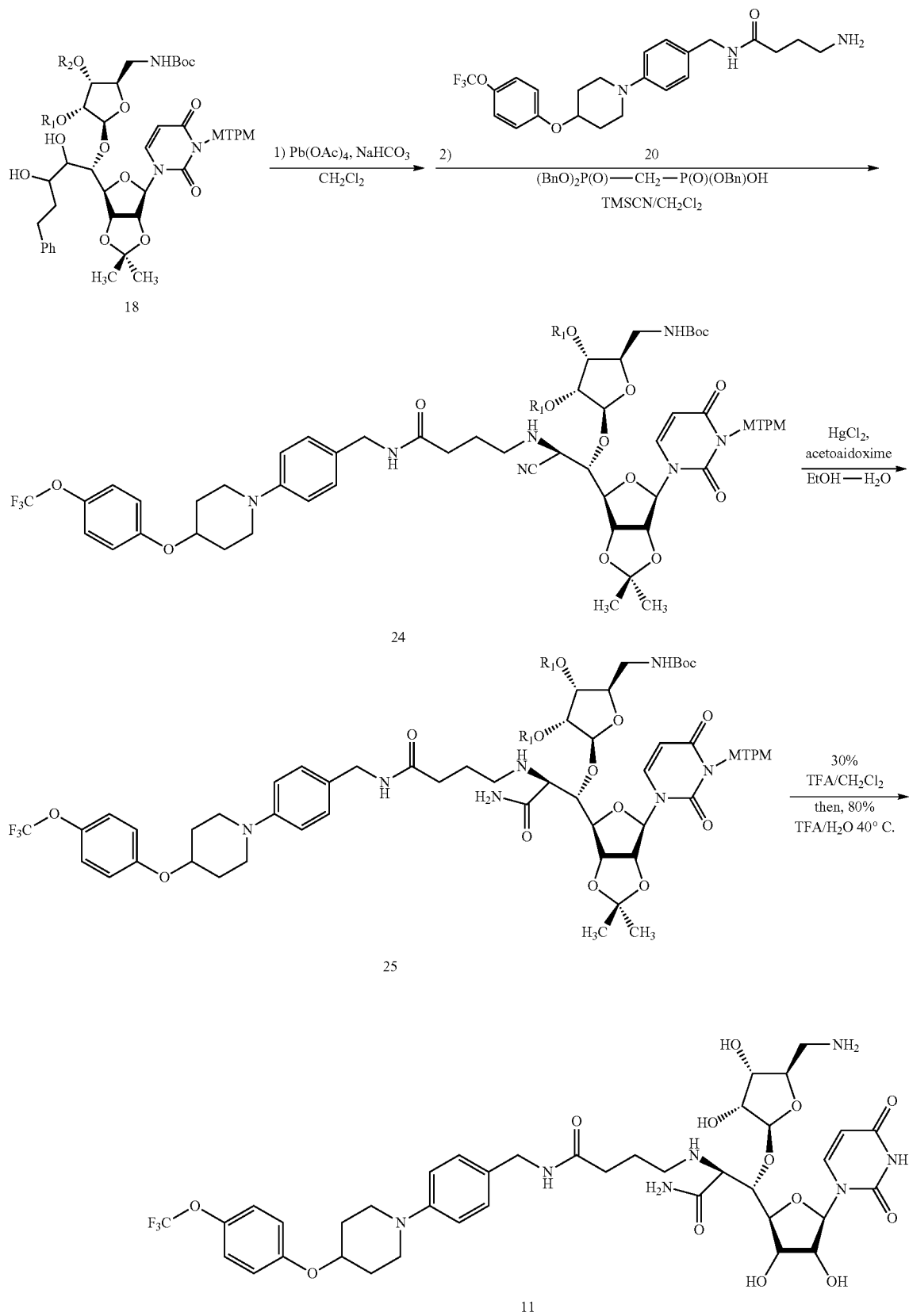

Step 1

To a stirred solution of 18 (32.5 mg, 0.020 mmol) and NaHCO$_3$ (16.9 mg, 0.20 mmol) in CH$_2$Cl$_2$ (1.0 mL) was added Pb(OAc)$_4$ (17.9 mg, 0.040 mmfol) at 0° C. The reaction mixture was stirred for 2 h at 0° C. and quenched with saturated NaHCO$_3$ aq. then extracted with EtOAc. The combined organic extracts were dried over Na$_2$SO$_4$ and concentrated in vacuo. The crude product was dissolved in CH$_2$Cl$_2$ (0.5 mL) and added to a stirred solution of (BnO)$_2$P(O)—CH$_2$—P(O)(OBn)OH (45.0 mg, 0.10 mmol) in CH$_2$Cl$_2$ (0.5 mL). Then 20 was added to the solution. After 6 h, the reaction was added TMSCN (25.2 µL, 0.20 mmol) and stirred for 12 h at rt. After completion, the reaction mixture was quenched with saturated NaHCO$_3$ aq. and extracted with EtOAc. The combined organic extracts were dried over Na$_2$SO$_4$ and concentrated in vacuo. The crude product was purified by silica gel column chromatography (hexanes/EtOAc 80:20 to 60:40) to afford 24 (23.9 mg, 0.012 mmol, 61% for 2 steps): TLC (hexanes/EtOAc 50:50) R$_f$=0.40; [α]$^{21}_D$+0.102 (c=0.75, CHCl$_3$); IR (thin film) v$_{max}$=3342 (br), 2941, 2866, 1718, 1675, 1505, 1464, 1243, 1164, 1101, 1071, 883, 772, 688 cm$^{-1}$; $^1$H NMR (400 MHz, CDCl$_3$) δ 7.49 (dd, J=8.5, 4.3 Hz, 1H), 7.32 (d, J=2.0 Hz, 1H), 7.22-7.11 (m, 7H), 6.94-6.88 (m, 5H), 6.86 (d, J=6.5 Hz, 2H), 6.50 (d, J=8.6 Hz, 1H), 6.25-6.16 (m, 1H), 5.73 (dd, J=22.2, 8.0 Hz, 1H), 5.60 (t, J=8.8 Hz, 1H), 5.56-5.41 (m, 3H), 5.21 (d, J=4.4 Hz, 1H), 5.05-4.98 (m, 2H), 4.94-4.77 (m, 2H), 4.53-4.37 (m, 3H), 4.25-4.16 (m, 2H), 4.05-3.98 (m, 1H), 3.80-3.69 (m, 6H), 3.68-3.63 (m, 1H), 3.56 (dd, J=17.3, 3.4 Hz, 1H), 3.48 (ddt, J=11.6, 7.2, 4.0 Hz, 2H), 3.44-3.29 (m, 1H), 3.08 (dq, J=9.5, 5.3, 4.8 Hz, 2H), 2.95 (dt, J=11.4, 5.5 Hz, 1H), 2.47 (td, J=12.0, 11.4, 5.7 Hz, 1H), 2.36-2.14 (m, 5H), 2.13-2.05 (m, 2H), 1.97-1.85 (m, 3H), 1.84-1.75 (m, 1H), 1.58 (t, J=6.9 Hz, 2H), 1.55-1.50 (m, 4H), 1.40 (s, 9H), 1.33 (d, J=4.8 Hz, 3H), 1.28-1.23 (m, 3H), 1.08-1.02 (m, 42H), 1.01 (s, 6H), 0.94 (d, J=2.1 Hz, 6H); $^{13}$C NMR (101 MHz, CDCl$_3$) δ 172.4, 171.0, 170.9, 159.5, 155.8, 150.9, 150.7, 142.8, 136.9, 136.8, 135.3, 135.1, 134.13, 134.05, 133.86, 133.85, 133.78, 131.2, 131.1, 129.42, 129.37, 129.0, 126.4, 126.2, 125.5, 125.2, 122.5 (2C), 121.8, 119.3, 118.4, 116.8 (2C), 116.6 (2C), 115.4, 115.3, 114.71, 114.66, 106.4, 102.3, 102.2, 84.8, 80.7, 80.6, 79.9, 79.8, 79.3, 76.2, 74.32, 74.30, 72.9, 60.38, 60.35, 60.0, 59.9, 55.72, 55.71, 52.0, 46.6, 46.2, 45.9, 44.84, 44.77, 42.99, 42.96, 42.4, 41.2, 33.53, 33.49, 32.6, 32.5, 30.3, 28.4, 27.3 (2C), 27.17, 27.16, 27.1, 25.4, 18.1 (12C), 14.2, 14.1, 11.91 (3C), 11.90 (3C); HRMS (ESI$_+$) m/z calcd for C$_{94}$H$_{135}$Cl$_4$F$_3$N$_7$O$_{20}$Si$_2$ [M+H] 1934.8007, found: 1934.8021.

Step 2

To a stirred solution of 24 (15.4 mg, 8.0 µmol) in EtOH/H$_2$O (9:1, 0.5 mL) were added HgCl$_2$ (4.3 mg, 0.016 mmol) and acetaldoxime (4.9 µL, 0.080 mmol) at rt. After being stirred for 6 h at rt, the reaction mixture was concentrated under reduced pressure. The residue was quenched with saturated NaHCO$_3$ aq., extracted with CHCl$_3$. The combined organic extracts were dried over Na$_2$SO$_4$ and concentrated in vacuo. The crude product was purified by silica gel column chromatography (CHCl$_3$/MeOH 99.5:0.5 to 99.2:0.8 to 98.8:1.2) to afford 25 (15.3 mg, 7.8 µmol, 98%): TLC (CHCl$_3$/MeOH 95:5) R$_f$=0.30; [α]$^{21}_D$+0.144 (c=0.53, CHCl$_3$); IR (thin film) v$_{max}$=3335 (br), 2940, 2866, 1719, 1676, 1505, 1464, 1367, 1242, 1162, 1101, 1070, 882, 681 cm$^{-1}$; $^1$H NMR (400 MHz, CDCl$_3$) δ 7.53 (dd, J=8.6, 5.1 Hz, 1H), 7.30 (s, 1H), 7.28-7.22 (m, 2H), 7.21-7.12 (m, 6H), 6.91 (d, J=8.5 Hz, 4H), 6.86 (d, J=2.6 Hz, 2H), 6.51 (d, J=8.7 Hz, 1H), 5.94 (brs, 1H), 5.79-5.67 (m, 3H), 5.56-5.47 (m, 2H), 5.17 (brs, 1H), 5.06 (s, 1H), 4.96 (brs, 1H), 4.82-4.73 (m, 2H), 4.43 (tt, J=7.8, 3.8 Hz, 1H), 4.39-4.28 (m, 3H), 4.21 (brs, 1H), 4.13 (brs, 1H), 3.78 (s, 3H), 3.73 (q, J=7.4 Hz, 5H), 3.67 (brs, 1H), 3.48 (ddd, J=11.7, 7.2, 3.7 Hz, 2H), 3.41-3.28 (m, 1H), 3.17 (s, 1H), 3.09 (ddd, J=12.2, 8.2, 3.3 Hz, 2H), 2.80-2.60 (m, 2H), 2.38-2.15 (m, 7H), 2.13-2.05 (m, 2H), 1.93 (ddd, J=12.8, 8.0, 3.7 Hz, 2H), 1.85-1.79 (m, 2H), 1.54 (s, 3H), 1.42 (s, 9H), 1.34 (s, 3H), 1.04 (d, J=2.8 Hz, 42H), 1.01 (s, 6H), 0.96 (s, 6H); $^{13}$C NMR (101 MHz, CDCl$_3$) δ 162.1, 162.0, 159.6, 159.5, 156.2, 155.8, 150.9, 150.4, 142.80, 142.78, 136.88, 136.86, 135.23, 135.21, 133.9, 133.6, 131.33, 131.30, 131.29, 129.40, 129.37, 129.2, 129.1, 129.02, 128.98, 126.24, 126.22, 126.21, 125.40, 125.36, 124.5, 124.4, 123.20, 123.19, 122.5 (2C), 121.8, 120.1, 119.3, 116.8 (2C), 115.4, 80.4, 80.02, 79.99, 79.96, 79.95, 79.92, 79.87, 79.85, 79.83, 74.51, 74.50, 72.7, 70.4, 70.3, 69.5, 60.0, 59.9, 55.73, 55.72, 46.7, 46.19, 46.15, 46.13, 46.11, 46.10, 46.07, 46.0, 44.8, 34.7, 34.5, 32.61, 32.58, 30.2, 29.7, 29.64, 29.60, 28.50, 28.45, 28.42, 28.38, 28.34, 27.25 (2C), 27.19, 27.16, 25.31, 25.29, 25.27, 18.1 (12C), 14.1, 12.2, 11.9 (6C); HRMS (ESI$_+$) m/z calcd for C$_{94}$H$_{137}$Cl$_4$F$_3$N$_7$O$_{21}$Si$_2$ [M+H] 1952.8112, found: 1952.8098.

Step 3

To a stirred solution of 25 (5.3 mg, 2.7 µmol) in CH$_2$Cl$_2$ (0.70 mL) was added TFA (0.30 mL). The reaction mixture was stirred for 1 h at rt, and all volatile solvents were evaporated in vacuo. To a stirred solution of the crude mixture in H$_2$O (0.2 mL) was added TFA (0.8 mL). The reaction mixture was stirred for 2 h at 40° C., and all volatile solvents were evaporated in vacuo. The crude mixture was purified by silica gel column chromatography (CHCl$_3$/MeOH 80:20 to CHCl$_3$/MeOH/H$_2$O/50% aqueous ammonia 56:42:7:3) to afford 11 (2.2 mg, 2.5 µmol, 91%): TLC (n-butanol/ethanol/CHCl$_3$/28% aqueous ammonia 4:7:2:7) R$_f$=0.50; [α]$^{21}_D$+0.375 (c=0.30, methanol); IR (thin film) v$_{max}$=3352 (br), 2932, 1677, 1505, 1243, 1201, 1136, 801, 722 cm$^{-1}$; $^1$H NMR (400 MHz, CD$_3$OD) δ 7.78 (d, J=8.1 Hz, 1H), 7.18 (dd, J=9.0, 3.5 Hz, 4H), 7.00 (dd, J=16.0, 8.6 Hz, 4H), 5.77 (d, J=2.9 Hz, 1H), 5.73 (d, J=8.1 Hz, 1H), 5.14 (s, 1H), 4.57-4.50 (m, 1H), 4.28 (s, 2H), 4.22-4.13 (m, 3H), 4.10 (dd, J=8.6, 4.4 Hz, 1H), 4.07-3.98 (m, 2H), 3.52-3.46 (m, 3H), 3.44 (d, J=8.8 Hz, 1H), 3.17 (d, J=13.0 Hz, 1H), 3.14-3.02 (m, 3H), 2.60 (ddq, J=18.4, 11.8, 6.9 Hz, 2H), 2.29 (td, J=7.3, 2.8 Hz, 2H), 2.12 (dd, J=14.5, 5.6 Hz, 2H), 1.93-1.73 (m, 4H), 1.39-1.25 (m, 2H); $^{13}$C NMR (101 MHz, CD$_3$OD) δ 175.6, 166.2, 157.6, 152.0, 142.6, 131.2, 129.6 (2C), 123.6 (2C), 118.11 (2C), 118.07 (2C), 110.5, 102.7, 92.3, 85.3, 81.4, 80.4, 76.5, 75.1, 74.1 (2C), 73.0, 71.3, 64.4, 43.7, 43.6, 34.7, 31.5, 26.9; HRMS (ESI$_+$) m/z calcd for C$_{39}$H$_{51}$F$_3$N$_7$O$_{13}$ [M+H] 882.3497, found: 882.3512.

Example 4: Synthesis of Compound 12

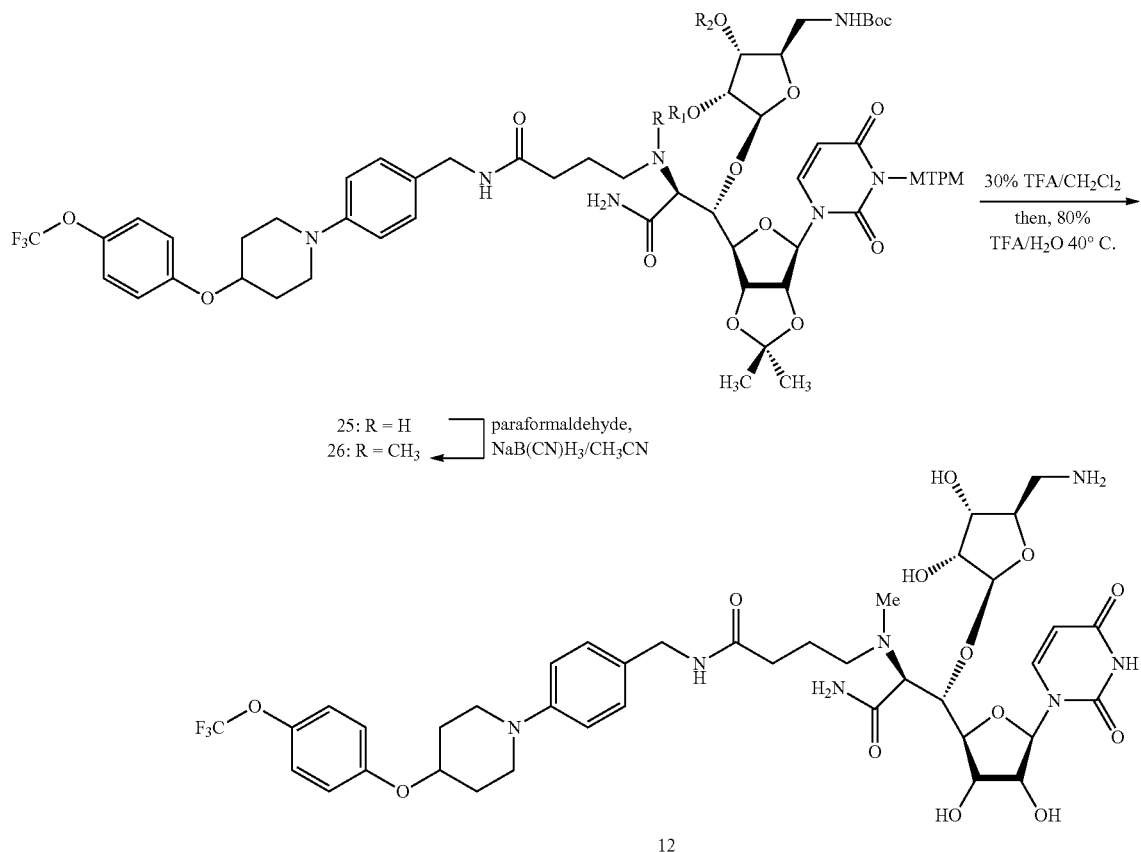

Step 1

To a stirred solution of 25 (7.8 mg, 4.0 μmol) and paraformaldehyde (3.6 mg, 0.12 mmol) in CH$_3$CN (0.5 mL) were added NaB(CN)H$_3$ (7.5 mg, 0.12 mmol). After being stirred for 17 h at rt, the reaction mixture was quenched with saturated NaHCO$_3$ aq. and extracted with CHCl$_3$. The combined organic extracts were dried over Na$_2$SO$_4$ and concentrated in vacuo. The crude product was purified by silica gel column chromatography (hexanes/EtOAc 33:67) to afford 26 (4.7 mg, 2.4 μmol, 59%): TLC (hexanes/EtOAc 20:80) R$_f$=0.50; $^1$H NMR (400 MHz, CDCl$_3$) δ 7.57 (d, J=8.8 Hz, 1H), 7.38 (dd, J=19.7, 7.9 Hz, 1H), 7.29 (s, 1H), 7.22-7.10 (m, 5H), 6.90 (d, J=9.1 Hz, 4H), 6.85 (d, J=3.6 Hz, 2H), 6.51 (d, J=5.1 Hz, 1H), 6.25 (d, J=27.7 Hz, 1H), 5.84 (dd, J=13.4, 8.0 Hz, 1H), 5.55 (s, 1H), 5.48 (brs, 1H), 5.13 (brs, 1H), 5.09 (s, 1H), 4.99 (brs, 1H), 4.86 (d, J=6.3 Hz, 1H), 4.74 (d, J=7.0 Hz, 1H), 4.43 (tt, J=7.5, 3.6 Hz, 1H), 4.36-4.28 (m, 4H), 4.20 (dd, J=8.6, 3.5 Hz, 1H), 3.77 (s, 3H), 3.74 (t, J=6.5 Hz, 4H), 3.69-3.63 (m, 2H), 3.51-3.42 (m, 4H), 3.29 (d, J=14.5 Hz, 1H), 3.08 (ddd, J=12.2, 8.4, 3.4 Hz, 2H), 2.76-2.68 (m, 1H), 2.61-2.51 (m, 1H), 2.45 (s, 3H), 2.29-2.14 (m, 5H), 2.12-2.05 (m, 2H), 1.96-1.83 (m, 4H), 1.55 (s, 3H), 1.39 (s, 9H), 1.37 (s, 3H), 1.26 (s, 3H), 1.04 (d, J=4.6 Hz, 42H), 1.01 (s, 6H), 0.99 (s, 6H); $^{13}$C NMR (101 MHz, CDCl$_3$) δ 173.0, 172.3, 171.22, 171.15, 162.0, 159.5, 157.5, 155.8, 150.6, 142.83, 142.81, 136.9, 135.4, 131.3, 129.36, 129.35, 129.31, 129.30, 129.03, 128.99, 128.95, 128.93, 126.1, 122.5 (2C), 116.8 (2C), 116.6, 115.33, 115.29, 107.3, 106.9, 84.1, 79.30, 79.28, 79.26, 79.24, 79.23, 74.88, 74.87, 73.6, 72.83, 72.80, 70.61, 70.56, 69.8, 67.3, 60.39, 60.36, 60.0, 59.9, 55.70 (2C), 54.2, 46.6 (2C), 46.1, 46.0, 45.0, 44.9, 44.7, 43.1, 41.2, 32.61, 32.59, 30.33 (2C), 30.27, 30.25, 29.69, 29.67, 29.65, 29.60, 28.52, 28.45, 27.31, 27.28, 27.24, 27.23, 27.22, 27.15, 25.14, 25.11, 22.7, 18.1 (12C), 14.2, 14.1, 11.9 (6C); HRMS (ESI$_+$) m/z calcd for C$_{95}$H$_{139}$Cl$_4$F$_3$N$_7$O$_{21}$Si$_2$ [M+H] 1966.8269, found: 1966.8288.

Step 2

To a stirred solution of 26 (4.7 mg, 2.4 μmol) in CH$_2$Cl$_2$ (0.70 mL) was added TFA (0.30 mL). The reaction mixture was stirred for 2 h at rt, and all volatile solvents were evaporated in vacuo. To a stirred solution of the crude mixture in H$_2$O (0.2 mL) was added TFA (0.8 mL). The reaction mixture was stirred for 4 h at 40° C., and all volatile solvents were evaporated in vacuo. The crude mixture was purified by silica gel column chromatography (CHCl$_3$/MeOH 80:20 to CHCl$_3$/MeOH/H$_2$O/50% aqueous ammonia 56:42:7:3) to afford 12 (2.0 mg, 2.2 μmol, 92%): TLC (n-butanol/ethanol/CHCl$_3$/28% aqueous ammonia 4:7:2:7) R$_f$=0.55; [α]$^{20}_D$+0.246 (c=0.24, methanol); IR (thin film) v$_{max}$=3276 (br), 2933, 1675, 1505, 1465, 1271, 1243, 1199, 1111 cm$^{-1}$; $^1$H NMR (400 MHz, CD$_3$OD) δ 7.84 (d, J=7.7 Hz, 1H), 7.19 (dd, J=8.5, 3.3 Hz, 4H), 7.01 (dd, J=13.1, 8.6 Hz, 4H), 5.86 (d, J=7.8 Hz, 1H), 5.73 (d, J=2.4 Hz, 1H), 5.16 (s, 1H), 4.54 (tt, J=7.3, 3.1 Hz, 1H), 4.30-4.25 (m, 3H), 4.26 (d, J=9.2 Hz, 1H), 4.22-4.05 (m, 6H), 3.70 (d, J=9.2 Hz, 1H), 3.52-3.44 (m, 2H), 3.09 (ddt, J=12.3, 8.6, 4.3 Hz, 2H), 2.91-2.82 (m, 1H), 2.58-2.53 (m, 1H), 2.50 (s, 3H), 2.30 (q, J=6.9 Hz, 2H), 2.15-2.08 (m, 2H), 1.96-1.82 (m, 3H), 1.81-1.71 (m, 1H), 1.39-1.25 (m, 2H); $^{13}$C NMR (101 MHz, CD$_3$OD) δ 175.3, 172.2, 157.6, 152.0, 142.4, 131.3, 129.7 (2C), 123.6 (2C), 118.12 (2C), 118.08 (2C), 111.9, 92.1, 84.4, 80.3, 78.4, 76.4, 75.4, 74.1 (2C), 71.5, 70.8, 68.3, 43.7, 39.7, 34.5, 31.5 (2C), 24.5; HRMS (ESI$_+$) m/z calcd for C$_{40}$H$_{53}$F$_3$N$_7$O$_{13}$ [M+H] 896.3653, found: 896.3640.

Example 6: Synthesis of Compound 8
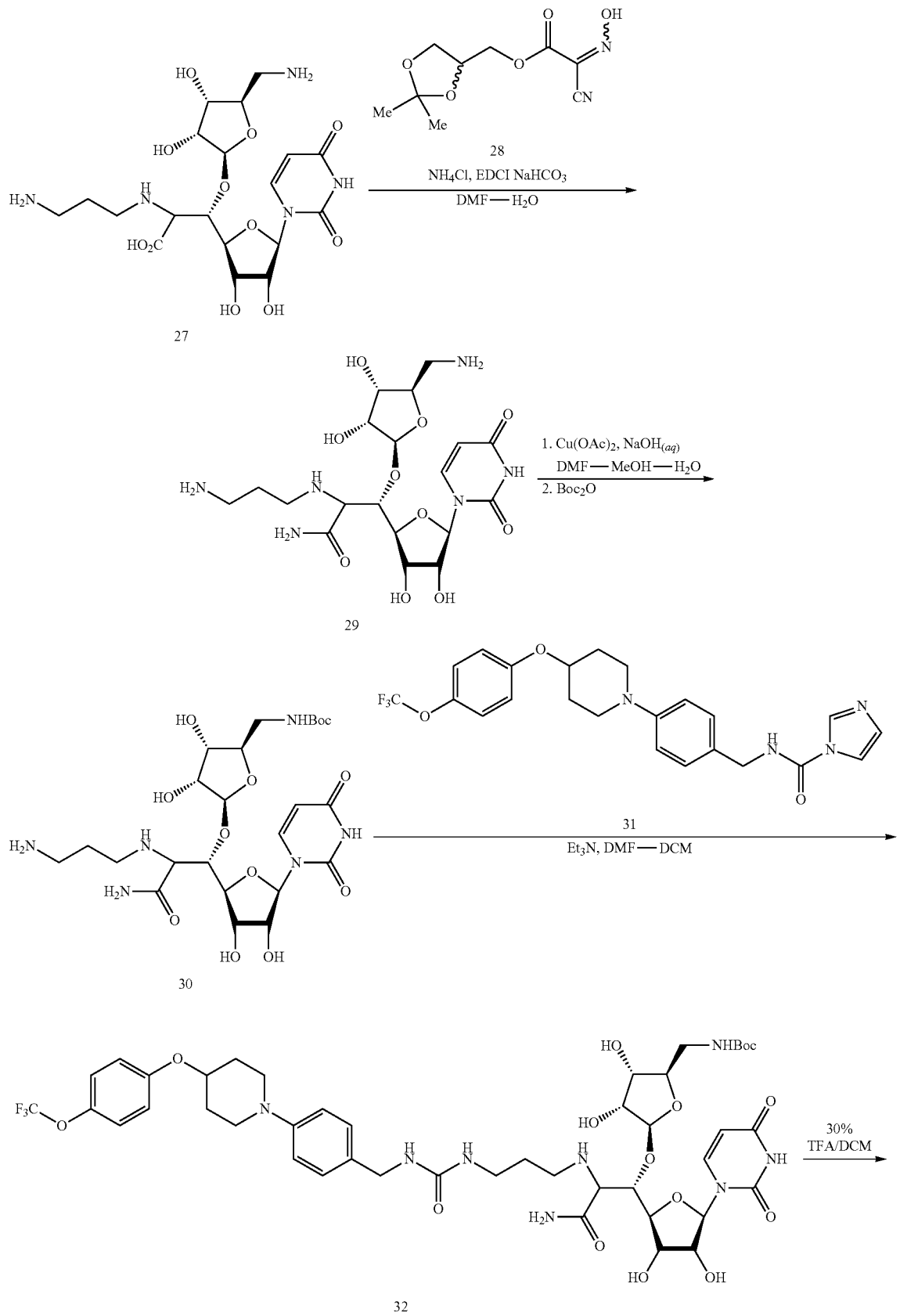

-continued

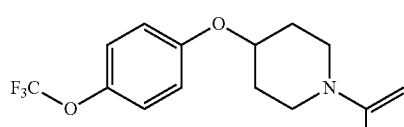 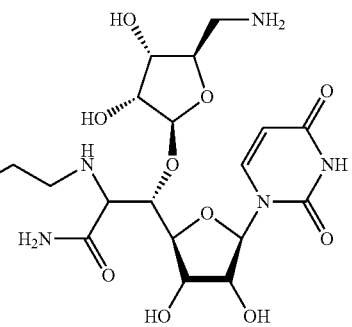

8

Step 1

To a stirred solution of 27 (32 mg, 0.06 mmol), NH$_4$Cl (0.17 g, 3.17 mmol), NaHCO$_3$ (80 mg, 0.95 mmol) and 28 (72 mg, 0.32 mmol) in DMF/H$_2$O (9:1, 0.60 mL) was added EDCl (61 mg, 0.32 mmol). The reaction mixture was stirred for 8 h at rt, filtered and concentrated in vacuo. The crude mixture was purified by C18 reverse-phase HPLC [column: Luna® (100 Å, 10 μm, 250×10 mm), solvents: 5:95 MeOH: 0.05M NH$_4$HCO$_3$ in H$_2$O, flow rate: 3.0 mL/min, UV: 254 nm] to afford 29 (30 mg, 0.061 mmol, 95%, retention time: 6.7 min): TLC (n-butanol/ethanol/CHCl$_3$/28% aqueous ammonia 4:7:2:7) R$_f$=0.10; [α]$^{22}_D$+0.168 (c=0.26, methanol); IR (thin film) ν$_{max}$=3298 (br), 2923, 2852, 1677, 1632, 1464, 1405, 1272, 1112, 1061 cm$^{-1}$; $^1$H NMR (400 MHz, D$_2$O) δ 7.70 (d, J=8.1 Hz, 1H), 5.84 (d, J=8.0 Hz, 1H), 5.72 (d, J=2.7 Hz, 1H), 5.18 (s, 1H), 4.37 (dd, J=5.6, 2.8 Hz, 1H), 4.26 (t, J=6.5 Hz, 2H), 4.20 (dd, J=7.5, 4.8 Hz, 1H), 4.13-4.06 (m, 3H), 3.94-3.75 (m, 1H), 3.31 (d, J=13.4 Hz, 1H), 3.12-3.06 (m, 1H), 3.01 (dt, J=6.9, 3.4 Hz, 2H), 2.95-2.83 (m, 1H), 2.83-2.68 (m, 1H), 1.93-1.80 (m, 2H); $^{13}$C NMR (101 MHz, D$_2$O) δ 166.19, 163.11, 162.76, 151.29, 142.38, 108.44, 101.89, 91.71, 83.25, 78.45, 74.44, 72.81, 71.54, 69.33, 62.08, 44.89, 42.07, 37.52; HRMS (ESI$_+$) m/z calcd for C$_{19}$H$_{33}$N$_6$O$_{10}$ [M+H] 505.2258, found: 505.2272.

Step 2

To a stirred solution of 29 (8.1 mg, 0.016 mmol), Cu(OAc)$_2$ (1.0 M in H$_2$O, 0.048 mL, 0.048 mmol), and NaOH (1.0 M in H$_2$O, 0.048 mL, 0.048 mmol) in H$_2$O-MeOH-DMF (1:1:1, 0.6 mL) was added Boc$_2$O (8.7 mg, 0.040 mmol). The reaction mixture was stirred for 4 h at rt, filtered and concentrated in vacuo. The crude mixture was purified by C18 reverse-phase HPLC [column: Luna® (100 Å, 10 μm, 250×10 mm), solvents: 25:75 MeOH:0.05M NH$_4$HCO$_3$ in H$_2$O, flow rate: 3.0 mL/min, UV: 254 nm] to afford 30 (8.8 mg, 0.015 mmol, 91%, retention time: 13.0 min): TLC (CHCl$_3$/MeOH/H$_2$O/28% aqueous ammonia 56:42:7:3) R$_f$=0.10; IR (thin film) ν$_{max}$=3329 (br), 3312 (br), 2979, 2929, 1678, 1572, 1508, 1459, 1392, 1367, 1279, 1131, 1115, 1077, 1057, 1018 cm$^{-1}$; $^1$H NMR (400 MHz, D$_2$O) δ 7.76 (d, J=7.8 Hz, 1H), 5.79 (s, 1H), 5.76 (d, J=7.8 Hz, 1H), 5.05 (s, 1H), 4.25-4.13 (m, 3H), 4.03 (dd, J=10.5, 6.8 Hz, 3H), 3.52 (d, J=6.4 Hz, 1H), 3.36-3.31 (m, 2H), 3.29 (s, 1H), 2.97 (t, J=7.3 Hz, 2H), 2.65 (t, J=7.1 Hz, 2H), 1.82-1.73 (m, 2H), 1.34 (s, 9H); $^{13}$C NMR (101 MHz, D$_2$O) δ 176.10, 161.92, 161.73, 160.96, 146.67, 140.44, 109.60, 102.04, 90.59, 90.39, 82.37, 81.77, 80.86, 79.92, 75.26, 74.88, 41.07, 38.32, 38.19, 27.69 (3C); HRMS (ESI$_+$) m/z calcd for C$_{24}$H$_{41}$N$_6$O$_{12}$ [M+H] 605.2782, found: 605.2795.

Step 3

To a stirred solution of 30 (4.3 mg, 7.1 μmol) and 31 (9.8 mg, 0.021 mmol) in DMF-CH$_2$Cl$_2$ (1:1, 0.2 mL) was added Et$_3$N (4.7 μL, 0.036 mmol) at rt. The reaction mixture was stirred for 12 h at rt, and all volatile solvents were evaporated in vacuo. The crude mixture was passed through a silica gel column chromatography (EtOAc to CHCl$_3$/MeOH/H$_2$O/28% aqueous ammonia 56:42:7:3) to afford 32 (6.4 mg, 6.4 μmol, 90%). TLC (CHCl$_3$/MeOH/H$_2$O/28% aqueous ammonia 56:42:7:3) R$_f$=0.55; [α]$^{21}_D$+0.086 (c=0.17, methanol); IR (thin film) ν$_{max}$=3325 (br), 2930, 2855, 1678, 1553, 1505, 1267, 1242, 1197, 1163, 1113, 1033 cm$^{-1}$; $^1$H NMR (400 MHz, MeOD) δ 7.92 (d, J=8.0 Hz, 1H), 7.21-7.16 (m, 4H), 7.01-6.95 (m, 6H), 5.82 (s, 1H), 5.75 (d, J=8.1 Hz, 1H), 5.10 (s, 1H), 4.53 (dd, J=7.8, 4.0 Hz, 2H), 4.34 (s, 1H), 4.26 (s, 2H), 4.22 (s, 1H), 4.19-4.15 (m, 2H), 4.06 (d, J=4.5 Hz, 1H), 3.98-3.94 (m, 2H), 3.93 (s, 1H), 3.52-3.44 (m, 4H), 3.26-3.20 (m, 1H), 3.08 (ddd, J=12.2, 8.6, 3.1 Hz, 4H), 2.15-2.06 (m, 2H), 1.91-1.82 (m, 2H), 1.44 (s, 9H); $^{13}$C NMR (101 MHz, MeOD) δ 173.09, 172.96, 158.76, 157.79, 157.63, 152.17, 152.09, 131.12, 130.54 (2C), 130.43, 129.63 (2C), 129.23, 123.85, 123.58, 121.89, 120.53, 120.32, 118.20, 118.11 (2C), 118.02, 117.15 (2C), 76.68, 74.01, 73.34, 71.10, 43.80, 31.62, 31.49, 28.89 (3C), 28.75, 23.77, 22.54; HRMS (ESI$_+$) m/z calcd for C$_{44}$H$_{60}$F$_3$N$_8$O$_{15}$ [M+H] 997.4130, found: 997.4168.

Step 4

To a stirred solution of 32 (6.4 mg, 6.4 μmol) in CH$_2$Cl$_2$ (0.35 mL) was added TFA (0.15 mL). The reaction mixture was stirred for 3 h at rt, and all volatile solvents were evaporated in vacuo. The crude mixture was purified by DOWEX (50 W×4) ion exchange resin. The resin was washed with MeOH/H$_2$O (4:1) and MeOH. The crude product (TFA salt) was dissolved in MeOH (10 mL) and absorbed on DOWEX (50 W×4). The resins were washed with MeOH and eluted with MeOH/50% aqueous ammonia (10:1). The eluent was concentrated under reduced pressure and the resultant aqueous solution was lyophilize to afford 8 (5.7 mg, 6.4 μmol, 100%): TLC (CHCl$_3$/MeOH/H$_2$O/28% aqueous ammonia 56:42:7:3) R$_f$=0.35; [α]$^{20}_D$+0.037 (c=0.05, methanol); IR (thin film) ν$_{max}$=3310 (br), 3077, 2928, 2853, 1649, 1614, 1555, 1515, 1504, 1267, 1241, 1222, 1196, 1162, 1112, 1037, 1029 cm$^{-1}$; $^1$H NMR (400 MHz, MeOD) δ 7.84 (d, J=8.1 Hz, 1H), 7.22-7.15 (m, 4H), 7.06-6.96 6.96 (m, 6H), 5.79 (s, 1H), 5.74 (d, J=8.1 Hz, 1H), 5.13 (s, 1H), 4.58-4.51 (m, 2H), 4.26 (s, 1H), 4.23-4.20 (m, 1H), 4.19-4.14 (m, 2H), 4.10 (d, J=4.4 Hz, 1H), 3.97-3.94 (m, 1H), 3.47 (d, J=10.7 Hz, 2H), 3.40 (d, J=5.0 Hz, 1H), 3.23 (t, J=6.7 Hz, 2H), 3.07 (ddd, J=12.5, 8.5, 3.6 Hz, 2H), 2.90 (dd, J=13.3, 3.8 Hz, 1H), 2.80 (dd, J=13.3, 7.2 Hz, 1H), 2.70-2.55 (m, 2H), 2.17-2.05 (m, 2H), 1.92-1.82 (m, 2H), 1.69-1.60 (m, 2H); $^{13}$C NMR (101 MHz, MeOD) δ 158.76, 157.63, 152.09, 143.91, 131.12, 130.54 (2C), 130.43, 129.63 (2C), 129.24, 123.85, 123.59, 121.89, 120.53, 120.32, 118.19, 118.11 (2C), 118.03, 117.16 (2C), 102.63, 76.69, 74.01, 73.35, 43.80, 31.62, 31.49, 28.92, 22.53; HRMS (ESI$_+$) m/z calcd for $C_{39}H_{52}F_3N_8O_{13}$ [M+H] 897.3606, found: 897.3629.

Example 5: Enzyme Inhibition

Spore preparation. *C. difficile* (ATCC43596) was inoculated on a BHI agar plate and incubated at 37° C. under anaerobic condition for 7 days. The spores were collected from the agar using sterile distilled water, and purified according to the procedures described in the literature. The vegetative forms of *C. difficile* were killed upon heating at 50° C. for 30 min. The prepared spores were suspended in sterile distilled water at 4° C.

Minimum Inhibitory Concentration Assays. A single colony of *C. difficile* (ATCC43596) was grown on a BHI agar plate. Seed cultures and larger cultures were obtained using a BHI broth. The flasks were incubated anaero-bically for 48 h at 37° C. and cultured to mid-log phase (OD600 0.4). The inhibitors were dissolved in Polyethylene Glycol 300-H$_2$O (1/1, a final concentration of 1 mg per 100 μL). This concentration was used as the stock solution for all studies. Bacterial cultures were treated with serial dilutions of inhibitors and incubated at 37° C. for 48 h. MIC was determined by a 96-well plate reader (Biotek Synergy XT (Winooski, VT, USA) at 570 nm and 600 nm. If necessary, viable bacteria in each well (96-well plate) were measured via colony-forming unit (CFU) on a BHI agar plate. The absorbance measurements were also performed using a Biotek Synergy XT (Winooski, VT, USA), 96-well plate reader at 570 nm and 600 nm.

Spore viability testing. A solution of test compound was added to a suspension containing *C. difficile* spores (2×105 mL$^{-1}$), and the mixture was incubated at 37° C. for 24 h. The spore suspension treated with test compound was centrifuged (×4,700 g) and the pellet was washed with sterile distilled water, and plated on a BHI agar containing 0.1% sodium taurocholate (a germination agent) and incubated at 37° C. for 48 h under anaerobic conations. The resulting colonies were counted.

WecA Assay. UDP-Glucosamine-C6-FITC (2 mM stock solution, 0.56 L), MgCl$_2$ (0.5 M, 4 μL), β-mercaptoethanol (50 mM, 5 μL), CHAPS (5%, 11.25 μL), Tris buffer (pH 8.0, 50 mM), undecaprenyl phosphate (4 mM, 1.4 μL), and inhibitor molecule (0-100 μg/mL in Tris buffer) were place in a 500 μL Eppendorf tube. To a stirred reaction mixture, P-60 (10 μL) was added (total volume of reaction mixture: 50 μL adjust with Tris buffer). The reaction mixture was incubated for 4 h at 37° C. and quenched with n-butanol (150 μL). Two phases were mixed via vortex and centrifuged at 10,000×g for 3 min. The upper organic phase was assayed via reverse-phase HPLC. The organic phase (30 μL) was injected into HPLC (solvent: gradient elution of 85:15 to 95:5 MeOH/0.05 M aq. NH$_4$HCO$_3$; UV: 485 nm; flow rate: 0.5 ml/min; column: Kinetex 5 μm C8, 100 Å, 150×4.60 mm), and the area of the peak for C55-P-P-glucosamine-C6-FITC was quantified to obtain the IC$_{50}$ value. The IC$_{50}$ values were calculated from plots of the percentage product inhibition versus the inhibitor concentration.

MraY Assay. Park's nucleotide-N$^\varepsilon$-C6-dansyl (2 mM stock solution, 1.88 μL), MgCl$_2$ (0.5 M, 5 L), KCl (2 M, 5 μL), Triton X-100 (0.5%, 5.63 μL), Tris buffer (pH 8.0, 50 mM), neryl phosphate (0.1 M, 2.25 μL), and inhibitor molecule (0-100 μg/mL in Tris buffer) were placed in a 500 μL Eppendorf tube. To a stirred reaction mixture, P-60 (10 μL) was added (total volume of reaction mixture: 50 μL adjust with Tris buffer). The reaction mixture was incubated for 2 h at room temperature (26° C.) and quenched with CHCl$_3$ (100 μL). Two phases were mixed via vortex and centrifuged at 25,000×g for 10 min. The upper aqueous phase was assayed via reverse-phase HPLC. The water phase (10 μL) was injected into HPLC (solvent: CH3CN/ 0.05 M aq. NH$_4$HCO$_3$=25:75; UV: 350 nm; flow rate: 0.5 mL/min; column: Kinetex 5 μm C8, 100 Å, 150×4.60 mm), and the area of the peak for lipid I-neryl derivative was quantified to obtain the IC$_{50}$ value. The IC$_{50}$ values were calculated from plots of the percentage product inhibition versus the inhibitor concentration.

TABLE 1

| Compound | WecA inhibition IC$_{50}$ (μM) | MraY inhibition IC$_{50}$ (μM) | *C. difficile* ATCC43596 MIC (μg/mL) |
|---|---|---|---|
| FR-900493 (1) | 5 | 25 | >50 |
| 9 | 0.85 | 0.69 | 25 |
| 10 | 12.5 | 0.25 | 12.5 |
| 11 | 0.32 | 0.08 | 3.25 |
| 12 | 12.3 | 7.7 | 50 |
| Tunicamycin | 0.15 | 3.38 | >50 |

The IC$_{50}$ values of compounds 9-12 were measured in comparison to other known antibacterial agents (Table 1). Surprisingly, FR-900493 (1) exhibited a weak MraY inhibitory activity (IC$_{50}$ 25.0 μM), but a moderate WecA inhibitory activity (IC$_{50}$ 5.0 μM). The four compounds (9, 10, 11, and 12) were identified to display anti-*C. difficile* activity. The N-methyl analogs, 9 and 12, exhibited weak anti-*C. difficile* growth inhibitory activity, although their MraY inhibitory activity was over 30- and 3-fold more potent than that of FR-900493 (1). In sharp contrast, the de-N-methyl analogs, 10 and 11, were over-100 and 300-times more significant in the MraY inhibitory activity than 1. The WecA inhibitory activity of 11 was about 15-fold more significant than 1, however, the inhibition of the MraY enzyme could be attributed to anti-*C. difficile* activity; a weak WecA inhibitor 10 did exhibit a bactericidal activity against the vegetative state of *C. difficile*. Surprisingly, 11 was shown to be a very strong MraY/WecA inhibitor, whose activity was significantly better than tunicamycin, a known MraY/WecA inhibitor antibiotic. Anti-*C. difficile* activity is well-correlated with the enzyme inhibitory activity of MraY; 11 and 10 displayed the MIC value of 3.25 and 12.5 μg/mL, respectively against *C. difficile* (e.g. MICs 2.5 μg/mL for vancomycin).

Figure 3:
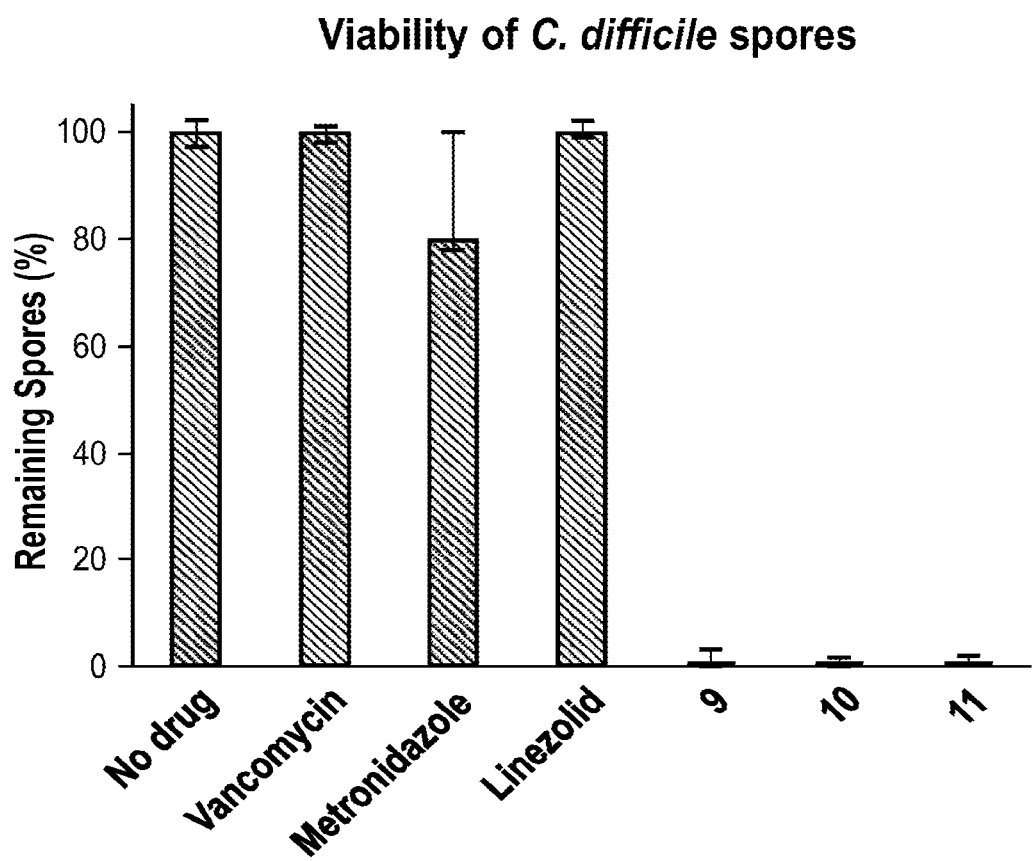
FIG. 3 shows the viability of *C. difficile* spores in the presence of the compounds of the invention and known antibacterial agents.

The effect of 9, 10, and 11 on *C. difficile* spores was determined by counting colony-forming units (CFUs) of the spore germination on the taurocholate-containing agar plates after the treatment of the *C. difficile* spores with these analogs (×2 MIC) for 24 hours. *C. difficile* spores show resistance to most known anti-*C. difficile* agents. Indeed, in these studies, vancomycin, metronidazole, and linezolid did not inhibit the spore germination even at ×5 MIC. On the contrary, the new MraY inhibitors 9, 10, and 11 caused loss of viability of *C. difficile* spores at ×2 MIC (FIG. 3).

Example 6: WecA Inhibition

Cytotoxicity Assays. Cytotoxicity assays were performed using Vero monkey kidney (ATCC CCL-81) and HepG2 human hepatoblastoma cell (ATCC HB-8065) lines. Vero or HepG2 cells were cultured in 75 cm$^2$ flasks and transferred to 96-well cell culture plates using ATCC-formulated Eagle's minimum essential medium containing 10% FBS, penicillin, and streptomycin. Serially diluted aliquots of each test compound at concentrations ranging from 0.78-200 μg/mL were added to the cells. Control compounds with known toxicity such as tunicamycin, colistin or tobramycin were included on each plate. The plates were incubated and cytotoxic effects were determined via the MTT assay.

AgIH Assay. AgIH assays were performed as the procedure described for WecA assays, but used MjAgIH and α-dihydroundecaprenyl phosphate instead of WecA and undecaprenyl phosphate.

TABLE 2

| Compound | WecA inhibition $IC_{50}$ (μM) | | AgIH inhibition $IC_{50}$ (μM) *M. jannaschii* AgIH | Vero cells $IC_{50}$ (μM) | Hemolysis $IC_{50}$ (μM) sheep blood |
|---|---|---|---|---|---|
| | *E. coli* WecA | *M. smegmatis* WecA | | | |
| 10 | 12.5 | 12.5 | 12.5 | 7.08 | 70 |
| 11 | 0.32 | 0.25 | 3.61 | 56.8 | 205.8 |
| Tunicamycin | 0.15 | 0.15 | 13.27 | 0.12 | 15 |

Figure 4:
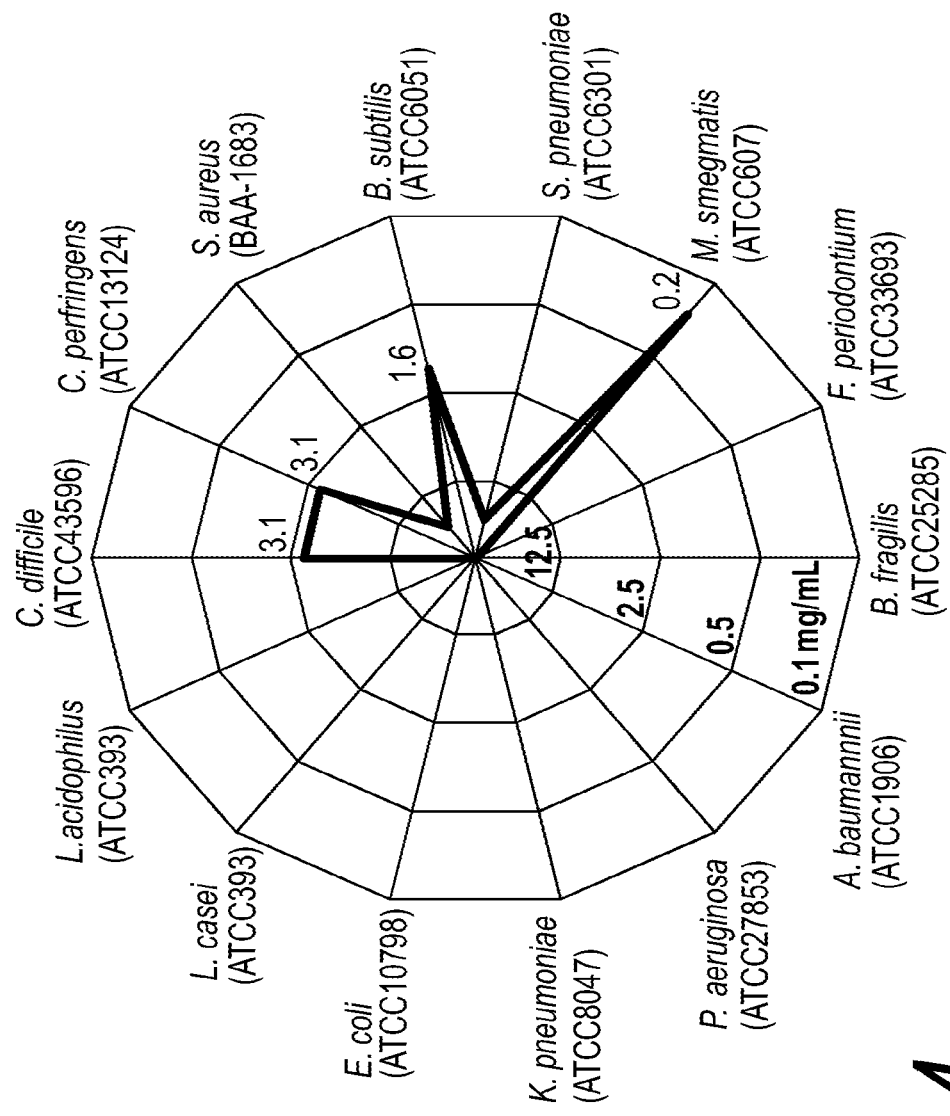
FIG. 4 shows the antibacterial activity of Compound 11.

Compound 11 exhibited superior physicochemical characteristics to the other compounds tested (Table 2); 1) water solubility of 11 (22 mg/mL) is 200-times greater than 10, 2) 11 exhibited approximately 450 times less cytotoxic than Tunicamycin against Vero cells ($IC_{50}$ 56.8 μM for 11 versus 0.12 μM for Tunicamycin), and 3) 11 showed relatively low induction of hemolysis ($IC_{50}$ 205.6 μM), whereas, Tunicamycin caused lysing of blood cells at a much lower concentration than 11. Interestingly, 11 exhibited a relatively stronger AgIH inhibitory activity ($IC_{50}$ 3.61 μM) than 10 and tunicamycin, however, the $IC_{50}$ level of 11 against Vero cells was significantly higher than those of 10 and tunicamycin. Compound 11 also displayed antibacterial activity against *C. difficile*, *C. perfringens*, and *B. subtilis* (red line in FIG. 4).

Example 7: Cytotoxicity Against Cancer Cells

Selected molecules were tested for cytotoxicity ($IC_{50}$) in cancer and healthy cells via a MTT colorimetric assay. The results are shown in Tables 3 and 4.

Cytotoxicity Assays. For Vero cells: Vero cell was cultured in Complete eagle's minimum essential growth medium (EMEM) containing L-glutamine, sodium pyruvate, minimum essential amino acids, penicillin-streptomycin and 10% fetal bovine serum. Inoculating number of cells were 400,000 cells/mL and a final 40,000 cells/well. After 72 h of exposure of molecules to this cell line at concentrations ranging from 0.78 to 200 μg/mL, the culture medium was changed to complete EMEM without phenol red before addition of yellow tetrazolium dye; MTT. Viability was assessed on the basis of cellular conversion of MTT into a purple formazan product. The absorbance of the colored formazan product was measured at 570 nm by BioTek Synergy HT Spectrophotometer. Linearity of the MTT response to the cell number was determined.

Each cell was cultured in recommended medium by ATCC, and the $IC_{50}$ data were obtained with each cell line.

TABLE 3

Cytotoxicity $IC_{50}$ (μM)

| Molecules | Cell Lines | | | | | |
|---|---|---|---|---|---|---|
| | L12210 | KB | LoVo | SK-OV-3 | MDA-MB-435S | Vero |
| Compound 11 | >100 | 7.09 | 0.22 | 2.85 | 7.09 | >65.0 |
| Tunicamycin | 1.7 | 2.5 | 1.7 | 1.85 | 0.9 | 0.12 |
| Mytomycin C | 25 | 9.34 | 0.3 | 18.7 | 4.7 | 4.67 |
| Taxol | 0.55 | 0.79 | 0.057 | 1.08 | 0.11 | 0.19 |

TABLE 4

Cytotoxicity $IC_{50}$ (μM)

| Molecules | Cell Lines | | | | | |
|---|---|---|---|---|---|---|
| | AsPc-1 | Panc-1 | HPAF-II | HCT 116 | HepG2 | Caco-2 |
| Compound 11 | 0.95 | <0.098 | <0.098 | 3.54 | >60 | >60 |
| Tunicamycin | 0.46 | 0.625 | <0.098 | 0.92 | 0.19 | 0.95 |
| Mytomycin C | 1.16 | — | — | 2.33 | 2.33 | 5.5 |
| Taxol | 0.19 | 0.02 | 0.02 | — | — | — |

Compound 11 exhibited strong cytotoxic activity in many of the cancer cell lines tested. Unlike the other compounds tested (Tunicamycin, Mytomycin C, and Taxol), 11 had little cytotoxic effects on healthy, non-cancerous Vero cells. Compound 11 also exhibited selective cytotoxicity for Panc-1 cells over healthy HPNE cells (>1:350, $IC_{50}$ HPNE/$IC_{50}$ Panc-1).

Figure 5:
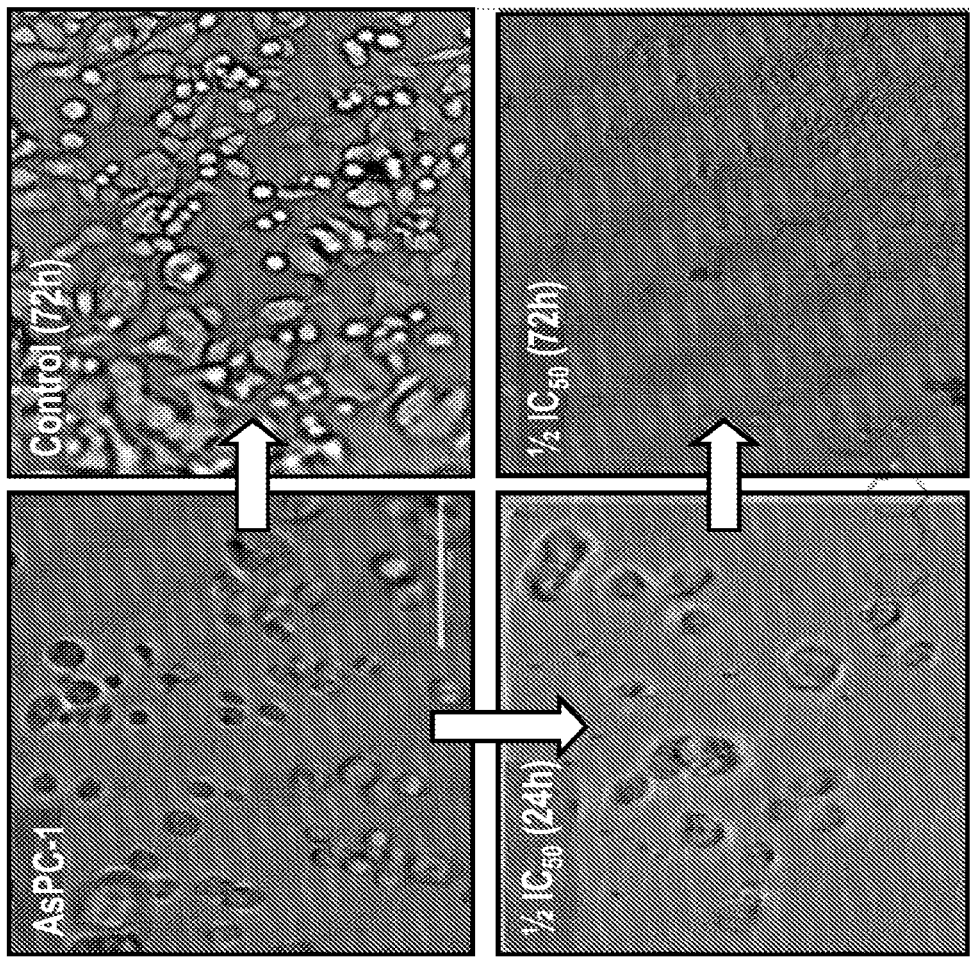
FIG. 5 shows AsPc-1 and Panc-1 cell viability assays of Compound 11
Figure 5:
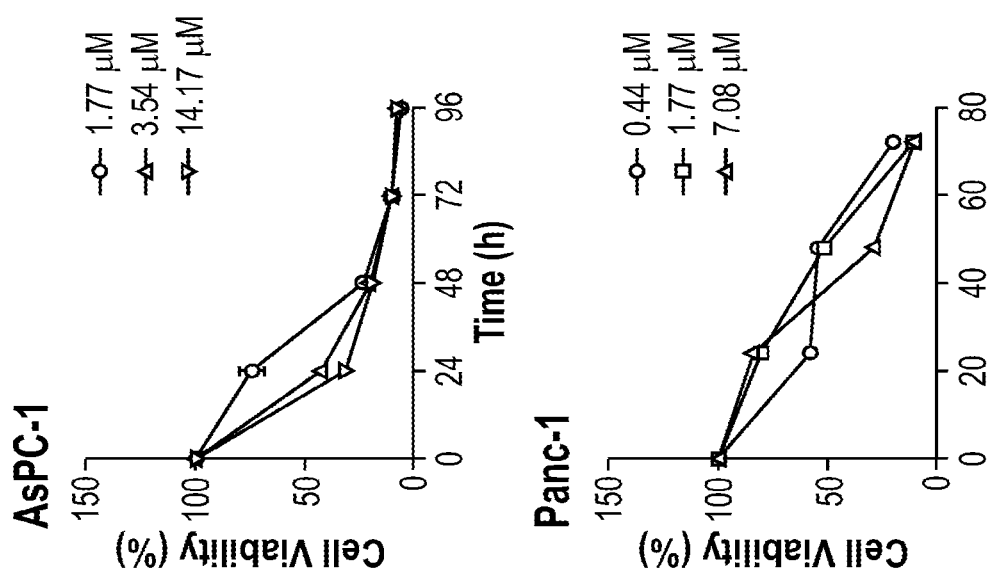

The cytotoxic activity of 11 against AsPc-1 and Panc-1 cells was also measured through cell viability assays (FIG. 5). Nearly all AsPc-1 cells were killed after 4 days in the presence of 11 at varying concentrations (1.77 μM, 3.54 μM, and 14.17 μM). Similarly, the percentage of viable Panc-1 cells was near-zero after about 3 days in the presence of 11 (0.44 μM, 1.77 μM, and 7.08 μM).

Figure 6:
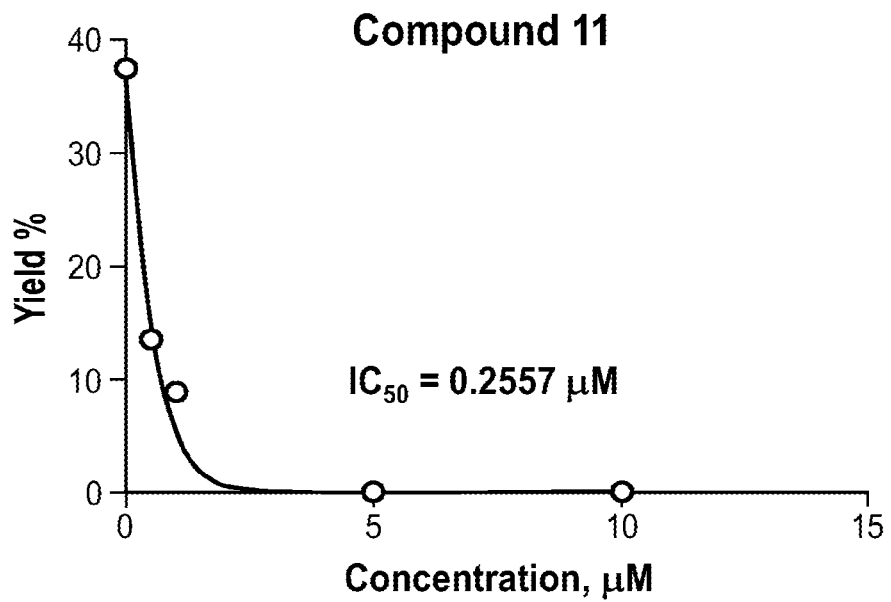
FIG. 6 shows western blow assays with β-catenin and DPAGT1 inhibition by Compound 11.
Figure 6:
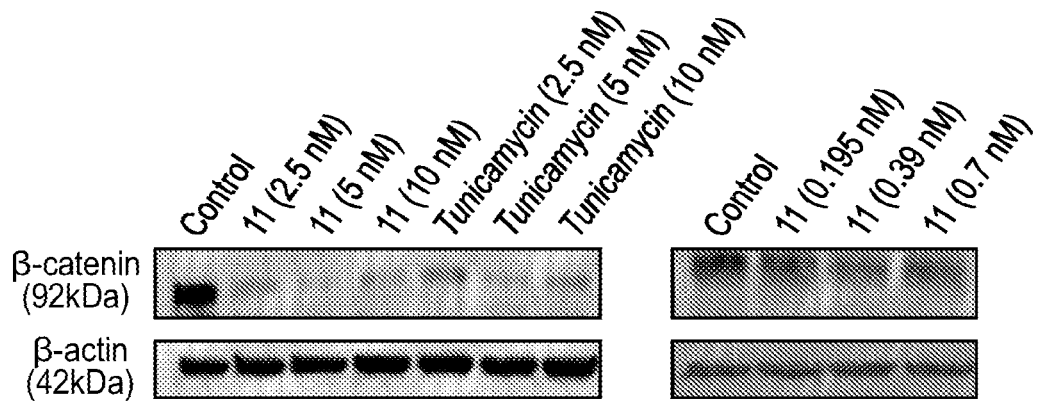

The anti-cancer effect of 11 is believed to be due to its ability of inhibit DPAGT1, an enzyme essential in glycoprotein biosynthesis, with an $IC_{50}$ value of 0.26 μM (FIG. 6). By inhibiting DPAGT1, N-glycosylation of β-catenin is also inhibited. β-Catenin overexpression is associated with many cancers, and 11 has been shown to inhibit N-glycosylation of β-catenin at concentrations as low as 0.39 nM. This DPAGT1 inhibition and subsequent N-glycosylation inhibition may provide further insights into the mechanism of action of the compounds of the invention.

Figure 7:
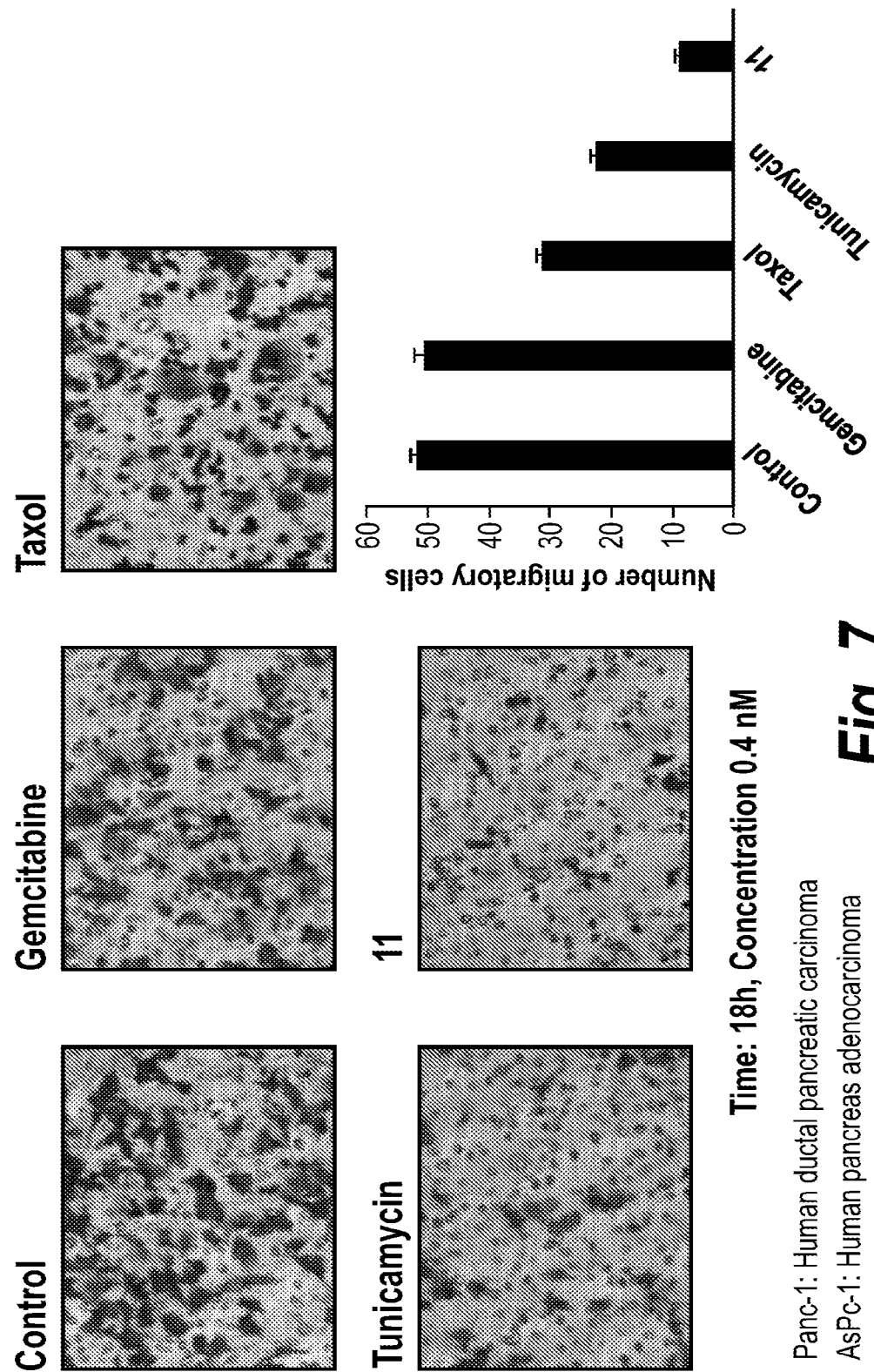
FIG. 7 shows Boyden Chamber Migration assays with Panc-1 cells with Gemcitabine, Taxol, Tunicamycin, and Compound 11.
Figure 8:
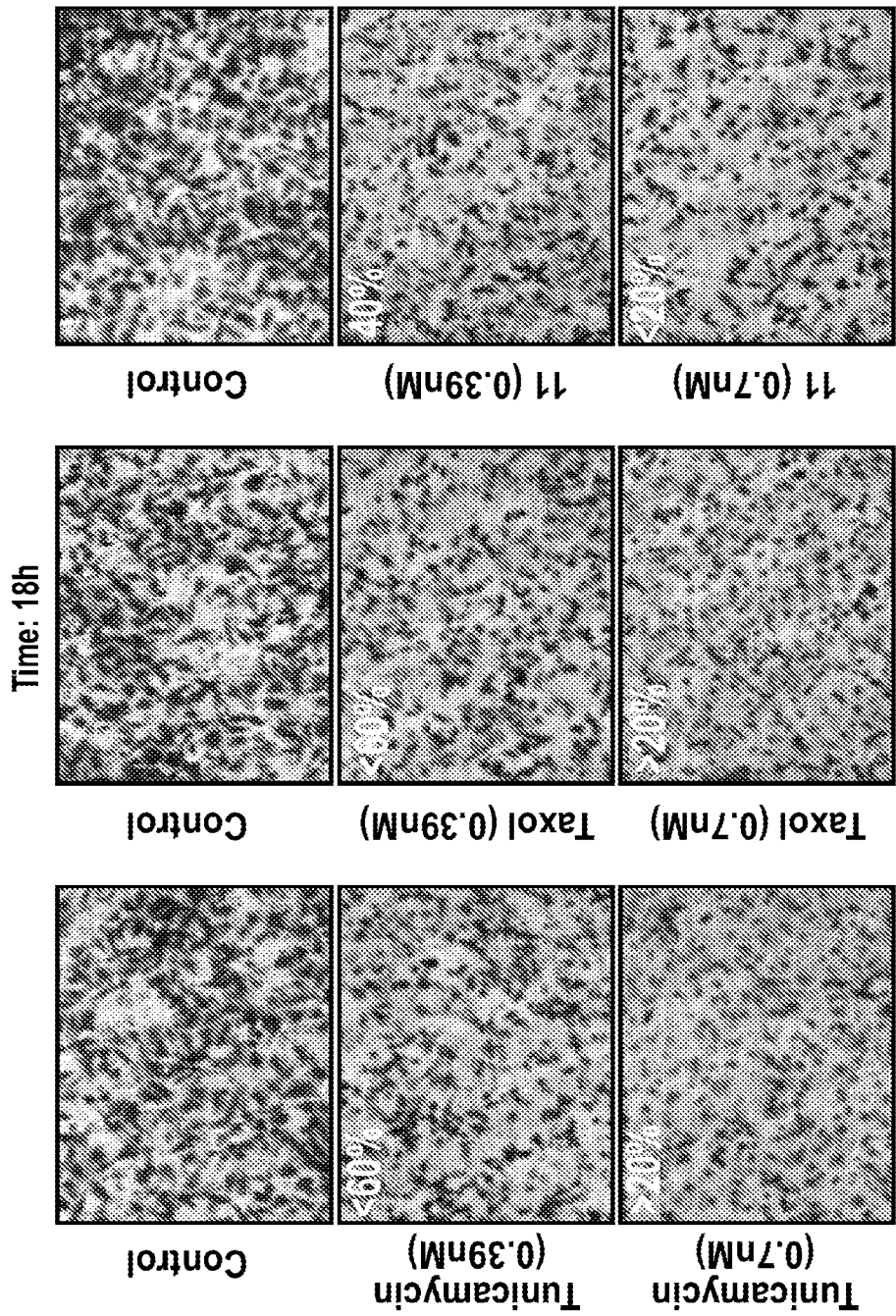
FIG. 8 shows Boyden Chamber Migration assays with AsPc-1 cells with Tunicamycin, Taxol, and Compound 11.
Figure 9:
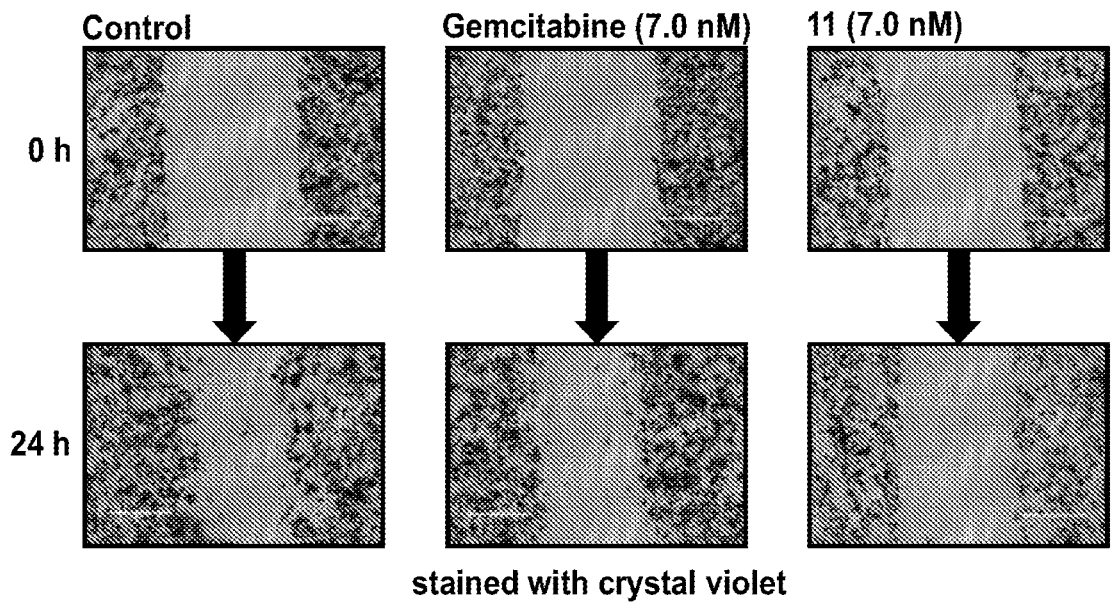
FIG. 9 shows scratch assays with AsPc-1 and Pac-1 cell lines in the presence of Gemcitabine and Compound 11.
Figure 9:
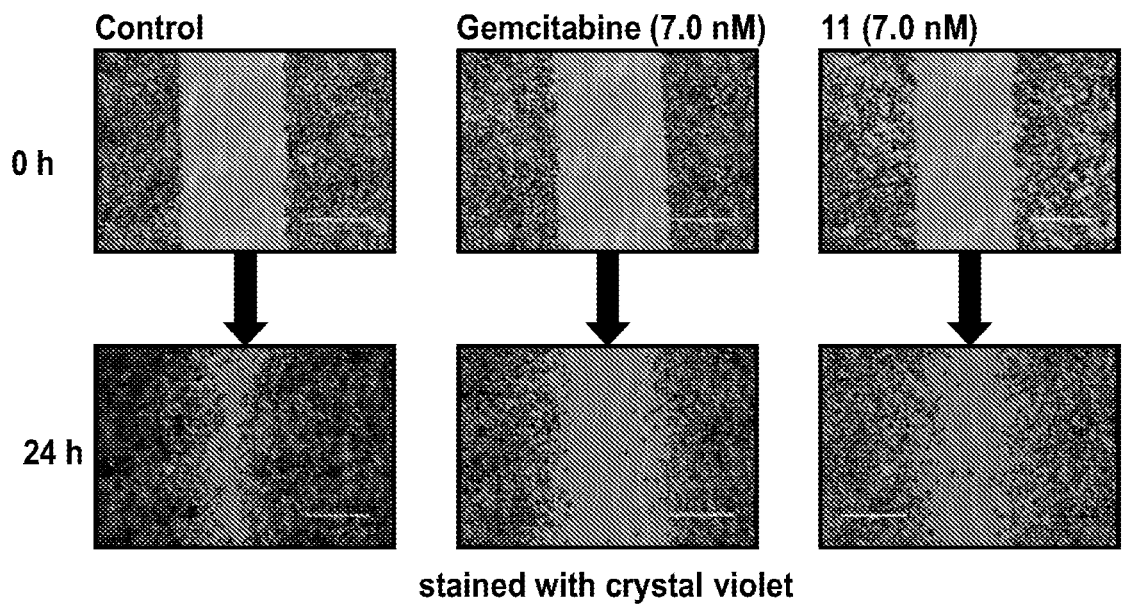

The cytotoxic activity of 11 against Panc-1 cells and AsPc-1 cells was also determined through Borden Chamber migration assays (FIGS. 7 and 8) and scratch (wound healing) assays (FIG. 9). Compound 11 resulted in fewer Panc-1 migratory cells than Gemcitabine, Taxol, and Tunicamycin (FIG. 7). Similar results were observed in AsPc-1 cells (FIG. 8). In scratch assays, treatment with 11 resulted in less AsPc-1 cell migration than Gemcitabine while Panc-1 cell migration was similar to that of Gemcitabine (FIG. 9).

Example 8: Synergistic Effects with Compound 11 and Paclitaxel (Taxol)

Synergistic Assay. The synergistic or antagonistic activities of 11 with other cancer drugs were assessed in vitro via micro dilution broth checkerboard technique previously reported. The FIC index was calculated according to the following equation. $\Sigma FIC = FIC_A + FIC_B = C_A/MIC_A + C_B/MIC_B$ where $MIC_A$ and $MIC_B$ are MIC of drugs A and B, $C_A$ and $C_B$ are the concentrations of drugs A and B used in combination. In these interaction studies, $\Sigma FIC$ of less than 0.5 represents synergistic activity. The results are shown in Table 5.

TABLE 5

| Entry | Combination of A and B | IC$_{50}$ A (nM) IC$_{50}$ B (nM) | C$_A$ and C$_B$ (nM) | Σ FIC |
|---|---|---|---|---|
| 1 | A: 11 | 982 | 14.2 | 0.224 |
|   | B: Paclitaxel | 550 | 0.4 | |
| 2 | A: 11 | 982 | 14 | 0.16 |
|   | B: Paclitaxel | 550 | 0.88 | |
| 3 | A: 11 | 982 | 14 | 0.27 |
|   | B: Paclitaxel | 550 | 7 | |
| 4 | A: 11 | 982 | 220 | 0.224 |
|   | B: Paclitaxel | 550 | 40 | |
| 5 | A: 11 | 982 | 110 | 0.114 |
|   | B: Paclitaxel | 550 | 88 | |

The FIC index is considered a good measure of synergy. An FIC value less than 0.5 indicates that the combination of compounds produces a synergistic effect which is more than the sum of the compounds' effects alone (i.e., more than an additive effect). Surprisingly, all five combinations of 11 and Taxol resulted in a synergistic effect. When combined with 11, Taxol could be used in concentrations as low as 7 nM to kill AsPc-1 cells.

These results may be beneficial from a clinical perspective. As shown in Table 3, 11 has little effect on healthy cells, whereas Taxol is toxic toward all dividing cells in the body regardless of whether the cells are cancerous or not. The results of the chemical combinations in Table 5 imply that Taxol may be used in lower concentrations to achieve the same degree of therapeutic effect, thus decreasing adverse effects typical of a cancer treatment with Taxol alone.

Example 8: Synergistic Effects with Compound 11 and Gemcitabine

The effect of treating AsPc-1 cells with various combinations of Compound 11 and Gemcitabine was measured. These experiments were performed in the same manner as those of Example 7. The results are shown in Tables 6 and 7.

TABLE 6

| Entry | Combination of A and B | IC$_{50}$ A (μM) IC$_{50}$ B (μM) | C$_A$ and C$_B$ (μM) | Σ FIC |
|---|---|---|---|---|
| 1 | A: 11 | 0.98 | 0.055 | 0.3 |
|   | B: Gemcitabine | 0.39 | 0.37 | |
| 2 | A: 11 | 0.98 | 0.22 | 0.47 |
|   | B: Gemcitabine | 0.39 | 0.37 | |

TABLE 7

| | | Concentration of Compound 11 (μM) | | | | |
|---|---|---|---|---|---|---|
| | | 0.78125 | 0.390625 | 0.1953125 | 0.0976563 | 0.0488281 |
| Concentration of Gemcitabine (μM) | 0.390625 | dead | dead | dead | dead | dead |
| | 0.195313 | dead | dead | dead | dead | dead |
| | 0.097656 | dead | dead | dead | dead | dead |
| | 0.048828 | alive | alive | alive | alive | alive |
| | 0.024414 | alive | alive | alive | alive | alive |

Once again, both combinations tested produced a synergistic effect, as shown by the FIC values. The data in Table 7 further demonstrate the cytotoxic activity 11 and Gemcitabine has against AsPc-1 cells, wherein concentrations as low as 0.0488 μM of 11 and 0.977 μM of Gemcitabine result is AsPc-1 cell death.

Because Gemcitabine will kill any cells that are rapidly dividing, some adverse effects of Gemcitabine treatment include loss of white blood cells, platelets, and red blood cells, as well as hair loss, nausea, and vomiting. The synergistic effect observed for the combination of 11 and Gemcitabine indicates that lower concentrations of Gemcitabine may be administered with 11 to produce the same therapeutic effect as a treatment of higher concentrations of Gemcitabine alone, thus alleviating some of the adverse effects associated with Gemcitabine treatment.

The invention claimed is:

1. A compound, or a pharmaceutically acceptable salt thereof, of the following formula:

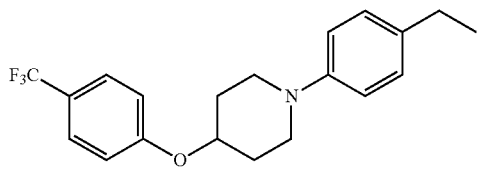

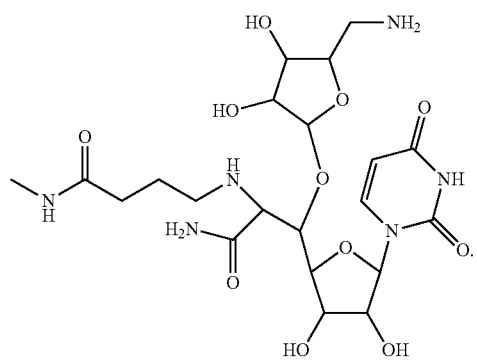

2. A compound, or a pharmaceutically acceptable salt thereof, of the following formula:
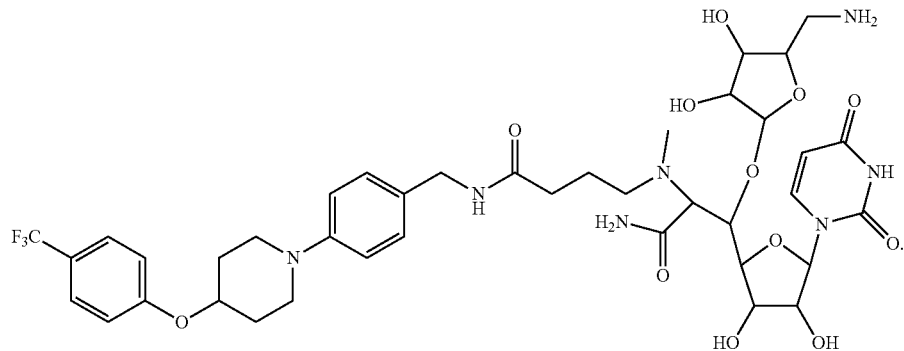 [SMILES: CN(CCCC(=O)NCc1ccc(N2CCC(Oc3ccc(C(F)(F)F)cc3)CC2)cc1)C(C(N)=O)C(OC1OC(CN)C(O)C1O)C1OC(n2ccc(=O)[nH]c2=O)C(O)C1O]
3. The compound of claim 2, or a pharmaceutically acceptable salt thereof, wherein the compound has the following stereochemistry:
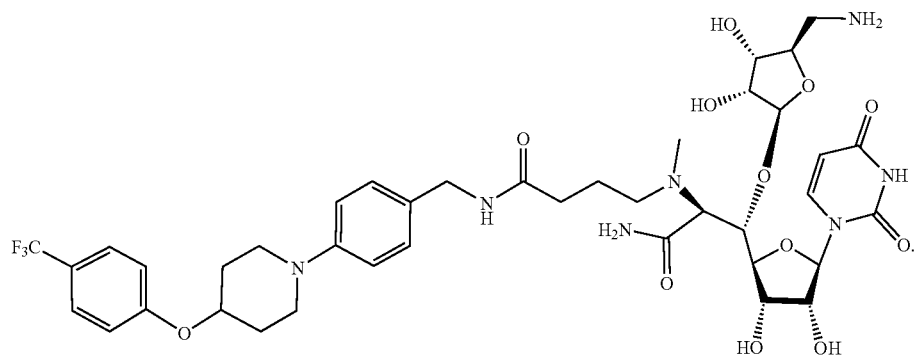
4. A compound, or a pharmaceutically acceptable salt thereof, having the following stereochemistry:
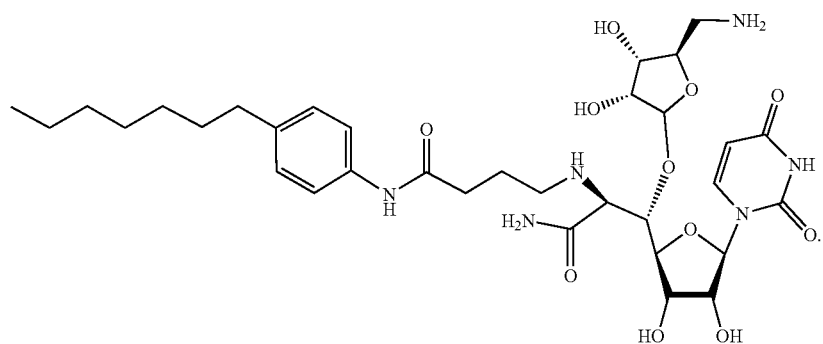

5. A compound, or a pharmaceutically acceptable salt thereof, having the following stereochemistry:

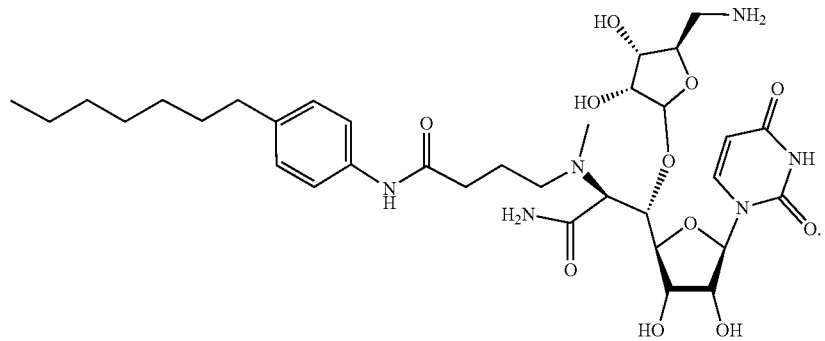

6. A method of treating cancer in an individual in need thereof, comprising administering to the individual a therapeutically effective amount of a compound according to claim 1.

7. The method of claim 6, wherein the method further comprises administering a second compound that is taxol or gemcitabine.

8. A method of treating cancer in an individual in need thereof, comprising administering to the individual a therapeutically effective amount of a compound according to claim 2.

9. The method of claim 8, wherein the method further comprises administering a second compound that is taxol or gemcitabine.

* * * * *